United States Patent
Bishara et al.

(10) Patent No.: US 11,534,239 B2
(45) Date of Patent: Dec. 27, 2022

(54) SYSTEMS AND METHOD OR USES OF ABLATING CARDIAC TISSUE

(71) Applicant: Biosense Webster (Israel) Ltd., Yokneam (IL)

(72) Inventors: Moe Habib Bishara, Irvine, CA (US); Nader Ghaly, Irvine, CA (US); Kendra Anita Mcinnis, Irvine, CA (US); Assaf Govari, Haifa (IL); Christopher Thomas Beeckler, Brea, CA (US); Joseph Thomas Keyes, Sierra Madre, CA (US); Rowan Olund Hettel, Irvine, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 443 days.

(21) Appl. No.: 16/569,585

(22) Filed: Sep. 12, 2019

(65) Prior Publication Data
US 2020/0046422 A1 Feb. 13, 2020

Related U.S. Application Data

(63) Continuation-in-part of application No. 14/578,807, filed on Dec. 22, 2014.
(Continued)

(51) Int. Cl.
*A61B 18/12* (2006.01)
*A61B 18/14* (2006.01)
(Continued)

(52) U.S. Cl.
CPC ........ *A61B 18/1492* (2013.01); *A61B 5/4848* (2013.01); *A61B 5/6853* (2013.01);
(Continued)

(58) Field of Classification Search
CPC ........ A61B 18/1492; A61B 2018/0022; A61B 2018/0016; A61B 2018/00375;
(Continued)

(56) References Cited

U.S. PATENT DOCUMENTS 5,718,241 A 2/1998 Ben-Haim et al.
6,198,974 B1 5/2001 Webster, Jr.
(Continued)

FOREIGN PATENT DOCUMENTS

| EP | 2 749 214 A1 | 7/2014 |
| EP | 2 875 790 A2 | 5/2015 |
| WO | 2018/129133 A1 | 7/2018 |

OTHER PUBLICATIONS

"Multi-Electrode RF Balloon Efficient for Acute Pulmonary Vein Isolation." DAIC, May 17, 2017, www.dicardiology.com/article/multi-electrode-rf-balloon-efficient-acute-oulmonary-vein-isolation. (Year: 2017).*
(Continued)

*Primary Examiner* — Jaymi E Della
(74) *Attorney, Agent, or Firm* — Troutman Pepper Hamilton Sanders LLP; Louis J DelJuidice; Korbin M. Blunck

(57) ABSTRACT

The subject of this disclosure is devices, systems, and uses thereof to treat a plurality of patients for paroxysmal atrial fibrillation. The solution can include delivering a multi-electrode radiofrequency balloon catheter and a multi-electrode diagnostic catheter to one or more targeted pulmonary veins; ablating tissue of the one or more targeted pulmonary veins using the multi-electrode radiofrequency balloon catheter; diagnosing the one or more targeted pulmonary veins using the multi-electrode diagnostic catheter; and achieving at least one of a predetermined clinical effectiveness and acute effectiveness of the method or use based on use of the multi-electrode radiofrequency balloon catheter and the
(Continued)

US 11,534,239 B2
Page 2 multi-electrode diagnostic catheter in the isolation of the one or more targeted pulmonary veins.

19 Claims, 27 Drawing Sheets

Related U.S. Application Data

(60) Provisional application No. 62/731,525, filed on Sep. 14, 2018, provisional application No. 62/754,275, filed on Nov. 1, 2018, provisional application No. 62/771,896, filed on Nov. 27, 2018, provisional application No. 62/873,636, filed on Jul. 12, 2019, provisional application No. 62/886,729, filed on Aug. 14, 2019, provisional application No. 62/889,471, filed on Aug. 20, 2019.

(51) Int. Cl.
```
A61B 5/00      (2006.01)
A61B 34/10     (2016.01)
G16H 20/40     (2018.01)
A61B 18/00     (2006.01)
A61M 25/10     (2013.01)
```

(52) U.S. Cl.
CPC ............ *A61B 34/10* (2016.02); *G16H 20/40* (2018.01); *A61B 5/0006* (2013.01); *A61B 2018/0016* (2013.01); *A61B 2018/0022* (2013.01); *A61B 2018/00375* (2013.01); *A61B 2018/00577* (2013.01); *A61B 2018/00654* (2013.01); *A61B 2018/00702* (2013.01); *A61B 2018/00839* (2013.01); *A61B 2018/00886* (2013.01); *A61B 2218/002* (2013.01); *A61B 2562/0209* (2013.01); *A61B 2562/043* (2013.01); *A61M 25/1018* (2013.01); *A61M 2025/105* (2013.01)

(58) Field of Classification Search
CPC ........... A61B 2018/00577; A61B 2018/00654; A61B 2018/00702
See application file for complete search history.

(56) References Cited

U.S. PATENT DOCUMENTS

| | | |
|---|---|---|
| 6,322,558 B1 | 11/2001 | Taylor et al. |
| 6,484,118 B1 | 11/2002 | Govari |
| 6,987,995 B2 | 1/2006 | Drysen |
| 7,142,903 B2 | 11/2006 | Rodriguez et al. |
| 7,274,957 B2 | 9/2007 | Drysen |
| 7,377,906 B2 | 5/2008 | Selkee |
| 7,591,799 B2 | 9/2009 | Selkee |
| 7,593,760 B2 | 9/2009 | Rodriguez et al. |
| 7,720,517 B2 | 5/2010 | Drysen |
| 7,853,302 B2 | 12/2010 | Rodriguez et al. |
| 8,000,765 B2 | 8/2011 | Rodriguez et al. |
| 8,021,327 B2 | 9/2011 | Selkee |
| 8,275,440 B2 | 9/2012 | Rodriguez et al. |
| 8,348,888 B2 | 1/2013 | Selkee |
| 9,907,610 B2 | 3/2018 | Beeckler et al. |
| 9,956,035 B2 | 5/2018 | Govari et al. |
| 2002/0068931 A1 | 6/2002 | Wong et al. |
| 2003/0028183 A1 | 2/2003 | Sanchez et al. |
| 2003/0144658 A1 | 7/2003 | Schwartz et al. |
| 2004/0147920 A1 | 7/2004 | Keidar |
| 2006/0106375 A1* | 5/2006 | Werneth ............ A61B 18/1492 606/32 |
| 2008/0208186 A1* | 8/2008 | Slater ................ A61B 18/1492 606/41 |
| 2008/0281312 A1* | 11/2008 | Werneth ............ A61B 18/1492 606/33 |
| 2012/0101538 A1 | 4/2012 | Ballakur et al. |
| 2012/0143177 A1 | 6/2012 | Avitall |
| 2012/0143293 A1 | 6/2012 | Mauch et al. |
| 2012/0209260 A1 | 8/2012 | Lambert et al. |
| 2013/0150693 A1 | 6/2013 | D'Angelo et al. |
| 2013/0169624 A1 | 7/2013 | Bourier et al. |
| 2014/0012242 A1 | 1/2014 | Lee et al. |
| 2014/0275993 A1 | 9/2014 | Ballakur |
| 2015/0112321 A1 | 4/2015 | Cadouri |
| 2015/0272667 A1 | 10/2015 | Govari et al. |
| 2015/0327805 A1 | 11/2015 | Ben-Haim |
| 2016/0175041 A1 | 6/2016 | Govari et al. |
| 2017/0311829 A1 | 11/2017 | Beeckler et al. |
| 2017/0311893 A1 | 11/2017 | Beeckler et al. |
| 2017/0312022 A1 | 11/2017 | Beeckler et al. |
| 2017/0347896 A1 | 12/2017 | Keyes et al. |
| 2017/0348049 A1 | 12/2017 | Vrba et al. |
| 2018/0125575 A1 | 5/2018 | Schwartz et al. |
| 2018/0161093 A1 | 6/2018 | Basu et al. |
| 2018/0280080 A1 | 10/2018 | Govari et al. |
| 2019/0060622 A1 | 2/2019 | Beeckler |
| 2019/0143079 A1 | 5/2019 | Beeckler et al. |
| 2019/0175262 A1 | 6/2019 | Govari et al. |
| 2019/0183567 A1 | 6/2019 | Govari et al. |
| 2019/0217065 A1 | 7/2019 | Govari et al. |
| 2019/0298441 A1 | 10/2019 | Clark et al. |
| 2019/0365451 A1 | 12/2019 | Jung, Jr. |
| 2020/0001054 A1 | 1/2020 | Jimenez et al. |
| 2020/0155226 A1 | 5/2020 | Valls et al. |

OTHER PUBLICATIONS

S Honarbakhsh, S Birch, V Baker, B O'Brien, M Lowe, RJ Hunter, RJ Schilling. "Radiofrequency balloon catheter ablation for paroxysmal atrial fibrillation, RADIANCE STUDY—a UK experience." EP Europace, vol. 19, Issue 1, Oct. 2017, Page i21. (Year: 2017).*

Dorobantu, Maria, and Radu Vatasescu. "Oral anticoagulation during atrial fibrillation ablation: Facts and controversies." Cor et Vasa, vol. 55, Issue 2, 2013, Pages e101-e106. (https://www.sciencedirect.com/science/article/pii/S0010865012001415) (Year: 2013).*

Winkle RA, Mead RH, Engel G, Kong MH, Patrawala RA. Atrial fibrillation ablation using open-irrigated tip radiofrequency: experience with intraprocedural activated clotting times ≤210 seconds. Heart Rhythm. Jun. 2014;11(6):963-8. Epub Mar. 27, 2014. (Year: 2014).*

Okano T, Okada A, Tabata H, Kobayashi H, Shoin W, Yoshie K, Oguchi Y, Shoda M, Kuwahara K. Wire perforation causing cardiopulmonary arrest during radiofrequency hot balloon ablation for pulmonary vein isolation. J Cardiol Cases. Feb. 15, 2019;19(5):169-172. (Year: 2019).*

Napoli, N. (Mar. 19, 2017). For atrial fibrillation ablation, newer anticoagulant reduces major bleeds. American College of Cardiology. Retrieved Jan. 21, 2022. https://www.acc.org/about-acc/press-releases/2017/03/18/08/47/sun-1045am-for-atrial-fibrillation-ablation-newer-anticoagulant-reduces-majo.*

"Multi-Electrode RF Balloon Efficient for Acute Pulmonary Vein Isolation." DAIC, May 17, 2017, www.dicardiology.com/article/multi-electrode-rf-balloon-efficient-acute-pulmonary-vei n-isolation. (Year: 2017) cited in OA issued in corresponding U.S. Appl. No. 17/096,484 dated Dec. 28, 2020.

O'Neill, Angela. "AF Symposium 2017: First-in-Man Study Shows Promising Results with a Multi-Electrode Radiofrequency Balloon for Paroxysmal AF Treatment." Cardiac Rhythm News, Jan. 20, 2017, (Year: 2017) https://cardiacrhythmnews.com/fist-in-man-study-shows-promising-results-with-a-multi-electrode-radiofrequency-balloon-for-paroxysmal-af-treatment/ (Year: 2017) cited in OA issued in corresponding U.S. Appl. No. 17/096,484 dated Dec. 28, 2020.

Vivek Y. Reddy, Petr Neuzil, Andre d'Avila, Margaret Laragy, Zachary J. Malchano, Stepan Kralovec, Steven J. Kim, Jeremy N. Ruskin, Balloon catheter ablation to treat paroxysmal atrial fibrillation: What is the level of pulmonary enous isolation?, Heart Rhythm. Vol. 5:3. Mar. 2008. pp. 353-360. (Year: 2008) cited in OA issued in corresponding U.S. Appl. No. 17/096,484 dated Dec. 28, 2020.

(56) References Cited

OTHER PUBLICATIONS

Nagashima, Koichi, et al. Hot Balloon Versus Cryoballoon Ablation for Atrial Fibrillation. Circulation: arrhythmia and Electrophysiology. vol. 11 :5. May 2018. (Year: 2018) cited in OA issued in corresponding U.S. Appl. No. 17/096,484 dated Dec. 28, 2020.

International Search Report and Written Opinion issued in corresponding International Application No. PCT/B2019/057742 dated Nov. 28, 2019.

International Search Report and Written Opinion issued in corresponding International Patent Application No. PCT/IB2019/057743 dated Dec. 6, 2019.

Casella, M., et al. "Ablation Index as a predictor of long-term efficacy in premature ventricular complex ablation: A regional target value analysis" Heart Rhythm Society pp. 888-895 (2019).

Das. M., et al. "Ablation index, a novel marker of ablation lesion quality: prediction of pulmonary vein reconnection at repeat electrophysiology study and regional differences in target values" Europace 19:775-783 (2017).

\* cited by examiner

| Parameter | Unipolar Mode |
|---|---|
| Inside Sheath Flow Rate | 5 ml/min |
| Idle Flow Rate | 5 ml/min |
| Irrigation Flow Rate During RF Application | 35 ml/min |
| Power Setting | Max 15 W |
| Temperature Setting* | Max 55 °C |
| Application Time Anterior Electrodes | Max 60 sec |
| Application Time Posterior Electrodes | Max 20 sec |

Fig. 14

| | |
|---|---|
| Mild | Awareness of signs, symptoms, or events that are otherwise easily tolerated that may result in minimal transient impairment of a body function or damage to a body structure, but do not require intervention other than monitoring. |
| Moderate | Any event that results in moderate transient impairment of a body function or damage to a body structure that causes interference with usual activities, or that warrants possible intervention, such as the administration of medication, to prevent permanent impairment of a body function or damage to a body structure. |
| Severe | Any event that is incapacitating (an inability to do usual activities) or is life-threatening and results in permanent impairment of a body function or damage to a body structure, or requires intervention, such as major surgery, to prevent permanent impairment of a body function or damage to a body structure. |

Fig. 15

|  | Blanking period (≤ 90 days post procedure) | Post blanking period (> 90 days post procedure) |
|---|---|---|
| New Class I and/or Class III AAD | Can be initiated; subject will not be classified as a primary effectiveness failure. | Should NOT be initiated in the absence of AF recurrence; subject will be classified as a primary effectiveness failure.<br><br>Should NOT be continued past 90-days post-ablation (if initiated in blanking). Subject will be classified as a primary effectiveness failure |
| Previously failed Class I and/or Class III AAD (> highest historically failed dose) | Can be initiated; subject will not be classified as a primary effectiveness failure.<br><br>Can be continued (from prior to study enrollment); subject will not be classified as a primary effectiveness failure. | Should NOT be initiated in the absence of AF recurrence; subject will be classified as a primary effectiveness failure.<br><br>Should NOT be continued past 90-days post-ablation (if initiated in blanking). Subject will be classified as a primary effectiveness failure |
| Previously failed Class I and/or Class III AAD (≤ highest historically failed dose) | Can be initiated; subject will not be classified as a primary effectiveness failure.<br><br>Can be continued (from prior to study enrollment); subject will not be classified as a primary effectiveness failure. | Can be initiated; subject will not be classified as a primary effectiveness failure.<br><br>Can be continued past 90-days postablation (if initiated in blanking). Subject will not be classified as a primary effectiveness failure. |
| Class II and/or Class IV AAD | Can be initiated, continued, or increased and subject will not be classified as a primary effectiveness failure. | Can be initiated, continued, or increased and subject will not be classified as a primary effectiveness failure. |

Fig. 16

| Characteristic[a] | Prior Study (N = 38) | First Study (N = 31) |
|---|---|---|
| Sex | | |
|   Male | 22 (57.9) | 22 (71.0) |
|   Female | 16 (42.1) | 9 (29.0) |
| Age, years | | |
|   Mean (standard deviation) | 60.8 (10.04) | 59.3 (8.08) |
|   Range | 36.0-81.0 | 34.0-72.0 |
| Cardiovascular medical history | | |
|   Hypertension (systemic) | 21 (55.3) | 13 (41.9) |
|   Myocardial infarction | 2 (5.3) | 0 |
|   Coronary disease | 1 (2.6) | 1 (3.2) |
|   NYHA Class II congestive heart failure | 1 (2.6) | 0 |
|   Vascular disease | 0 | 1 (3.2) |
|   Had implantable device | 0 | 1 (3.2) |
|   PCI, cardiac surgery, or valvular cardiac surgical or percutaneous procedure | 0 | 1 (3.2) |
|   Other cardiovascular medical condition | 7 (18.4) | 2 (6.5) |
| Thromboembolic events | | |
|   Transient ischemic attacks | 1 (2.6) | 1 (3.2) |
|   Other thromboembolic events | 3 (7.9) | 0 |
| Type II diabetes | 5 (13.2) | 3 (9.7) |

```
delivering a multi-electrode radiofrequency balloon
catheter to one or more targeted pulmonary veins
2010
```
↓
```
ablating tissue of the pulmonary vein using the multi-
electrode radiofrequency balloon catheter
2020
```
↓
```
achieving a predetermined effectiveness rate of
pulmonary vein isolation
2030
```

Fig. 20

2100
delivering a multi-electrode radiofrequency balloon catheter to a pulmonary vein
2110
ablating tissue of the pulmonary vein using the multi-electrode radiofrequency balloon catheter
2120
achieving a predetermined success rate of pulmonary vein isolation
2130
Fig. 21

2200 ⟶
delivering a multi-electrode radiofrequency balloon
catheter to a pulmonary vein
2210
ablating tissue of the pulmonary vein using the multi-
electrode radiofrequency balloon catheter
2220
achieving pulmonary vein isolation and at least a 97%
safety endpoint within seven (7) days of successful
pulmonary vein isolation
2230
Fig. 22

2300
delivering a multi-electrode radiofrequency balloon catheter to a pulmonary vein
2310
ablating tissue of the pulmonary vein using the multi-electrode radiofrequency balloon catheter
2320
achieving pulmonary vein isolation and at least a 90% safety endpoint within seven (7) days of successful pulmonary vein isolation
2330
Fig. 23

2400

```
┌─────────────────────────────────────────────────────────────┐
│ delivering a multi-electrode radiofrequency balloon catheter │
│ having a plurality of independently controllable electrodes  │
│ for radiofrequency ablation and a multi-electrode diagnostic │
│ catheter to one or more targeted pulmonary veins             │
│ 2410                                                         │
└─────────────────────────────────────────────────────────────┘
                              │
                              ▼
┌─────────────────────────────────────────────────────────────┐
│ ablating tissue of the one or more targeted pulmonary veins  │
│ with one or more of the plurality of the electrodes          │
│ independently controlled multi-electrode radiofrequency      │
│ balloon catheter                                             │
│ 2420                                                         │
└─────────────────────────────────────────────────────────────┘
                              │
                              ▼
┌─────────────────────────────────────────────────────────────┐
│ diagnosing the one or more targeted pulmonary veins using    │
│ the multi-electrode diagnostic catheter                      │
│ 2430                                                         │
└─────────────────────────────────────────────────────────────┘
                              │
                              ▼
┌─────────────────────────────────────────────────────────────┐
│ achieving at least one of a predetermined clinical           │
│ effectiveness and acute effectiveness of the method based on │
│ use of the multi-electrode radiofrequency balloon catheter   │
│ and the multi-electrode diagnostic catheter in the isolation │
│ of the one or more targeted pulmonary veins                  │
│ 2440                                                         │
└─────────────────────────────────────────────────────────────┘
```

--- delivering a multi-electrode radiofrequency balloon catheter having a plurality of independently controllable electrodes for radiofrequency ablation and a multi-electrode diagnostic catheter to one or more targeted pulmonary veins
2510

--- ablating tissue of one or more targeted pulmonary veins with one or more of the plurality of the electrodes independently controlled multi-electrode radiofrequency balloon catheter
2520

--- diagnosing all targeted pulmonary veins using the multi-electrode diagnostic catheter
2530

--- achieving a predetermined rate of adverse events based on use of the multi-electrode radiofrequency balloon catheter and the multi-electrode diagnostic catheter in the isolation of all targeted pulmonary veins, during and approximately 6 months after the method
2540

```
administering a heparin bolus prior to transseptal puncture 2710
                            ↓
providing transseptal access for a multi-electrode radiofrequency
balloon catheter and a mapping catheter across a septum 2720
                            ↓
using a lasso catheter for at least one septum puncture 2730
                            ↓
irrigating, by the balloon catheter, continuously at or about all targeted
veins 2740
                            ↓
confirming activated clotting time between approximately about 350
and 400 seconds prior to inserting the balloon catheter into a left
atrium 2750
                            ↓
performing pulmonary vein ablation with the balloon catheter with a
maximum temperature setting of the balloon catheter being
approximately about 55 °C thereby achieving at least one of a
predetermined clinical effectiveness and acute effectiveness of the
multi-electrode radiofrequency balloon catheter in the isolation of the
targeted pulmonary veins, during and approximately 3 months after
ablation 2750
```

Fig. 27

SYSTEMS AND METHOD OR USES OF ABLATING CARDIAC TISSUE

CROSS-REFERENCE TO RELATED APPLICATIONS

This application is a continuation in part application of U.S. patent application Ser. No. 14/578,807, filed on Dec. 22, 2014 and also claims priority to U.S. provisional patent application No. 62/731,525 filed Sep. 14, 2018, U.S. provisional patent application No. 62/754,275 filed Nov. 1, 2018, U.S. provisional patent application No. 62/771,896 filed Nov. 27, 2018, and to U.S. provisional patent application No. 62/873,636 filed Jul. 12, 2019, U.S. provisional patent application No. 62/886,729 filed Aug. 14, 2019, and to U.S. provisional patent application No. 62/889,471 filed Aug. 20, 2019. The contents of these United States non-provisional patent application and provisional patent applications are incorporated herein by reference in their entirety as if set forth verbatim.

FIELD

This disclosure relates to medical devices.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

With this in mind, it is understood that AF is the most common sustained arrhythmia in humans. It affects anywhere from 0.4% to 1% of the general population and increases in prevalence with age to approximately 10% in patients over 80 years of age. The primary clinical benefit of AF ablation is improvement in quality of life resulting from the elimination of arrhythmia-related symptoms such as palpitations, fatigue, or effort intolerance.

However, due to variances in human anatomy, ostia and tubular regions in the heart come in all sizes. Thus, conventional balloon or inflatable catheters may not have necessary flexibility to accommodate different shapes and sizes while having sufficient structural support for effective circumferential contact with tissue. In particular, ablation electrodes that provide greater surface contact may lack sufficient flexibility. Moreover, delicate wires such as those of electrode lead wires and/or thermocouple wires and their solder joints need support and protection from breakage and damage during both assembly and use in the patient's body. Additionally, because the balloon configuration is radially symmetrical and multiple electrode elements surround the balloon configuration, determining the orientation of the balloon electrode assembly under fluoroscopy has also posed challenges.

SUMMARY

Accordingly, the inventors of this disclosure have recognized that there is a need for a balloon or a catheter having an inflatable member with contact electrodes that can contact more tissue area while remaining sufficiently flexible to accommodate different anatomy and the tighter space constraints of an ostium and a pulmonary vein. The inventors have recognized a need for a balloon catheter to carry an electrode assembly with adaptations for the ostium and pulmonary vein that can be manufactured from a generic flexible circuit. There is a further desire for a balloon catheter capable of multiple functions including diagnostic and therapeutic functions, such as ablation, pacing, navigation, temperature sensing, electropotential sensing and impedance sensing, and be adaptive for use with other catheters, including a lasso catheter or a focal catheter.

The solution of this disclosure resolves these and other issues of the art.

The subject of this disclosure is the use of a multi-electrode RF balloon catheter and a multi-electrode diagnostic catheter for the treatment of paroxysmal atrial fibrillation (PAF) to achieve at least one of a predetermined clinical effectiveness and acute effectiveness for a predetermined population size. The inventors believe that there are theoretical advantages of a multi-electrode RF balloon catheter in conjunction with the multi-electrode diagnostic catheter of this disclosure, which includes high probability of single-shot pulmonary vein isolation with minimal collateral damage to non-pulmonary vein structures, but without the drawbacks of excessive heating or cooling of the surrounding tissue. In some examples, a multi-electrode RF balloon of the multi-electrode RF balloon catheter is configured to deliver directionally-tailored energy using multiple electrodes, optimizing safety and/or efficacy. In particular, examples of this disclosure are suited for isolation of the atrial pulmonary veins in treatment of subjects with paroxysmal atrial fibrillation.

In some examples, a method or use is disclosed to treat a plurality of patients for paroxysmal atrial fibrillation. The method or use is disclosed to treat a plurality of patients for paroxysmal atrial fibrillation, the method comprising the steps of administering a heparin bolus prior to transseptal puncture; providing transseptal access for a multi-electrode radiofrequency balloon catheter and a mapping catheter across a septum; using a lasso catheter for at least one septum puncture; irrigating, by the balloon catheter, continuously at or about all targeted veins; confirming activated clotting time between approximately about 350 and 400 seconds prior to inserting the balloon catheter into a left atrium; and performing pulmonary vein ablation with the balloon catheter with a maximum temperature setting of the balloon catheter being approximately about 55° C. thereby achieving at least one of a predetermined clinical effectiveness and acute effectiveness of the multi-electrode radiofrequency balloon catheter in the isolation of the targeted pulmonary veins, during and approximately 3 months after ablation.

In some examples, the step of performing pulmonary vein isolation comprises ablating tissue of the targeted veins with one or more of a plurality of independently controlled electrodes of the balloon catheter.

In some examples, for a patient population, silent cerebral lesion incidences at discharge are approximately about 10% of the patients.

In some examples, for a patient population, silent cerebral lesion incidences at discharge are approximately about 10% of the patients.

In some examples, the method includes reducing silent cerebral lesion incidences at discharge by approximately about 50% for the patients in comparison to a clinically approved RF balloon catheter performing pulmonary vein isolation according to a different ablation workflow.

In some examples, the method includes reducing incidence of minor stroke for the patients in comparison to a clinically approved RF balloon catheter performing pulmonary vein isolation according to a different ablation workflow.

In some examples, the method includes achieving a mean activated clotting time of approximately about 380 seconds for all patients.

In some examples, the method includes increasing mean activated clotting time by approximately about 36 seconds for all patients in comparison to a clinically approved RF balloon catheter performing pulmonary vein isolation according to a different ablation workflow.

In some examples, the method includes increasing mean activated clotting time by approximately about 10% for all patients in comparison to a clinically approved RF balloon catheter performing pulmonary vein isolation according to a different ablation workflow.

In some examples, the method includes achieving a mean activated clotting time of approximately about 376 seconds for all patients with silent cerebral lesion.

In some examples, the method includes increasing mean activated clotting time by approximately about 27 seconds for all patients with silent cerebral lesion in comparison to a clinically approved RF balloon catheter performing pulmonary vein isolation according to a different ablation workflow.

In some examples, the method includes increasing mean activated clotting time by approximately about 8% for all patients with silent cerebral lesion in comparison to a clinically approved RF balloon catheter performing pulmonary vein isolation according to a different ablation workflow.

In some examples, the method includes achieving a mean activated clotting time of approximately about 380 seconds for all patients without silent cerebral lesion.

In some examples, the method includes increasing mean activated clotting time by approximately about 38 seconds for all patients without silent cerebral lesion in comparison to a clinically approved RF balloon catheter performing pulmonary vein isolation according to a different ablation workflow.

In some examples, the method includes increasing mean activated clotting time by approximately about 11% for all patients without silent cerebral lesion in comparison to a clinically approved RF balloon catheter performing pulmonary vein isolation according to a different ablation workflow.

In some examples, a patient population for the method is at least approximately about 98 patients.

In some examples, a patient population for the method is at least approximately about 40 patients.

In some examples, a method or use is disclosed to treat a plurality of patients for paroxysmal atrial fibrillation. The method or use can include delivering a multi-electrode radiofrequency balloon catheter and a multi-electrode diagnostic catheter to one or more targeted pulmonary veins; ablating tissue of the one or more targeted pulmonary veins using the multi-electrode radiofrequency balloon catheter; diagnosing the one or more targeted pulmonary veins using the multi-electrode diagnostic catheter; and achieving at least one of a predetermined clinical effectiveness and acute effectiveness of the procedure based on use of the multi-electrode radiofrequency balloon catheter and the multi-electrode diagnostic catheter in the isolation of the one or more targeted pulmonary veins.

In some examples, the acute effectiveness is defined by confirming if there is an entrance block in all targeted pulmonary veins after adenosine and/or isoproterenol challenge.

In some examples, the acute effectiveness is further defined by success greater than 90% for the plurality of patients.

In some examples, the acute effectiveness is further defined by success greater than 95% for the plurality of patients.

In some examples, a Type-1 error rate for power the acute effectiveness and the clinical effectiveness of all targeted veins are controlled at approximately a 5% level. The method or use can include determining whether the procedure is clinically successful for the plurality of patients if both the acute effectiveness and the clinical effectiveness indications are controlled at approximately the 5% level.

In some examples, the acute effectiveness is at least 80% for the plurality of patients being at least 80 patients, 130 patients, and/or 230 patients.

In some examples, the acute effectiveness is further defined by confirming if there is an entrance block in all targeted pulmonary veins after adenosine and/or isoproterenol challenge using a focal ablation catheter.

In some examples, the acute effectiveness is further defined by confirming if there is an entrance block in all targeted pulmonary veins after adenosine and/or isoproterenol challenge without using a focal ablation catheter.

In some examples, the procedure is administered on the plurality of patients diagnosed with symptomatic paroxysmal atrial fibrillation.

In some examples, the predetermined effectiveness rate is defined by an average number of RF applications per patient and RF time required to isolate all pulmonary veins. the step of diagnosing further comprises: electrophysiological mapping of the heart.

In some examples, the multi-electrode diagnostic catheter further comprises a high torque shaft with a halo-shaped tip section containing a plurality of pairs of electrodes visible under fluoroscopy.

In some examples, the predetermined acute effectiveness is defined by ulceration being absent in the plurality of patients after the procedure.

In some examples, the predetermined acute effectiveness is defined by a complication rate of approximately 13% or fewer of the plurality of patients experiencing esophageal erythema after the procedure.

In some examples, the predetermined acute effectiveness is defined by a complication rate of approximately 25% or fewer of the plurality of patients experiencing new asymptomatic cerebral embolic lesions after the procedure.

In some examples, the predetermined acute effectiveness is defined by a complication rate of approximately 20% or fewer of the plurality of patients experiencing new asymptomatic cerebral embolic lesions after the procedure.

In some examples, wherein the predetermined acute effectiveness is defined by a complication rate of approximately 5-9% or fewer of the plurality of patients experiencing a primary adverse event by approximately 7 or more days after the procedure.

In some examples, inclusion criteria for the plurality of patients includes a diagnosis with symptomatic paroxysmal atrial fibrillation and a patient capability to comply with uninterrupted per-protocol anticoagulation requirements.

In some examples, the predetermined acute effectiveness is defined by a total procedure time.

In some examples, a population size for the predetermined success rate is at least 80 patients, 130 patients, 180 patients, and/or 230 patients.

In some examples, the predetermined acute effectiveness is defined by a total RF application time.

In some examples, the predetermined acute effectiveness is defined by a total dwell time of the multi-electrode radiofrequency balloon catheter.

In some examples, the predetermined acute effectiveness is defined by a total time to isolate all targeted pulmonary veins.

In some examples, the predetermined acute effectiveness is defined by a number and a total time of applications by the multi-electrode radiofrequency balloon catheter per location of all targeted pulmonary veins.

In some examples, the predetermined acute effectiveness is defined by a number and a total time of applications by the multi-electrode radiofrequency balloon catheter per patient.

In some examples, the predetermined acute effectiveness is defined by a number and a total time of applications by the multi-electrode radiofrequency balloon catheter per targeted vein.

In some examples, multi-electrode radiofrequency balloon catheter comprises a compliant balloon with a plurality of electrodes bonded configured to deliver RF energy to tissue of the pulmonary vein and sense temperature at each electrode.

In some examples, clinical effectiveness is defined by an incidence of early onset of one or more adverse events within a predetermined time of the procedure being implemented.

In some examples, the predetermined time is at least 7 days.

In some examples, the one or more adverse events comprise: death, atrio-esophageal fistula, myocardial infarction, cardiac tamponade/perforation, thromboembolism, stroke, TIA (Transient Ischemic Attack), phrenic nerve paralysis, pulmonary vein stenosis, and major vascular access bleeding.

In some examples, the one or more adverse events comprise: incidence of individual adverse events from a primary composite; incidence of serious adverse device effect; incidence of serious adverse events within 7 days, at least 7-30 days, and at least 30 days following the procedure; incidence of non-serious adverse events; incidence of pre- and post-ablation asymptomatic and symptomatic cerebral emboli as determined by MRI evaluation; and frequency, anatomic location, and size (diameter and volume) of cerebral emboli by MRI evaluations at baseline, post-ablation and during follow-up.

In some examples, the one or more adverse events for approximately 8% of the plurality of patients, the one or more adverse events comprising: NIHSS (National Institute of Health Stroke Scale) scores at baseline, post-ablation and during follow-up; a summary of MoCA (Montreal Cognitive Assessment) and mRS (Modified Ranking Scale) scores at baseline, 1 month and during further follow-up; a rate of hospitalization for cardiovascular events; a percentage (%) of pulmonary vein isolation touch-up by focal catheter among the one or more targeted veins; a percentage (%) of subjects with use of focal catheter ablations for non-PV triggers; a percentage (%) of subjects with freedom from documented symptomatic atrial fibrillation (AF), atrial tachycardia (AT), or atypical (left side) atrial flutter (AFL) episodes (episodes >30 seconds on arrhythmia monitoring device from day 91 to 180); a percentage (%) of subjects with freedom from documented atrial fibrillation (AF), atrial tachycardia (AT), or atypical (left side) atrial flutter (AFL); one or more episodes that endure for 30 or more seconds on an arrhythmia monitoring device from day 91 to 180 following the procedure; and one or more procedural parameters including total procedure and ablation time, balloon dwell time, RF application time, a number of RF applications, fluoroscopy time and dose.

In some examples, the acute safety rate includes complication rates of 10% or less and is defined by incidence of asymptomatic cerebral embolic lesions at a discharge magnetic resonance imaging (MRI).

In some examples, the acute effectiveness rate includes complication rates of approximately 0% and is defined by existence of esophageal injury erythema.

In some examples, the acute effectiveness rate is 100% and is defined by electrically isolating all targeted pulmonary veins without use of a focal ablation catheter.

In some examples, the acute effectiveness rate is defined by a freedom from documented atrial fibrillation, atrial tachycardia, or atypical atrial flutter episodes based on electrocardiographic data through an effectiveness evaluation period (1 year).

In some examples, the acute effectiveness rate is defined by pulmonary vein isolation touch-up by a focal catheter among all targeted pulmonary veins.

In some examples, the predetermined clinical effectiveness rate is defined by 10% or less complication rates related to incidence of post-ablation symptomatic and asymptomatic cerebral emboli as compared to pre-ablation.

In some examples, the multi-electrode diagnostic catheter is configured for electrophysiological recording and stimulation of the atrial region of the heart and is used in conjunction with the multi-electrode radiofrequency balloon catheter.

In some examples, a method or use of administering a procedure to treat a plurality of patients for paroxysmal atrial fibrillation. The method or use includes delivering a multi-electrode radiofrequency balloon catheter and a multi-electrode diagnostic catheter to one or more targeted pulmonary veins; and ablating tissue of all targeted pulmonary veins using the multi-electrode radiofrequency balloon catheter; diagnosing all targeted pulmonary veins using the multi-electrode diagnostic catheter; and achieving a predetermined rate of adverse events, using the multi-electrode radiofrequency balloon catheter and the multi-electrode diagnostic catheter in the isolation of all targeted pulmonary veins, during and approximately 6 months after the procedure.

In some examples, a method or use of treating a plurality of patients for paroxysmal atrial fibrillation. The method or use includes evaluating a number and size of all targeted pulmonary veins and anatomy of the left atrial; puncturing the transseptal; selectively positioning a multi-electrode esophageal temperature monitoring device in the vasculature with respect to all targeted pulmonary veins; selectively positioning a multi-electrode radiofrequency balloon catheter in the vasculature with respect to all targeted pulmonary veins; selectively positioning a multi-electrode diagnostic catheter in the vasculature with respect to all targeted pulmonary veins; ablating tissue of all targeted pulmonary veins using the multi-electrode radiofrequency balloon catheter; confirming isolation of all targeted pulmonary veins using the multi-electrode diagnostic catheter; confirming existence of an entrance block in all targeted pulmonary veins; achieving a predetermined clinical effectiveness and/ or acute effectiveness of the procedure, based on the confirmed existence of the entrance block, regarding the isolation of all targeted pulmonary veins following the procedure.

In some examples, mapping all targeted pulmonary veins using the diagnostic catheter.

In some examples, exclusion criteria for the plurality of patients comprises at least one of the following: atrial fibrillation secondary to electrolyte imbalance, thyroid disease, or reversible or non-cardiac cause; previous surgical or catheter ablation for atrial fibrillation; anticipated to receive ablation outside all targeted pulmonary veins ostia and CTI region; previously diagnosed with persistent, longstanding atrial fibrillation and/or continuous atrial fibrillation >7 days, or >48 hrs terminated by cardioversion; any percutaneous coronary intervention (PCI) within the past 2 months; valve repair or replacement and presence of a prosthetic valve; any carotid stenting or endarterectomy; coronary artery bypass grafting, cardiac surgery, valvular cardiac surgical or percutaneous procedure within the past 6 months; documented left atrium thrombus on baseline imaging; LA antero posterior diameter greater than 50 mm; any pulmonary vein with a diameter greater than or equal to 26 mm; left ventricular ejection fraction less than 40%; contraindication to anticoagulation; history of blood clotting or bleeding abnormalities; myocardial infarction within the past 2 months; documented thromboembolic event within the past 12 months; rheumatic heart disease; awaiting cardiac transplantation or other cardiac surgery within the next 12 months; unstable angina; acute illness or active systemic infection or sepsis; diagnosed atrial myxoma or interatrial baffle or patch; presence of implanted pacemaker, implantable cardioverter defibrillator, tissue-embedded, or iron-containing metal fragments; significant pulmonary disease or any other disease or malfunction of the lungs or respiratory system that produces chronic symptoms; significant congenital anomaly; pregnancy or lactating; enrollment in an investigational study evaluating another device, biologic, or drug; pulmonary vein stenosis; presence of intramural thrombus, tumor or other abnormality that precludes vascular access, or manipulation of the catheter; presence of an IVC filter; presence of a condition that precludes vascular access; life expectancy or other disease processes likely to limit survival to less than 12 months; contraindication to use of contrast agents for Mill; presence of iron-containing metal fragments in the patient; or unresolved pre-existing neurological deficit.

In some examples, the multi-electrode radiofrequency balloon catheter includes a compliant balloon with a plurality of electrodes configured to deliver RF energy to tissue of all targeted pulmonary veins and sense temperature at each electrode. In some examples, the plurality of electrodes is oriented circularly to circumferentially contact with an ostia of the pulmonary vein. In some examples, the method or use includes using the plurality of electrodes for visualization, stimulation, recording, and ablation. In some examples, each electrode is configured so an amount of power delivered to each electrode is controlled independently. In some examples, the multi-electrode radiofrequency balloon catheter further comprises a proximal handle, a distal tip, and a middle section disposed therebetween. In some examples, the proximal handle is a deflection thumb knob allowing for unidirectional deflection, a balloon advancement mechanism, and a luer fitting for balloon inflation and irrigation. In some examples, the multi-electrode radiofrequency balloon catheter further comprises a high-torque shaft configured to be rotated to facilitate accurate positioning of the catheter tip to a desired; and a unidirectional braided deflectable tip section.

In some examples, the method or use also includes controlling irrigation to the multi-electrode radiofrequency balloon catheter with an irrigation pump.

In some examples, the method or use also includes administering uninterrupted anticoagulation therapy at least 1 month prior to the procedure.

In some examples, if the patient is receiving warfarin/coumadin therapy, the patient must have an international normalized ratio (INR)≥2 for at least 3 weeks prior to the procedure.

In some examples, if the patient is receiving warfarin/coumadin therapy, the patient must be confirmed to have an international normalized ratio (INR)≥2 within 48 hours pre-procedure.

In some examples, the method or use also includes continuing anticoagulation therapy prior to the procedure.

In some examples, the method or use also includes administering a transseptal puncture; confirming an activated clotting time target of ≥350 sec. prior to inserting the multi-electrode radiofrequency balloon catheter into the left atrium and maintaining throughout the procedure; introducing the multi-electrode radiofrequency balloon catheter; introducing of a multi-electrode circular diagnostic catheter; ablating the pulmonary vein with the multi-electrode radiofrequency balloon catheter; determining in real time pulmonary vein isolation with the multi-electrode circular diagnostic catheter; and confirming whether an entrance is blocked in the pulmonary vein.

In some examples, the method or use also includes the multi-electrode circular diagnostic catheter comprises: an elongated body having a longitudinal axis; a distal assembly distal the elongated body, the distal assembly having a helical form comprising a proximal loop and a distal loop, and a shape-memory support member extending through at least the proximal loop, the proximal loop and the distal loop being oriented obliquely at an angle relative to the longitudinal axis of the elongated body; at least one irrigated ablation ring electrode mounted on the proximal loop; a control handle proximal the elongated body; and a contraction wire having a proximal end in the control handle and a distal end anchored in the proximal loop, the control handle including a first control member configured to actuate the contraction wire to contract the proximal loop, wherein the proximal loop has a first flexibility and the distal loop has a second flexibility, and the second flexibility is greater than the first flexibility.

In some examples, a method or use of treating a plurality of patients for paroxysmal atrial fibrillation by applying energy to tissue of a subject's heart proximate to an esophagus, phrenic nerve, or lung, the method or use comprising the steps of achieving at least one of a predetermined clinical effectiveness and acute effectiveness of the procedure based on use of a multi-electrode radiofrequency balloon catheter and a multi-electrode diagnostic catheter in the isolation of the one or more targeted pulmonary veins by positioning an expandable member proximate to the left atrium, the expandable member of the multi-electrode radiofrequency balloon catheter having a longitudinal axis and including a plurality of electrodes disposed about the longitudinal axis, each electrode capable of being energized independently, the plurality of electrodes including a first electrode having a first radiopaque marker and a second electrode having a second radiopaque marker different from the first radiopaque marker; viewing an image of the expandable member as well as the first and second radiopaque markers in the left atrium; determining an orientation of the first and second radiopaque markers with respect to a portion of the left atrium closest to the esophagus, phrenic nerve, or lung, of the subject; moving one of the first and second radiopaque markers to a portion of the left atrium closest to the esophagus, phrenic nerve or lung; energizing one or more electrodes indexed to the one of the radiopaque markers proximate the portion close to the esophagus, phrenic nerve, or lung, at a lower energization setting as compared to other electrodes to create a transmural lesion in the left atrium with little or no effect to adjacent anatomical structures; and electrophysiologically recording and stimulating the atrial region of the tissue proximate to the esophagus, phrenic nerve, or lung using the multi-electrode diagnostic catheter.

In some examples, a multi-electrode RF balloon catheter is also disclosed for the treatment of drug refractory atrial fibrillation in a clinically effective and/or clinically safe manner for a predetermined population size.

In some examples, a clinically effective device is disclosed to treat atrial fibrillation in a group of patients. The device can include an end probe coupled to a tubular member that extends along a longitudinal axis from a proximal portion to a distal portion. The end probe can include a first expandable membrane coupled to the tubular member; a plurality of electrodes disposed generally equiangularly about the longitudinal axis on an outer surface of the first expandable membrane; at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane. The device can achieve a predetermined effectiveness rate of pulmonary vein isolation in the group of patients.

In some examples, a clinically effective device is disclosed to administer a procedure for cardiac electrophysiological ablation of pulmonary veins of the atria and treatment of drug refractory recurrent symptomatic pulmonary atrial fibrillation. The device can include an end probe coupled to a tubular member that extends along a longitudinal axis from a proximal portion to a distal portion. The end probe can include a first expandable membrane coupled to the tubular member; a plurality of electrodes disposed generally equiangularly about the longitudinal axis on an outer surface of the first expandable membrane; at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane so that each of the plurality of electrodes is independently controlled to achieve a predetermined effectiveness rate of pulmonary vein isolation.

In some examples, a clinically effective device is disclosed to administer a procedure for cardiac electrophysiological ablation of pulmonary veins of the atria and treatment of drug refractory recurrent symptomatic pulmonary atrial fibrillation. The device can include an end probe coupled to a tubular member that extends along a longitudinal axis from a proximal portion to a distal portion. The end probe can include a first expandable membrane coupled to the tubular member; a plurality of electrodes disposed generally equiangularly about the longitudinal axis on an outer surface of the first expandable membrane; at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane so that each of the plurality of electrodes is independently controlled to achieve pulmonary vein isolation and at least a 97% safety endpoint within seven (7) days of successful pulmonary vein isolation.

In some examples, a clinically effective device is disclosed to administer a procedure for cardiac electrophysiological ablation of pulmonary veins of the atria and treatment of drug refractory recurrent symptomatic pulmonary atrial fibrillation. The device can include an end probe coupled to a tubular member that extends along a longitudinal axis from a proximal portion to a distal portion. The end probe can include a first expandable membrane coupled to the tubular member; a plurality of electrodes disposed generally equiangularly about the longitudinal axis on an outer surface of the first expandable membrane; at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane so that each of the plurality of electrodes is independently controlled to achieve pulmonary vein isolation and at least a 90% safety endpoint within seven (7) days of successful pulmonary vein isolation.

In some examples, the predetermined effectiveness rate includes complication rates of 10% or less and is defined by existence or non-existence of asymptomatic cerebral embolic lesions at a discharge magnetic resonance imaging (MRI).

In some examples, the predetermined effectiveness rate includes complication rates of approximately 0% and is defined by existence or non-existence of esophageal injury erythema.

In some examples, the predetermined effectiveness rate is approximately 100% and is defined by electrically isolating all targeted pulmonary veins without use of a focal ablation catheter.

In some examples, the predetermined effectiveness rate is defined by a freedom from documented atrial fibrillation, atrial tachycardia, or atypical atrial flutter episodes based on electrocardiographic data through an effectiveness evaluation period. In some examples, the effectiveness evaluation period is approximately one year.

In some examples, the predetermined effectiveness rate is defined by pulmonary vein isolation touch-up by a focal catheter among all targeted pulmonary veins.

In some examples, the predetermined effectiveness rate is defined by using focal catheter ablation for non-PV triggers during the index procedure.

In some examples, the predetermined effectiveness rate comprises a long-term effectiveness rate.

In some examples, the predetermined effectiveness rate is defined by an average number of Radio-Frequency applications per patient and Radio-Frequency time required to isolate all pulmonary veins.

In some examples, the predetermined effectiveness rate is defined by an average number of Radio-Frequency applications per vein and Radio-Frequency time required to isolate common pulmonary veins.

In some examples, the predetermined effectiveness rate is defined by an average number of Radio-Frequency applications per patient and Radio-Frequency time required to isolate common pulmonary veins.

In some examples, the predetermined effectiveness rate is defined by determining incidence of complication rates being 10% or less of post-ablation symptomatic and asymptomatic cerebral emboli as compared to pre-ablation.

In some examples, the predetermined effectiveness rate is defined by evaluating a presence of emboli-associated neurological deficits by at least one of NIHSS and mRS assessments.

In some examples, the end probe is configured for use in catheter-based cardiac electrophysiological mapping of the atria.

In some examples, the end probe is configured for cardiac ablation.

In some examples, the end probe comprises: the plurality of electrodes bonded to the first expandable membrane and configured to deliver Radio-Frequency energy to tissue of the pulmonary vein and sense temperature at each electrode.

In some examples, the plurality of electrodes is oriented circularly to circumferentially contact with an ostia of the pulmonary vein.

In some examples, the device is further configured for using the plurality of electrodes for visualization, stimulation, recording, and ablation.

In some examples, each electrode is configured so an amount of power delivered to each electrode is controlled independently.

In some examples, the end probe further comprises a proximal handle, a distal tip, and a middle section disposed therebetween.

In some examples, the proximal handle is a deflection thumb knob allowing for unidirectional deflection, a balloon advancement mechanism, and a luer fitting for balloon inflation and irrigation.

In some examples, the end probe further includes a high-torque shaft configured to be rotated to facilitate accurate positioning of the catheter tip to a desired; and a unidirectional braided deflectable tip section.

In some examples, the end probe further includes a first substrate disposed on the membrane, the first substrate including a first radiopaque marker of a first form disposed thereon; and a second substrate disposed on the membrane, the second substrate including a second radiopaque marker of a second form disposed thereon, the second form being different from the first form.

In some examples, the device further includes an irrigation pump to provide irrigation fluid to the first expandable membrane and out of the first expandable membrane.

In some examples, the effectiveness evaluation period is at least 91 days following a delivery of the end probe to the pulmonary vein; and ablation of tissue proximate the pulmonary vein with the end probe.

In some examples, the effectiveness evaluation period is less than or equal to one year following a delivery of the end probe to the pulmonary vein; and ablation of tissue proximate the pulmonary vein with the end probe.

In some examples, the predetermined success rate is 60% for a population size of at least 40 patients.

In some examples, a population size for the predetermined success rate is at least 300 patients, 200 patients, 100 patients, or 50 patients.

In some examples, the predetermined success rate is at least 60%.

In some examples, the predetermined success rate is determined by evaluation of the patient 7 days following a delivery of the end probe to the pulmonary vein and ablation of tissue proximate the pulmonary vein with the end probe.

In some examples, the predetermined success rate is determined by evaluation of the patient 1 month following a delivery of the end probe to the pulmonary vein; and ablation of tissue proximate the pulmonary vein with the end probe.

In some examples, the predetermined success rate is determined by evaluation of the patient 6 months following a delivery of the end probe to the pulmonary vein; and ablation of tissue proximate the pulmonary vein with the end probe.

In some examples, the predetermined success rate is determined by evaluation of the patient 12 months following a delivery of the end probe to the pulmonary vein; and ablation of tissue proximate the pulmonary vein with the end probe.

In some examples, the predetermined success rate further includes confirmation of an entrance block in the pulmonary vein after at least one of adenosine and isoproterenol challenge.

In some examples, the patient suffering at least one of the following events is deemed as unsuccessful pulmonary vein isolation, including: device or procedure related death; atrio-esophageal fistula, myocardial infarction; cardiac Tamponade/Perforation; thromboembolism; stroke/Cerebrovascular Accident (CVA); transient Ischemic Attach (TIA); phrenic Nerve Paralysis, Pulmonary Vein Stenosis; pericarditis; pulmonary Edema; major Vascular Access Complication/Bleeding; and hospitalization (initial or prolonged).

In some examples, the patient suffering at least one of the following events is deemed as unsuccessful pulmonary vein isolation, whereby those events can include acute procedural failure; repeat ablation or surgical treatment for AF/AT/Atypical (left-side) AFL after the blanking period (after day 90 post index procedure); DC cardioversion for AF/AT/Atypical (left-side) AFL, continuous AF/AT/AFL on a standard 12-lead ECG even if the recording is less than 30 seconds in duration (after day 90 post index procedure); a new Class I and/or Class III AAD is prescribed for AF during effectiveness evaluation period (day 91-365 post index procedure) or prescribed during the blanking period and continued past 90 days; a previously failed Class I and/or Class III AAD (failed at or before screening) is taken for AF at a greater dose than the highest ineffective historical dose during the effectiveness evaluation period; and amiodarone is prescribed post procedure.

In some examples, the safety endpoint is defined by a patient suffering a primary adverse event.

In some examples, at least one risk factor for the patient is selected at least three (3) symptomatic episodes of atrial fibrillation that last lasting ≥1 minute within six (6) months before the device; at least one (1) atrial fibrillation episode electrocardiographically documented within twelve (12) months prior to enrollment (e.g., electrocardiogram (ECG), Holter monitor, telemetry strip, etc.); failing at least one (1) Class I or Class III AAD as evidenced by recurrent symptomatic atrial fibrillation or intolerable side effects to the AAD; younger than 18 or older than 75 years; secondary to electrolyte imbalance; thyroid disease; reversible or non-cardiac cause; and previous surgical or catheter ablation for atrial fibrillation.

In some examples, for purposes of calculating the effectiveness rate, the patient has at least one of the following risk factors: patients known to require ablation outside the PV ostia and CTI region; previously diagnosed with persistent or long-standing persistent atrial fibrillation and/or continuous atrial fibrillation 7 days following the device procedure; any percutaneous coronary intervention within the past 2 months; repair or replacement or presence of a prosthetic valve; any carotid stenting or endarterectomy within the past 6 months; coronary artery bypass grafting, cardiac surgery or valvular cardiac surgical procedure within the past 6 months; documented left atrium thrombus within 1 day prior to the device procedure; left atrium antero posterior diameter >50 mm; left Ventricular Ejection Fraction <40%; contraindication to anticoagulation; history of blood clotting or bleeding abnormalities; myocardial infarction within the past 2 months; documented thromboembolic event (including transient ischemic attack) within the past 12 months; Rheumatic Heart Disease; uncontrolled heart failure or New York Heart Association (NYHA) function class III or IV; awaiting cardiac transplantation or other cardiac surgery within the next 12 months; unstable angina; acute illness or active systemic infection or sepsis; diagnosed atrial myxoma or presence of an interatrial baffle or patch; presence of implanted pacemaker or implantable cardioverter defibrillator (ICD); significant pulmonary disease or any other disease or malfunction of the lungs or respiratory system that produces chronic symptoms; significant congenital anomaly; women who are pregnant; enrollment in an investigational study evaluating another device, biologic, or drug; known pulmonary vein stenosis; presence of intramural thrombus, tumor or other abnormality that precludes vascular access, or manipulation of the catheter; presence of an inferior vena cava filter; presence of a condition that precludes vascular access; life expectancy or other disease processes likely to limit survival to less than 12 months; presenting contra-indication for the devices; and patient on amiodarone at any time during the past 3 months prior to enrollment.

In some examples, if the patient is receiving warfarin/coumadin therapy, the patient must have an international normalized ratio ≥2 for at least 3 weeks prior to the procedure.

In some examples, if the patient is receiving warfarin/coumadin therapy, the patient must be confirmed to have an international normalized ratio ≥2 within 48 hours pre-procedure.

In some examples, wherein anticoagulation therapy is provided prior to the procedure.

In some examples, wherein an activated clotting time of 350-400 seconds is targeted prior to insertion of the catheter and throughout the procedure.

In some examples, wherein an activated clotting time levels are checked every 15-30 minutes during the procedure to ensure an activated clotting time target of 350-400 seconds.

In some examples, wherein the multi-electrode circular diagnostic catheter includes an elongated body having a longitudinal axis and a distal assembly distal the elongated body. The distal assembly can have a helical form comprising a proximal loop, a distal loop, and a shape-memory support member extending through at least the proximal loop. The proximal loop and the distal loop can be oriented obliquely at an angle relative to the longitudinal axis of the elongated body; at least one irrigated ablation ring electrode mounted on the proximal loop; a control handle proximal the elongated body; and a contraction wire having a proximal end in the control handle and a distal end anchored in the proximal loop, the control handle including a first control member configured to actuate the contraction wire to contract the proximal loop. The proximal loop can have a first flexibility and the distal loop has a second flexibility, and the second flexibility can be greater than the first flexibility.

In some examples, a multi-electrode RF balloon catheter is disclosed for the treatment of drug refractory atrial fibrillation in a clinically effective and/or clinically safe manner for a predetermined population size.

In some examples, a method or use is disclosed for administering a procedure for treating atrial fibrillation. The method or use can include delivering a multi-electrode radiofrequency balloon catheter to one or more targeted pulmonary veins; ablating tissue of the pulmonary vein using the multi-electrode radiofrequency balloon catheter; and achieving a predetermined effectiveness rate of pulmonary vein isolation.

In some examples, the multi-electrode radiofrequency balloon catheter is configured for use in catheter-based cardiac electrophysiological mapping of the atria.

In some examples, the multi-electrode radiofrequency balloon catheter is configured for cardiac ablation.

In some examples, the multi-electrode radiofrequency balloon catheter has a compliant balloon with a plurality of electrodes bonded configured to deliver RF energy to tissue of the pulmonary vein and sense temperature at each electrode.

In some examples, the plurality of electrodes is oriented circularly to circumferentially contact with an ostia of the pulmonary vein.

In some examples, the method or use includes using the plurality of electrodes for visualization, stimulation, recording, and ablation.

In some examples, each electrode is configured so an amount of power delivered to each electrode is controlled independently.

In some examples, the balloon has a membrane, the balloon having a distal end and a proximal end defining a longitudinal axis, the multi-electrode radiofrequency balloon catheter includes a first substrate disposed on the membrane, the first substrate including a first radiopaque marker of a first form disposed thereon. A second substrate can be disposed on the membrane, the second substrate including a second radiopaque marker of a second form disposed thereon, the second form being different from the first form.

In some examples, the method or use includes controlling irrigation to the multi-electrode radiofrequency balloon catheter with an irrigation pump.

In some examples, the effectiveness evaluation period is at least 91 days following the delivering the multi-electrode radiofrequency balloon catheter to the pulmonary vein and the ablating tissue of the pulmonary vein using the multi-electrode radiofrequency balloon catheter.

In some examples, the effectiveness evaluation period is less than or equal to one year following the delivering the multi-electrode radiofrequency balloon catheter to the pulmonary vein and the ablating tissue of the pulmonary vein using the multi-electrode radiofrequency balloon catheter.

In some examples, a method or use is disclosed for administering a procedure for treating atrial fibrillation. The method or use can include delivering a multi-electrode radiofrequency balloon catheter to a pulmonary vein, ablating tissue of the pulmonary vein using the multi-electrode radiofrequency balloon catheter and achieving a predetermined success rate of pulmonary vein isolation.

In some examples, the predetermined success rate is determined by evaluating the patient 7 days following the delivering the multi-electrode radiofrequency balloon catheter to the pulmonary vein; and the ablating tissue of the pulmonary vein using the multi-electrode radiofrequency balloon catheter.

In some examples, the predetermined success rate is determined by evaluating the patient 1 month, 6 months and/or 12 months following the delivering the multi-electrode radiofrequency balloon catheter to the pulmonary vein, and the ablating tissue of the pulmonary vein using the multi-electrode radiofrequency balloon catheter.

In some examples, the success rate further includes confirming an entrance block in the pulmonary vein after at least one of adenosine and isoproterenol challenge.

In some examples, the delivering step further comprises using a focal catheter.

In some examples, the patient suffering at least one of the following events is deemed as having an unsuccessful pulmonary vein isolation, including device or procedure related death, atrio-esophageal fistula, myocardial infarction, cardiac Tamponade/Perforation, thromboembolism, stroke/Cerebrovascular Accident (CVA), transient Ischemic Attach (TIA), phrenic Nerve Paralysis, Pulmonary Vein Stenosis, pericarditis, pulmonary Edema, major Vascular Access Complication/Bleeding, and hospitalization (initial or prolonged).

In some examples, the patient suffering at least one of the following events is deemed as having an unsuccessful pulmonary vein isolation, having acute procedural failure, repeat ablation or surgical treatment for AF/atrial tachycardia (AT)/Atypical (left-side) atrial flutter (AFL) after the blanking period (after day 90 post index procedure), direct current (DC) cardioversion for AF/AT/Atypical (left-side) AFL, continuous AF/AT/AFL on a standard 12-lead ECG even if the recording is less than 30 seconds in duration (after day 90 post index procedure), a new Class I and/or Class III antiarrhythmic drugs (AAD) is prescribed for AF during effectiveness evaluation period (day 91-365 post index procedure) or prescribed during the blanking period and continued past 90 days, a previously failed Class I and/or Class III AAD (failed at or before screening) is taken for AF at a greater dose than the highest ineffective historical dose during the effectiveness evaluation period, and amiodarone is prescribed post procedure.

In some examples, a method or use is disclosed for administering a procedure for cardiac electrophysiological ablation of pulmonary veins of the atria and treating drug refractory recurrent symptomatic pulmonary atrial fibrillation. The method or use can include delivering a multi-electrode radiofrequency balloon catheter to a pulmonary vein; ablating tissue of the pulmonary vein using the multi-electrode radiofrequency balloon catheter; and achieving a predetermined effectiveness rate of pulmonary vein isolation.

In some examples, a method or use is disclosed for administering a procedure for cardiac electrophysiological ablation of pulmonary veins of the atria and treating drug refractory recurrent symptomatic pulmonary atrial fibrillation. The method or use can include delivering a multi-electrode radiofrequency balloon catheter to a pulmonary vein; ablating tissue of the pulmonary vein using the multi-electrode radiofrequency balloon catheter; and achieving pulmonary vein isolation and at least a 97% safety endpoint within seven (7) days of successful pulmonary vein isolation.

In some examples, a method or use is disclosed for administering a procedure for cardiac electrophysiological ablation of pulmonary veins of the atria and treating drug refractory recurrent symptomatic pulmonary atrial fibrillation. The method or use includes delivering a multi-electrode radiofrequency balloon catheter to a pulmonary vein, ablating tissue of the pulmonary vein using the multi-electrode radiofrequency balloon catheter, and achieving pulmonary vein isolation and at least a 90% safety endpoint within seven (7) days of successful pulmonary vein isolation.

In some examples, the safety endpoint is defined by a patient suffering a primary adverse event.

In some examples, at least one risk factor for the patient is selected from the group of: at least three (3) symptomatic episodes of atrial fibrillation that last lasting ≥1 minute within six (6) months before the method or use, at least one (1) atrial fibrillation episode electrocardiographically documented within twelve (12) months prior to enrollment. Electrocardiographic documentation can include, but is not limited to, electrocardiogram (ECG), Holter monitor, or telemetry strip, failing at least one (1) Class I or Class III AAD as evidenced by recurrent symptomatic atrial fibrillation or intolerable side effects to the AAD, age 18-75 years, secondary to electrolyte imbalance, thyroid disease, reversible or non-cardiac cause, and previous surgical or catheter ablation for atrial fibrillation.

In some examples, the patient has at least one risk factor selected from the group of: patients known to require ablation outside the PV ostia and CTI region, previously diagnosed with persistent or long-standing persistent atrial fibrillation and/or continuous atrial fibrillation 7 days following the method or use procedure, any percutaneous coronary intervention within the past 2 months, repair or replacement or presence of a prosthetic valve, and any carotid stenting or endarterectomy within the past 6 months. Other risk factors include coronary artery bypass grafting, cardiac surgery or valvular cardiac surgical procedure within the past 6 months, documented left atrium thrombus within 1 day prior to the method or use procedure, left atrium antero posterior diameter >50 mm, Left Ventricular Ejection Fraction <40%, contraindication to anticoagulation, history of blood clotting or bleeding abnormalities, myocardial infarction within the past 2 months, and documented thromboembolic event (including transient ischemic attack) within the past 12 months. Additional risk factors include Rheumatic Heart Disease, uncontrolled heart failure or New York Heart Association (NYHA) function class III or IV, awaiting cardiac transplantation or other cardiac surgery within the next 12 months, unstable angina, acute illness or active systemic infection or sepsis, diagnosed atrial myxoma or presence of an interatrial baffle or patch, and the presence of implanted pacemaker or implantable cardioverter defibrillator (ICD). Further risk factors include significant pulmonary disease or any other disease or malfunction of the lungs or respiratory system that produces chronic symptoms, significant congenital anomaly, women who are pregnant, enrollment in an investigational study evaluating another device, biologic, or drug, known pulmonary vein stenosis, presence of intramural thrombus, tumor or other abnormality that precludes vascular access, or manipulation of the catheter, presence of an inferior vena cava filter, presence of a condition that precludes vascular access, life expectancy or other disease processes likely to limit survival to less than 12 months, presenting contra-indication for the devices, and patient on amiodarone at any time during the past 3 months prior to enrollment.

In some examples, the method or use includes targeting an activated clotting time of 350-400 seconds prior to inserting the catheter and throughout the procedure.

In some examples, the method or use includes checking an activated clotting time levels every 15-30 minutes during the procedure to ensure an activated clotting time target of 350-400 seconds.

In some examples, the method or use includes administering a transseptal puncture, confirming an activated clotting time target of ≥350 sec. prior to inserting the multi-electrode radiofrequency balloon catheter into the left atrium and maintaining throughout the procedure, introducing the multi-electrode radiofrequency balloon catheter, introducing of a multi-electrode circular diagnostic catheter, ablating the pulmonary vein with the multi-electrode radiofrequency balloon catheter, determining in real time pulmonary vein isolation with the multi-electrode circular diagnostic catheter, and confirming whether an entrance is blocked in the pulmonary vein.

In some examples, a method or use is disclosed for pulmonary vein isolation by applying energy to tissue of a subject's heart proximate to an esophagus, phrenic nerve, or lung. The method or use includes achieving a predetermined effectiveness rate according to any of the above by positioning an expandable member proximate to the left atrium, the expandable member having a longitudinal axis and including a plurality of electrodes disposed about the longitudinal axis, each electrode capable of being energized independently, the plurality of electrodes including a first electrode having a first radiopaque marker and a second electrode having a second radiopaque marker different from the first radiopaque marker, viewing an image of the expandable member as well as the first and second radiopaque markers in the left atrium, determining an orientation of the first and second radiopaque markers with respect to a portion of the left atrium closest to the esophagus, phrenic nerve, or lung, of the subject, moving one of the first and second radiopaque markers to a portion of the left atrium closest to the esophagus, phrenic nerve or lung, and energizing one or more electrodes indexed to the one of the radiopaque markers proximate the portion close to the esophagus, phrenic nerve, or lung, at a lower energization setting as compared to other electrodes to create a transmural lesion in the left atrium with little or no effect to adjacent anatomical structures.

In some examples, use of an independently controlled multi-electrode radiofrequency balloon catheter is disclosed to treat paroxysmal atrial fibrillation, comprising delivering a multi-electrode radiofrequency balloon catheter having a plurality of independently controllable electrodes for radiofrequency ablation and a multi-electrode diagnostic catheter to one or more targeted pulmonary veins; ablating tissue of the one or more targeted pulmonary veins with one or more of the plurality of the electrodes independently controlled multi-electrode radiofrequency balloon catheter; diagnosing the one or more targeted pulmonary veins using the multi-electrode diagnostic catheter; and achieving at least one of a predetermined clinical effectiveness and acute effectiveness of the multi-electrode radiofrequency balloon catheter and the multi-electrode diagnostic catheter in the isolation of the one or more targeted pulmonary veins, during and approximately 3 months after the ablating step.

In some examples, acute effectiveness is defined by confirming if there is an entrance block in all targeted pulmonary veins after adenosine and/or isoproterenol challenge.

In some examples, the use includes determining the acute effectiveness determined at approximately 3 months after the ablating step; and generating an estimated acute effectiveness at approximately 12 months after the ablating step based on the acute effectiveness determined at approximately 3 months.

In some examples, the estimated acute effectiveness at approximately 12 months is substantially similar to the acute effectiveness determined at approximately 3 months.

In some examples, the acute effectiveness is further defined by success greater than 90% for the plurality of patients.

In some examples, the acute effectiveness is further defined by success greater than 95% for the plurality of patients.

In some examples, a Type-1 error rate for power the acute effectiveness and the clinical effectiveness of all targeted veins are controlled at approximately a 5% level, the use includes determining whether the ablating is clinically successful for the plurality of patients if both the acute effectiveness and the clinical effectiveness indications are controlled at approximately the 5% level.

In some examples, the acute effectiveness is at least 80% for the plurality of patients being at least 80 patients.

In some examples, the acute effectiveness is at least 80% for the plurality of patients being at least 130 patients.

In some examples, the acute effectiveness is at least 80% for the plurality of patients being at least 180 patients.

In some examples, the acute effectiveness is at least 80% for the plurality of patients being at least 230 patients.

In some examples, the acute effectiveness is further defined by confirming if there is an entrance block in all targeted pulmonary veins after adenosine and/or isoproterenol challenge using a focal ablation catheter.

In some examples, the acute effectiveness is further defined by confirming if there is an entrance block in all targeted pulmonary veins after adenosine and/or isoproterenol challenge without using a focal ablation catheter.

In some examples, the ablating is administered on the plurality of patients diagnosed with symptomatic paroxysmal atrial fibrillation.

In some examples, the step of diagnosing further comprises an electrophysiological mapping of the heart.

In some examples, the multi-electrode diagnostic catheter further comprises a high torque shaft with a halo-shaped tip section containing a plurality of pairs of electrodes visible under fluoroscopy.

In some examples, the predetermined acute effectiveness is defined by ulceration being absent in the plurality of patients after the ablating.

In some examples, the predetermined acute effectiveness is defined by a complication rate of approximately 13% or fewer of the plurality of patients experiencing esophageal erythema after the ablating.

In some examples, the predetermined acute effectiveness is defined by a complication rate of approximately 25% or fewer of the plurality of patients experiencing new asymptomatic cerebral embolic lesions after the ablating.

In some examples, the predetermined acute effectiveness is defined by a complication rate of approximately 20% or fewer of the plurality of patients experiencing new asymptomatic cerebral embolic lesions after the ablating.

In some examples, the predetermined acute effectiveness is defined by a complication rate of approximately 5-9% or fewer of the plurality of patients experiencing a primary adverse event by approximately 7 or more days after the ablating.

In some examples, inclusion criteria for the plurality of patients includes a diagnosis with symptomatic paroxysmal atrial fibrillation; and a patient capability to comply with uninterrupted per-protocol anticoagulation requirements.

In some examples, the predetermined acute effectiveness is defined by a total procedure time.

In some examples, the predetermined acute effectiveness is defined by a total ablation time.

In some examples, the predetermined acute effectiveness is defined by a total RF application time.

In some examples, the predetermined acute effectiveness is defined by a total dwell time of the multi-electrode radiofrequency balloon catheter.

In some examples, the predetermined acute effectiveness is defined by a total time to isolate all targeted pulmonary veins.

In some examples, the predetermined acute effectiveness is defined by a number and a total time of applications by the multi-electrode radiofrequency balloon catheter per location of all targeted pulmonary veins.

In some examples, the predetermined acute effectiveness is defined by a number and a total time of applications by the multi-electrode radiofrequency balloon catheter per patient.

In some examples, the predetermined acute effectiveness is defined by a number and a total time of applications by the multi-electrode radiofrequency balloon catheter per targeted vein.

In some examples, the multi-electrode radiofrequency balloon catheter comprises a compliant balloon with a plurality of electrodes bonded configured to deliver RF energy to tissue of the pulmonary vein and sense temperature at each electrode.

In some examples, clinical effectiveness is defined by an incidence of early onset of one or more adverse events within a predetermined time of the use being implemented.

In some examples, the predetermined time is at least 7 days.

In some examples, the one or more adverse events comprise: death, atrio-esophageal fistula, myocardial infarction, cardiac tamponade/perforation, thromboembolism, stroke, TIA (Transient Ischemic Attack), phrenic nerve paralysis, pulmonary vein stenosis, and the major vascular access bleeding.

In some examples, the one or more adverse events comprise: incidence of individual adverse events from a primary composite; incidence of serious adverse device effect; incidence of serious adverse events within 7 days, at least 730 days, and at least 30 days following the ablating; incidence of non-serious adverse events; incidence of pre- and post-ablation asymptomatic and symptomatic cerebral emboli as determined by MRI evaluation; and frequency, anatomic location, and size (diameter and volume) of cerebral emboli by MRI evaluations at baseline, post-ablation and during follow-up.

In some examples, the one or more adverse events for approximately 5-9% of the plurality of patients, the one or more adverse events including NIHSS (National Institute of Health Stroke Scale) scores at baseline, post-ablation and during follow-up;

a summary of MoCA (Montreal Cognitive Assessment) and mRS (Modified Ranking Scale) scores at baseline, 1 month and during further follow-up; a rate of hospitalization for cardiovascular events; a percentage (%) of pulmonary vein isolation touch-up by focal catheter among the one or more targeted veins;

a percentage (%) of subjects with use of focal catheter ablations for non-PV triggers;

a percentage (%) of subjects with freedom from documented symptomatic atrial fibrillation (AF), atrial tachycardia (AT), or atypical (left side) atrial flutter (AFL) episodes (episodes >30 seconds on arrhythmia monitoring device from day 91 to 180);

a percentage (%) of subjects with freedom from documented atrial fibrillation (AF), atrial tachycardia (AT), or atypical (left side) atrial flutter (AFL);

one or more episodes that endure for 30 or more seconds on an arrhythmia monitoring device from day 91 to 180 following the ablating; and one or more procedural parameters including total procedure and ablation time, balloon dwell time, RF application time, a number of RF applications, fluoroscopy time and dose.

In some examples, wherein the acute safety rate includes complication rates of 10% or less and is defined by incidence of asymptomatic cerebral embolic lesions at a discharge magnetic resonance imaging (MRI).

In some examples, the acute effectiveness rate is 100% and is defined by electrically isolating all targeted pulmonary veins without use of a focal ablation catheter.

In some examples, the acute effectiveness rate is defined by a freedom from documented atrial fibrillation, atrial tachycardia, or atypical atrial flutter episodes based on electrocardiographic data through an effectiveness evaluation period (1 year).

In some examples, the acute effectiveness rate is defined by pulmonary vein isolation touch-up by a focal catheter among all targeted pulmonary veins.

In some examples, the predetermined clinical effectiveness rate is defined by 10% or less complication rates related to incidence of post-ablation symptomatic and asymptomatic cerebral emboli as compared to pre-ablation.

In some examples, the multi-electrode diagnostic catheter is configured for electrophysiological recording and stimulation of the atrial region of the heart and is used in conjunction with the multi-electrode radiofrequency balloon catheter.

In some examples, use of an independently controlled multi-electrode radiofrequency balloon catheter is disclosed to treat a plurality of patients for paroxysmal atrial fibrillation, including delivering a multi-electrode radiofrequency balloon catheter having a plurality of independently controllable electrodes for radiofrequency ablation and a multi-electrode diagnostic catheter to one or more targeted pulmonary veins; and ablating tissue of one or more targeted pulmonary veins with one or more of the plurality of the electrodes independently controlled multi-electrode radiofrequency balloon catheter; diagnosing all targeted pulmonary veins using the multi-electrode diagnostic catheter; and achieving a predetermined rate of adverse events based on use of the multi-electrode radiofrequency balloon catheter and the multi-electrode diagnostic catheter in the isolation of all targeted pulmonary veins, during and approximately 6 months after use.

In some examples, use of an independently controlled multi-electrode radiofrequency balloon catheter is disclosed to treat a plurality of patients for paroxysmal atrial fibrillation, including evaluating a number and size of all targeted pulmonary veins and anatomy of the left atrial; puncturing the transseptal; selectively positioning a multi-electrode esophageal temperature monitoring device in the vasculature with respect to all targeted pulmonary veins; selectively positioning a multi-electrode radiofrequency balloon catheter in the vasculature with respect to all targeted pulmonary veins, the multi-electrode radiofrequency balloon catheter having a plurality of independently controllable electrodes for radiofrequency ablation; selectively positioning a multielectrode diagnostic catheter in the vasculature with respect to all targeted pulmonary veins; ablating tissue of all targeted pulmonary veins with one or more of the plurality of the electrodes independently controlled multi-electrode radiofrequency balloon catheter; confirming isolation of all targeted pulmonary veins using the multi-electrode diagnostic catheter; confirming existence of an entrance block in all targeted pulmonary veins; achieving a predetermined clinical effectiveness and/or acute effectiveness of the method or use, based on the confirmed existence of the entrance block, regarding the isolation of all targeted pulmonary veins following the method or use.

In some examples, use includes mapping all targeted pulmonary veins using the diagnostic catheter.

In some examples, exclusion criteria for the plurality of patients comprises at least one of the following:
- atrial fibrillation secondary to electrolyte imbalance, thyroid disease, or reversible or non-cardiac cause;
- previous surgical or catheter ablation for atrial fibrillation;
- anticipated to receive ablation outside all targeted pulmonary veins ostia and CTI region;
- previously diagnosed with persistent, longstanding atrial fibrillation and/or continuous atrial fibrillation >7 days, or >48 hrs terminated by cardioversion;
- any percutaneous coronary intervention (PCI) within the past 2 months;
- valve repair or replacement and presence of a prosthetic valve;
- any carotid stenting or endarterectomy;
- coronary artery bypass grafting, cardiac surgery, valvular cardiac surgical or percutaneous procedure within the past 6 months;
- documented left atrium thrombus on baseline imaging;
- LA antero posterior diameter greater than 50 mm;
- any pulmonary vein with a diameter greater than or equal to 26 mm;
- left ventricular ejection fraction less than 40%;
- contraindication to anticoagulation;
- history of blood clotting or bleeding abnormalities;
- myocardial infarction within the past 2 months;
- documented thromboembolic event within the past 12 months;
- rheumatic heart disease;
- awaiting cardiac transplantation or other cardiac surgery within the next 12 months;
- unstable angina;
- acute illness or active systemic infection or sepsis;
- diagnosed atrial myxoma or interatrial baffle or patch;
- presence of implanted pacemaker, implantable cardioverter defibrillator, tissue-embedded, or iron-containing metal fragments;
- significant pulmonary disease or any other disease or malfunction of the lungs or respiratory system that produces chronic symptoms;
- significant congenital anomaly;
- pregnancy or lactating;
- enrollment in an investigational study evaluating another device, biologic, or drug;
- pulmonary vein stenosis;
- presence of intramural thrombus, tumor or other abnormality that precludes vascular access, or manipulation of the catheter;
- presence of an IVC filter;
- presence of a condition that precludes vascular access;
- life expectancy or other disease processes likely to limit survival to less than 12 months;
- contraindication to use of contrast agents for MII;
- presence of iron-containing metal fragments in the patient; or
- unresolved pre-existing neurological deficit.

In some examples, the multi-electrode radiofrequency balloon catheter includes a compliant balloon with a plurality of electrodes configured to deliver RF energy to tissue of all targeted pulmonary veins and sense temperature at each electrode.

In some examples, the plurality of electrodes is oriented circularly to circumferentially contact with an ostia of the pulmonary vein.

In some examples, the use includes using the plurality of electrodes for visualization, stimulation, recording, and ablation.

In some examples, each electrode is configured so an amount of power delivered to each electrode is controlled independently.

In some examples, the multi-electrode radiofrequency balloon catheter further includes a proximal handle, a distal tip, and a middle section disposed therebetween.

In some examples, the proximal handle is a deflection thumb knob allowing for unidirectional deflection, a balloon advancement mechanism, and a luer fitting for balloon inflation and irrigation.

In some examples, the multi-electrode radiofrequency balloon catheter includes a high-torque shaft configured to be rotated to facilitate accurate positioning of the catheter tip to a desired; and a unidirectional braided deflectable tip section.

In some examples, use includes controlling irrigation to the multi-electrode radiofrequency balloon catheter with an irrigation pump.

In some examples, use includes administering uninterrupted anticoagulation therapy at least 1 month prior to the procedure.

In some examples, if the patient is receiving warfarin/coumadin therapy, the patient must have an international normalized ratio (INR)≥2 for at least 3 weeks prior to the procedure.

In some examples, if the patient is receiving warfarin/coumadin therapy, the patient must be confirmed to have an international normalized ratio (INR)≥2 within 48 hours pre-procedure.

In some examples, use includes continuing anticoagulation therapy prior to the procedure.

In some examples, use includes administering a transseptal puncture; confirming an activated clotting time target of ≥350 sec. prior to inserting the multi-electrode radiofrequency balloon catheter into the left atrium and maintaining throughout the procedure; introducing the multi-electrode radiofrequency balloon catheter; introducing of a multi-electrode circular diagnostic catheter; ablating the pulmonary vein with the multi-electrode radiofrequency balloon catheter; determining in real time pulmonary vein isolation with the multi-electrode circular diagnostic catheter; and confirming whether an entrance is blocked in the pulmonary vein.

In some examples, wherein the multi-electrode circular diagnostic catheter includes an elongated body having a longitudinal axis; a distal assembly distal the elongated body, the distal assembly having a helical form comprising a proximal loop and a distal loop, and a shape-memory support member extending through at least the proximal loop, the proximal loop and the distal loop being oriented obliquely at an angle relative to the longitudinal axis of the elongated body; at least one irrigated ablation ring electrode mounted on the proximal loop; a control handle proximal the elongated body; and a contraction wire having a proximal end in the control handle and a distal end anchored in the proximal loop, the control handle including a first control member configured to actuate the contraction wire to contract the proximal loop, wherein the proximal loop has a first flexibility and the distal loop has a second flexibility, and the second flexibility is greater than the first flexibility.

In some examples, use of an independently controlled multi-electrode radiofrequency balloon catheter is disclosed to treat a plurality of patients for paroxysmal atrial fibrillation by applying energy to tissue of a subject's heart proximate to an esophagus, phrenic nerve, or lung, including achieving at least one of a predetermined clinical effectiveness and acute effectiveness of the procedure based on use of the multi-electrode radiofrequency balloon catheter and a multi-electrode diagnostic catheter in the isolation of the one or more targeted pulmonary veins by positioning an expandable member proximate to the left atrium, the expandable member of the multi-electrode radiofrequency balloon catheter having a longitudinal axis and including a plurality of electrodes disposed about the longitudinal axis, each electrode capable of being energized independently, the plurality of electrodes including a first electrode having a first radiopaque marker and a second electrode having a second radiopaque marker different from the first radiopaque marker; viewing an image of the expandable member as well as the first and second radiopaque markers in the left atrium; determining an orientation of the first and second radiopaque markers with respect to a portion of the left atrium closest to the esophagus, phrenic nerve, or lung, of the subject; moving one of the first and second radiopaque markers to a portion of the left atrium closest to the esophagus, phrenic nerve or lung; energizing one or more electrodes indexed to the one of the radiopaque markers proximate the portion close to the esophagus, phrenic nerve, or lung, at a lower energization setting as compared to other electrodes to create a transmural lesion in the left atrium with little or no effect to adjacent anatomical structures; and electrophysiologically recording and stimulating the atrial region of the tissue proximate to the esophagus, phrenic nerve, or lung using the multi-electrode diagnostic catheter.

In some examples, use of an independently controlled multi-electrode radiofrequency balloon catheter is disclosed for a procedure for atrial fibrillation, including delivering a multi-electrode radiofrequency balloon catheter to one or more targeted pulmonary veins; ablating tissue of the pulmonary vein using the multi-electrode radiofrequency balloon catheter; and achieving a predetermined effectiveness rate of pulmonary vein isolation.

In some examples, the predetermined effectiveness rate includes complication rates of 10% or less and is defined by existence of asymptomatic cerebral embolic lesions at a discharge magnetic resonance imaging (MRI).

In some examples, the predetermined effectiveness rate is defined by a freedom from documented atrial fibrillation, atrial tachycardia, or atypical atrial flutter episodes based on electrocardiographic data through an effectiveness evaluation period.

In some examples, the effectiveness evaluation period is approximately one year.

In some examples, the predetermined effectiveness rate is defined by pulmonary vein isolation touch-up by a focal catheter among all targeted pulmonary veins.

In some examples, the predetermined effectiveness rate is defined by using focal catheter ablation for non-PV triggers during the index procedure.

In some examples, the predetermined effectiveness rate comprises a long term effectiveness rate.

In some examples, the predetermined effectiveness rate is defined by an average number of RF applications per patient and RF time required to isolate all pulmonary veins.

In some examples, the predetermined effectiveness rate is defined by an average number of RF applications per vein and RF time required to isolate common pulmonary veins.

In some examples, the predetermined effectiveness rate is defined by an average number of RF applications per patient and RF time required to isolate common pulmonary veins.

In some examples, the predetermined effectiveness rate is defined by determining incidence of complication rates being 10% or less of post-ablation symptomatic and asymptomatic cerebral emboli as compared to pre-ablation.

In some examples, the predetermined effectiveness rate is defined by evaluating a presence of emboli-associated neurological deficits by at least one of NIHSS and mRS assessments.

In some examples, the multi-electrode radiofrequency balloon catheter is configured for use in catheter-based cardiac electrophysiological mapping of the atria.

In some examples, the multi-electrode radiofrequency balloon catheter is configured for cardiac ablation.

In some examples, the multi-electrode radiofrequency balloon catheter comprises:

a compliant balloon with a plurality of electrodes bonded configured to deliver RF energy to tissue of the pulmonary vein and sense temperature at each electrode.

In some examples, the plurality of electrodes is oriented circularly to circumferentially contact with an ostia of the pulmonary vein.

In some examples, the use includes using the plurality of electrodes for visualization, stimulation, recording, and ablation.

In some examples, each electrode is configured so an amount of power delivered to each electrode is controlled independently.

In some examples, the multi-electrode radiofrequency balloon catheter further includes a proximal handle, a distal tip, and a middle section disposed therebetween.

In some examples, the proximal handle is a deflection thumb knob allowing for unidirectional deflection, a balloon advancement mechanism, and a luer fitting for balloon inflation and irrigation.

In some examples, the multi-electrode radiofrequency balloon catheter further includes a high-torque shaft configured to be rotated to facilitate accurate positioning of the catheter tip to a desired; and a unidirectional braided deflectable tip section.

In some examples, the balloon has a membrane, the balloon having a distal end and a proximal end defining a longitudinal axis, the multi-electrode radiofrequency balloon catheter further includes a first substrate disposed on the membrane, the first substrate including a first radiopaque marker of a first form disposed thereon; and a second substrate disposed on the membrane, the second substrate including a second radiopaque marker of a second form disposed thereon, the second form being different from the first form.

In some examples, use includes controlling irrigation to the multi-electrode radiofrequency balloon catheter with an irrigation pump.

In some examples, the effectiveness evaluation period is at least 91 days following the delivering the multi-electrode radiofrequency balloon catheter to the pulmonary vein; and the ablating tissue of the pulmonary vein using the multi-electrode radiofrequency balloon catheter.

In some examples, the effectiveness evaluation period is less than or equal to one year following the delivering the multi-electrode radiofrequency balloon catheter to the pulmonary vein; and the ablating tissue of the pulmonary vein using the multi-electrode radiofrequency balloon catheter.

In some examples, use of administering an independently controlled multi-electrode radiofrequency balloon catheter for a procedure for atrial fibrillation is disclosed, including delivering a multi-electrode radiofrequency balloon catheter to a pulmonary vein; ablating tissue of the pulmonary vein using the multi-electrode radiofrequency balloon catheter; and achieving a predetermined success rate of pulmonary vein isolation.

In some examples, the predetermined success rate is 60% for a population size of at least 40 patients.

In some examples, a population size for the predetermined success rate is at least 300 patients.

In some examples, a population size for the predetermined success rate is at least 200 patients.

In some examples, a population size for the predetermined success rate is at least 100 patients.

In some examples, a population size for the predetermined success rate is at least 50 patients.

In some examples, the predetermined success rate is at least 60%.

In some examples, the predetermined success rate is determined by evaluating the patient 7 days following the delivering the multi-electrode radiofrequency balloon catheter to the pulmonary vein; and the ablating tissue of the pulmonary vein using the multi-electrode radiofrequency balloon catheter.

In some examples, the predetermined success rate is determined by evaluating the patient 1 month following the delivering the multi-electrode radiofrequency balloon catheter to the pulmonary vein; and the ablating tissue of the pulmonary vein using the multi-electrode radiofrequency balloon catheter.

In some examples, the predetermined success rate is determined by evaluating the patient 6 months following the delivering the multi-electrode radiofrequency balloon catheter to the pulmonary vein; and the ablating tissue of the pulmonary vein using the multi-electrode radiofrequency balloon catheter.

In some examples, the predetermined success rate is determined by evaluating the patient 12 months following the delivering the multi-electrode radiofrequency balloon catheter to the pulmonary vein; and the ablating tissue of the pulmonary vein using the multi-electrode radiofrequency balloon catheter.

In some examples, the predetermined success rate further includes confirming an entrance block in the pulmonary vein after at least one of adenosine and isoproterenol challenge.

In some examples, the delivering step further comprises using a focal catheter.

In some examples, the patient suffering at least one of the following events is deemed as unsuccessful pulmonary vein isolation, including:
 device or procedure related death;
 atrio-esophageal fistula, myocardial infarction;
 cardiac Tamponade/Perforation;
 thromboembolism;
 stroke/Cerebrovascular Accident (CVA);
 transient Ischemic Attach (TIA);
 phrenic Nerve Paralysis, Pulmonary Vein Stenosis;
 pericarditis;
 pulmonary Edema;
 major Vascular Access Complication/Bleeding; and
 hospitalization (initial or prolonged).

In some examples, the patient suffering at least one of the following events is deemed as unsuccessful pulmonary vein isolation, including
 acute procedural failure;
 repeat ablation or surgical treatment for AF/AT/Atypical (left-side) AFL after the blanking period (after day 90 post index procedure);
 DC cardioversion for AF/AT/Atypical (left-side) AFL, continuous AF/AT/AFL on a standard 12-lead ECG even if the recording is less than 30 seconds in duration (after day 90 post index procedure);
 a new Class I and/or Class III AAD is prescribed for AF during effectiveness evaluation period (day 91-365 post index procedure) or prescribed during the blanking period and continued past 90 days;
 a previously failed Class I and/or Class III AAD (failed at or before screening) is taken for AF at a greater dose than the highest ineffective historical dose during the effectiveness evaluation period; and
 amiodarone is prescribed post procedure.

In some examples, use of administering an independently controlled multi-electrode radiofrequency balloon catheter for a procedure for cardiac electrophysiological ablation of pulmonary veins of the atria and treating drug refractory recurrent symptomatic pulmonary atrial fibrillation, including delivering a multi-electrode radiofrequency balloon catheter to a pulmonary vein; ablating tissue of the pulmonary vein using the multi-electrode radiofrequency balloon catheter; and achieving a predetermined effectiveness rate of pulmonary vein isolation.

In some examples, use of administering an independently controlled multi-electrode radiofrequency balloon catheter is disclosed for cardiac electrophysiological ablation of pulmonary veins of the atria and drug refractory recurrent symptomatic pulmonary atrial fibrillation, including, including delivering a multi-electrode radiofrequency balloon catheter to a pulmonary vein; ablating tissue of the pulmonary vein using the multi-electrode radiofrequency balloon catheter; and achieving pulmonary vein isolation and at least a 97% safety endpoint within seven (7) days of successful pulmonary vein isolation.

In some examples, use of administering an independently controlled multi-electrode radiofrequency balloon catheter is disclosed for drug refractory recurrent symptomatic pulmonary atrial fibrillation, including delivering a multi-electrode radiofrequency balloon catheter to a pulmonary vein; ablating tissue of the pulmonary vein using the multi-electrode radiofrequency balloon catheter; and achieving pulmonary vein isolation and at least a 90% safety endpoint within seven (7) days of successful pulmonary vein isolation.

In some examples, the safety endpoint is defined by a patient suffering a primary adverse event.

In some examples, the use includes administering uninterrupted anticoagulation therapy at least 1 month prior to the procedure.

In some examples, if the patient is receiving warfarin/coumadin therapy, the patient must have an international normalized ratio $\geq 2$ for at least 3 weeks prior to the procedure.

In some examples, if the patient is receiving warfarin/coumadin therapy, the patient must be confirmed to be $\geq 2$ within 48 hours pre-procedure.

In some examples, the use includes continuing anticoagulation therapy prior to the procedure.

In some examples, the use includes targeting an activated clotting time of 350-400 seconds prior to inserting the catheter and throughout the procedure.

In some examples, the use includes checking an activated clotting time levels every 15-30 minutes during the procedure to ensure an activated clotting time target of 350-400 seconds.

In some examples, the use includes administering a transseptal puncture; confirming an activated clotting time target of ≥350 sec. prior to inserting the multi-electrode radiofrequency balloon catheter into the left atrium and maintaining throughout the procedure; introducing the multi-electrode radiofrequency balloon catheter; introducing of a multi-electrode circular diagnostic catheter; ablating the pulmonary vein with the multi-electrode radiofrequency balloon catheter; determining in real time pulmonary vein isolation with the multi-electrode circular diagnostic catheter; and confirming whether an entrance is blocked in the pulmonary vein.

In some examples, the multi-electrode circular diagnostic catheter includes an elongated body having a longitudinal axis; a distal assembly distal the elongated body, the distal assembly having a helical form comprising a proximal loop and a distal loop, and a shape-memory support member extending through at least the proximal loop, the proximal loop and the distal loop being oriented obliquely at an angle relative to the longitudinal axis of the elongated body; at least one irrigated ablation ring electrode mounted on the proximal loop; a control handle proximal the elongated body; and a contraction wire having a proximal end in the control handle and a distal end anchored in the proximal loop, the control handle including a first control member configured to actuate the contraction wire to contract the proximal loop, wherein the proximal loop has a first flexibility and the distal loop has a second flexibility, and the second flexibility is greater than the first flexibility.

In some examples, use of administering an independently controlled multi-electrode radiofrequency balloon catheter is disclosed for a procedure for pulmonary vein isolation by applying energy to tissue of a subject's heart proximate to an esophagus, phrenic nerve, or lung, including achieving a predetermined effectiveness rate according to any of the previous claims by positioning an expandable member proximate to the left atrium, the expandable member having a longitudinal axis and including a plurality of electrodes disposed about the longitudinal axis, each electrode capable of being energized independently, the plurality of electrodes including a first electrode having a first radiopaque marker and a second electrode having a second radiopaque marker different from the first radiopaque marker; viewing an image of the expandable member as well as the first and second radiopaque markers in the left atrium; determining an orientation of the first and second radiopaque markers with respect to a portion of the left atrium closest to the esophagus, phrenic nerve, or lung, of the subject; moving one of the first and second radiopaque markers to a portion of the left atrium closest to the esophagus, phrenic nerve or lung; and energizing one or more electrodes indexed to the one of the radiopaque markers proximate the portion close to the esophagus, phrenic nerve, or lung, at a lower energization setting as compared to other electrodes to create a transmural lesion in the left atrium with little or no effect to adjacent anatomical structures.

To the accomplishment of the foregoing and related ends, certain illustrative aspects are described herein in connection with the following description and the appended drawings. These aspects are indicative, however, of but a few of the various ways in which the principles of the claimed subject matter can be employed and the claimed subject matter is intended to include all such aspects and their equivalents. Other advantages and novel features can become apparent from the following detailed description when considered in conjunction with the drawings.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 14 shows a table summarizing recommended RF Energy Delivery Parameters in one example.

FIG. 15 shows a table summarizing intensity or severity of each AE assessed according to classifications.

FIG. 16 shows a table illustrating classifications based on AAD therapy administered in the blanking and post-blanking periods in an example study.

FIG. 18 shows a table summarizing results from the first study of this disclosure compared with a prior study.

FIG. 20 depicts a graphical overview of one method or use according to this disclosure.

FIG. 21 depicts a graphical overview of one method or use according to this disclosure.

FIG. 22 depicts a graphical overview of one method or use according to this disclosure.

FIG. 23 depicts a graphical overview of one method or use according to this disclosure.

FIG. 24 depicts a graphical overview of one method or use according to this disclosure.

FIG. 25 depicts a graphical overview of one method or use according to this disclosure.

FIG. 27 depicts a graphical overview of one method or use according to this disclosure.

DETAILED DESCRIPTION

Figure 1:
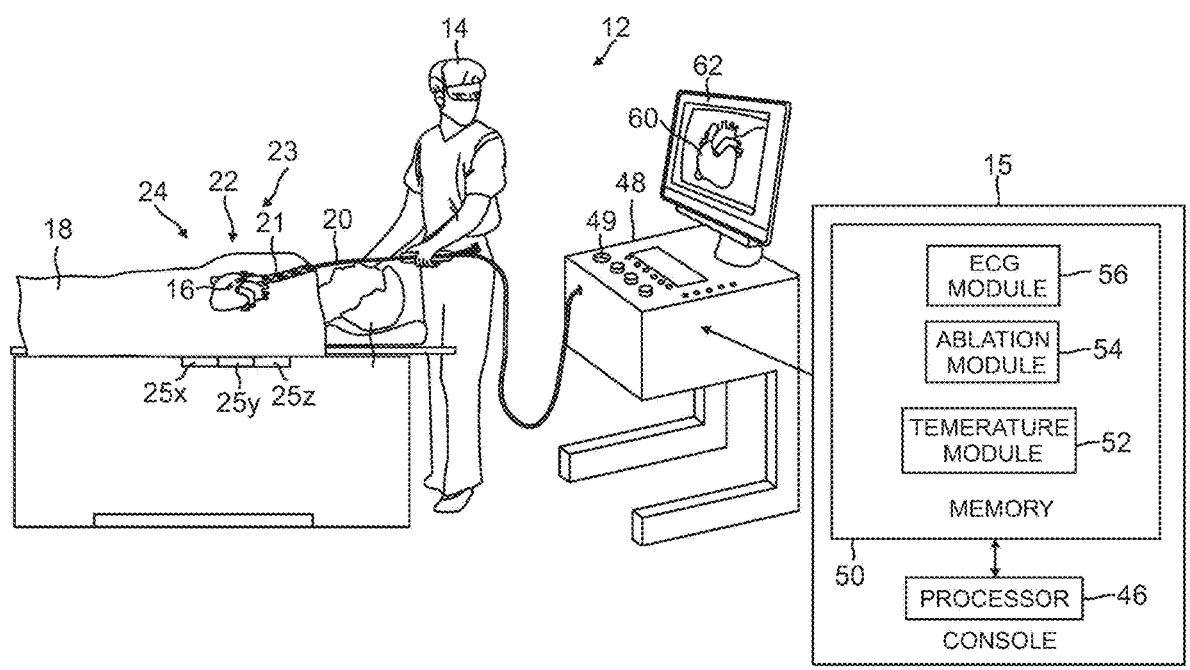
FIG. 1 is a schematic illustration of a medical procedure using example instrumentation of this disclosure.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method or use step is present in the composition or article or method or use, but does not exclude the presence of other compounds, materials, particles, method or use steps, even if the other such compounds, material, particles, method or use steps have the same function as what is named.

As used herein, the terms "about" or "approximately" for any numerical values or ranges indicate a suitable dimensional tolerance that allows the part or collection of components to function for its intended purpose as described herein. More specifically, "about" or "approximately" can refer to the range of values±20% of the recited value, e.g. "about 90%" can refer to the range of values from 71% to 99%.

In addition, as used herein, the terms "patient," "host," "user," and "subject" refer to any human or animal subject and are not intended to limit the systems or method or uses to human use, although use of the subject invention in a human patient represents a preferred embodiment.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method or use does not preclude the presence of additional method or use steps or intervening method or use steps between those steps expressly identified. Steps of a method or use can be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example.

As discussed herein, "operator" can include a doctor, surgeon, or any other individual or delivery instrumentation associated with delivery of a multi-electrode RF balloon catheter for the treatment of drug refractory atrial fibrillation to a subject.

As discussed herein, "NIHSS Score" means The National Institutes of Health Stroke Scale, or NIH Stroke Scale (NIHSS) and is a tool used by healthcare providers to objectively quantify the impairment caused by a stroke. The NIHSS is composed of 11 items, each of which scores a specific ability between a 0 and 4. For each item, a score of 0 typically indicates normal function in that specific ability, while a higher score is indicative of some level of impairment. The individual scores from each item are summed in order to calculate a patient's total NIHSS score. The maximum possible score is 42, with the minimum score being a 0.

As discussed herein, "mRS" means the modified Rankin Scale (mRS) that is a commonly used scale for measuring the degree of disability or dependence in the daily activities of people who have suffered a stroke or other causes of neurological disability. The mRS scale runs from 0-6, running from perfect health without symptoms to death. An mRS score of 0 is understood as no symptoms being observed. An mRS score of 1 is understood as no significant disability is observed and the patient is able to carry out all usual activities, despite some symptoms. An mRS score of 2 is understood as slight disability and the patient is able to look after own affairs without assistance, but unable to carry out all previous activities. An mRS score of 3 is understood as moderate disability whereby the patient can require some help but is able to walk unassisted. An mRS score of 4 is understood as moderate severe disability and the patient is unable to attend to own bodily needs without assistance or walk unassisted. An mRS score of 5 is understood as severe disability and the patient requires constant nursing care and attention, bedridden, incontinent. An mRS score of 6 is understood as the patient being deceased.

As discussed herein, the term "safety", as it relates to devices used in ablating cardiac tissue, related delivery systems, or method or use of treatment refers to a relatively low severity of adverse events, including adverse bleeding events, infusion or hypersensitivity reactions. Adverse bleeding events can be the primary safety endpoint and include, for example, major bleeding, minor bleeding, and the individual components of the composite endpoint of any bleeding event.

As discussed herein, unless otherwise noted, the term "clinically effective" (used independently or to modify the term "effective") can mean that it has been proven by a clinical trial wherein the clinical trial has met the approval standards of U.S. Food and Drug Administration, EMEA or a corresponding national regulatory agency. For example, a clinical study can be an adequately sized, randomized, double-blinded controlled study used to clinically prove the effects of the cardiac ablation device(s) and related system (s) of this disclosure. Most preferably to clinically prove the effects of the device(s) with respect to all targeted pulmonary veins, for example, to achieve a clinically effective outcome in for the patient (e.g., mRS less than or equal to 2) and/or achieve pulmonary vein isolation in those afflicted veins.

As discussed herein, the term "computed tomography" or CT means one or more scans that make use of computer-processed combinations of many X-ray measurements taken from different angles to produce cross-sectional (tomographic) images (virtual "slices") of specific areas of a scanned object, allowing the user to see inside the object without cutting. Such CT scans of this disclosure can refer to X-ray CT as well as many other types of CT, such as positron emission tomography (PET) and single-photon emission computed tomography (SPECT).

The present disclosure is related to systems, method or uses and devices for ablating cardiac tissue to treat cardiac arrhythmias. Ablative energies are typically provided to cardiac tissue by a tip portion which can deliver ablative energy alongside the tissue to be ablated. Some of these catheters administer ablative energy from various electrodes three-dimensional structures. Ablative procedures incorporating such catheters can be visualized using fluoroscopy.

Ablation of cardiac tissue to correct a malfunctioning heart is a well-known procedure. Typically, to successfully ablate, cardiac electropotentials need to be measured at various locations of the myocardium. In addition, temperature measurements during ablation provide data enabling the efficacy of the ablation to be measured. Typically, for an ablation procedure, the electropotentials and the temperatures are measured before, during, and after the actual ablation.

Previous solutions have used two or more separate instructions (e.g., one for the electropotentials and temperature measurements, and another for the ablation), embodiments disclosed herein facilitate the two measurements, and in addition enable ablation using radiofrequency electromagnetic energy, using a single catheter. The catheter has a lumen, and a balloon is deployed through the catheter lumen (the balloon travels through the lumen in a collapsed, uninflated configuration, and the balloon is inflated on exiting the lumen). The balloon has an exterior wall or membrane and has a distal end and a proximal end which define a longitudinal axis that extends the lumen.

As an example, FIG. 1 depicts example instrumentations that include an apparatus 12, according to an example embodiment. The procedure is performed by an operator 14, and the procedure in the description hereinbelow is assumed to comprise ablation of a portion of a myocardium 16 of the heart of a human patient 18. However, it is understood that embodiments disclosed herein are not merely applicable to this specific procedure and can include substantially any procedure on biological tissue or on non-biological materials.

To perform the ablation, the operator 14 inserts a probe 20 into a sheath 21 that has been pre-positioned in a lumen of the patient. Sheath 21 is positioned so that a distal end 22 of probe 20 enters the heart of the patient. A multi-electrode radiofrequency balloon catheter 24 (e.g., a balloon catheter), which is described in more detail below, is deployed through a lumen 23 of the probe 20 and exits from a distal end of the probe 20. Catheter 24 can be a multi-electrode radiofrequency balloon catheter for cardiac electrophysiological ablation of pulmonary veins of the atria and, when used with a multi-channel RF generator, for the treatment of drug refractory recurrent symptomatic PAF, as discussed more particularly below. Catheter 24 can be understood as including features more clearly described in Appendix 1 of priority U.S. App. No. 62/754,275, which includes U.S. Pat. No. 9,907,610; U.S. Pat. Pubs. 2016/0175041; 2017/0311893; 2017/0311829; 2017/0347896; 2016/0175041; 2017/0311893; 2017/0311829; and 2017/0347896 and U.S. patent application Ser. Nos. 15/476,191; 15/939,154; 15/847,661; 15/684,434; 15/689,388; 15/815,394; 15/837,339; 15/857, 101; 15/870,375; 15/838,962; and 62/769,424, each of which are incorporated by reference in their entirety as if set forth verbatim herein. Note that such catheters 24 can be introduced through the femoral artery, wrist artery (radial access) or directly through the carotid artery. While both radial and carotid access avoids the aortic arches, there are other drawbacks. However, all three approaches are considered to be known to ones of skill in this art.

Functionally, catheter 24 seeks to achieve isolation of the pulmonary veins in the subject's LA to eliminate symptoms of AF. The catheter 24 ablates from multiple irrigated, independently-controlled electrodes simultaneously. The amount of power delivered to each electrode is controlled independently to improve safety and lesion quality.

One RF generator contemplated for use in this disclosure can be for cardiac ablation applications to generate RF energy for delivery to a site in the heart via compatible RF ablation catheters. The generator is capable of independently controlling the delivery of RF energy to electrodes simultaneously. The generator can include functions for controlling ablation parameters at the ablation electrodes of the catheter. Ablation parameters, such as power, impedance, ablation duration, and temperature are recorded and can be exported at the end of the procedure to a USB device.

As shown in FIG. 1, apparatus 12 is controlled by a system processor 46, which is in an operating console 15 of the apparatus. Console 15 comprises controls 49 which are used by professional 14 to communicate with the processor. During the procedure, the processor 46 typically tracks a location and an orientation of the distal end 22 of the probe 20, using any method or use known in the art. For example, processor 46 can use a magnetic tracking method or use, wherein magnetic transmitters 25X, 25Y and 25Z external to the patient 18 generate signals in coils positioned in the distal end of the probe 20. The CARTO® system (available from Biosense Webster, Inc. of Irvine, Calif.) uses such a tracking method or use.

To operate apparatus 12, the processor 46 communicates with a memory 50, which has many modules used by the processor to operate the apparatus. Thus, the memory 50 comprises a temperature module 52, an ablation module 54, and an electrocardiograph (ECG) module 56, the functions of which are described below. The memory 50 typically comprises other modules, such as a force module for measuring the force on the distal end 22, a tracking module for operating the tracking method or use used by the processor 46, and an irrigation module allowing the processor to control irrigation provided for the distal end 22.

While other modules are not illustrated in FIG. 1, others are indeed contemplated and can include hardware as well as software elements. For example, module 54 can include a radio-frequency generator with at least one output or output channel, e.g., ten outputs or ten output channels. Each of the outputs can be separately and selectively activated or deactivated by a switch. That is, each switch can be disposed between the signal generator and a respective output. Thus, a generator with ten outputs would include ten switches. These outputs can each be individually coupled to electrodes on an ablation catheter, e.g., the ten electrodes 33 on balloon 80, described in further detail below. Electrodes 33 can be irrigated, flexible gold-plated electrodes bonded thereto and used to deliver RF energy in a unipolar fashion to the tissue and sense temperature at each electrode. Electrodes 33 can be oriented circularly to achieve good circumferential contact with the ostia of the pulmonary veins. The catheter 24 can ablate cardiac tissue from the independently-controlled electrodes simultaneously when paired with a Multi-Channel RF generator and the amount of power delivered to each electrode is controlled independently.

Such an electrical connection can be achieved by establishing an electrical path between each output and each electrode. For example, each output can be connected to a corresponding electrode by one or more wires or suitable electrical connectors. Thus, in some embodiments, an electrical path can include at least one wire. In some embodiments, the electrical path can further include an electrical connector and at least a second wire. Thus, electrodes 33 can be selectively activated and deactivated with the switches to receive radiofrequency energy separately from each of the other electrodes.

Figure 2:
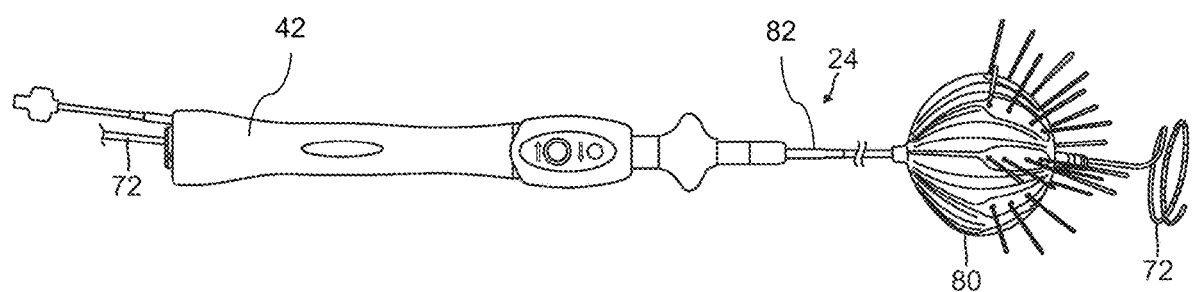
FIG. 2 is a top view of one example catheter of this disclosure with a balloon in an expanded state, in use with a lasso catheter.

FIG. 2 is a top view of catheter 24. Catheter 24 has a usable length of approximately 110 cm (though other dimensions are contemplated as needed or required). Catheter 24 can have three major sections: handle 42, shaft portion 82 and distal tip 22. The shaft 82 can measure 10.5 F with a 13.5 F maximum outer diameter around the balloon 80 when the balloon is in its fully collapsed state. The catheter 24 can have a high-torque shaft 82, with a uni-directional braided deflectable tip section. The shaft allows the plane of the curved tip with balloon 80 to be rotated to facilitate accurate positioning of the catheter tip 22 to the desired site (ostia of the pulmonary veins). The compliance of the balloon 80 allows for its flexible surface electrodes 33 to conform to the anatomy when pressed against the tissue.

The handle section 42 can incorporate a deflection thumb knob allowing for unidirectional deflection, a balloon advancement mechanism, and a luer fitting for balloon inflation and irrigation. An additional luer fitting can be included and located proximally to the ejector and serve as an entry port for a guidewire as well as distal irrigation and/or contrast injection. The catheter 24 can be used with an irrigation pump to control irrigation to the balloon. Heparinized normal saline can be delivered through the luer fitting of the handle 42.

Figure 3:
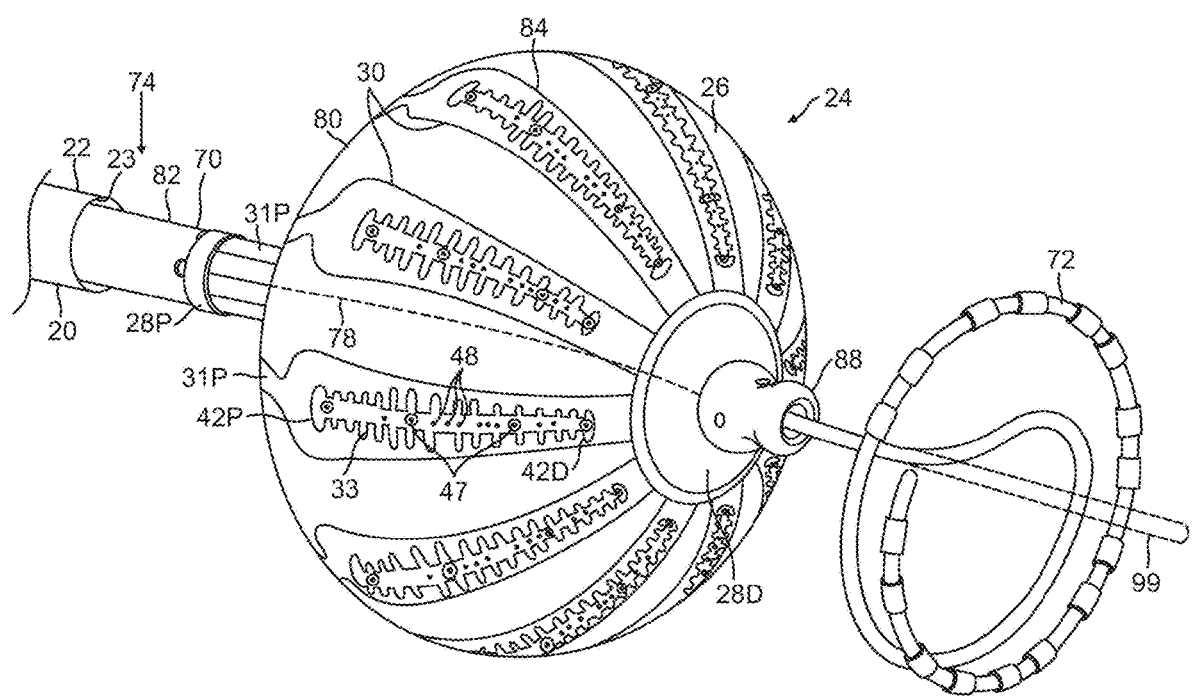
FIG. 3 is a perspective view of a balloon along with the lasso catheter.

FIG. 3 is a schematic perspective view of an example multi-electrode radiofrequency balloon catheter 24 in an expandable configuration in the form of a balloon in its expanded configuration, according to an embodiment. In a disclosed embodiment, where the multi-electrode radiofrequency balloon catheter 24 is used to ablate an ostium 11 of a lumen, such as a pulmonary vein 13, the multi-electrode radiofrequency balloon catheter 24 is supported by a tubular shaft 70 having a proximal shaft portion 82 and a distal shaft end 88. The shaft 70 includes a hollow central tube 74, which permits a catheter to pass therethrough and past the distal shaft end 88. The catheter can be a focal linear catheter or a lasso catheter 72, as illustrated, or a diagnostic catheter. It is also intended that the catheter can have a relatively small diameter (e.g., ~3 mm) through which a similarly small diameter catheter, such as a focal linear catheter or the like, could be used. The lasso catheter 72 can be inserted into the pulmonary vein to position the multi-electrode radiofrequency balloon catheter 24 correctly with respect to the ostium prior to ablation of the ostium. The distal lasso portion of the catheter 72 is typically formed of shape-memory retentive material such as nitinol. It is understood that the multi-electrode radiofrequency balloon catheter 24 can also be used with a linear or focal catheter 99 (as shown in broken lines in FIG. 3) in the PV or elsewhere in the heart. Any catheter used in conjunction with the multi-electrode radiofrequency balloon catheter 24 can have features and functions, including, for example, pressure sensing, ablation, diagnostic, e.g., navigation and pacing.

The balloon 80 of the multi-electrode radiofrequency balloon catheter 24 can have an exterior wall or membrane 26 of a bio-compatible material, for example, formed from a plastic such as polyethylene terephthalate (PET), polyurethane or PEBAX®. The shaft 70 and the distal shaft end 88 define a longitudinal axis 78 of the balloon 80. The balloon 80 is deployed, in a collapsed configuration, via the lumen 23 of the probe 20, and can be expanded after exiting from the distal end 22. The membrane 26 of the balloon 80 is formed with irrigation pores or apertures 27 through which the fluid (e.g., saline) can exit from the interior of the balloon 80 to outside the balloon for cooling the tissue ablation site at the ostium. It is understood that the fluid can exit the balloon 80 with any desired flow rate or pressure, including a rate where the fluid is seeping out of the balloon 80.

Figure 4A:
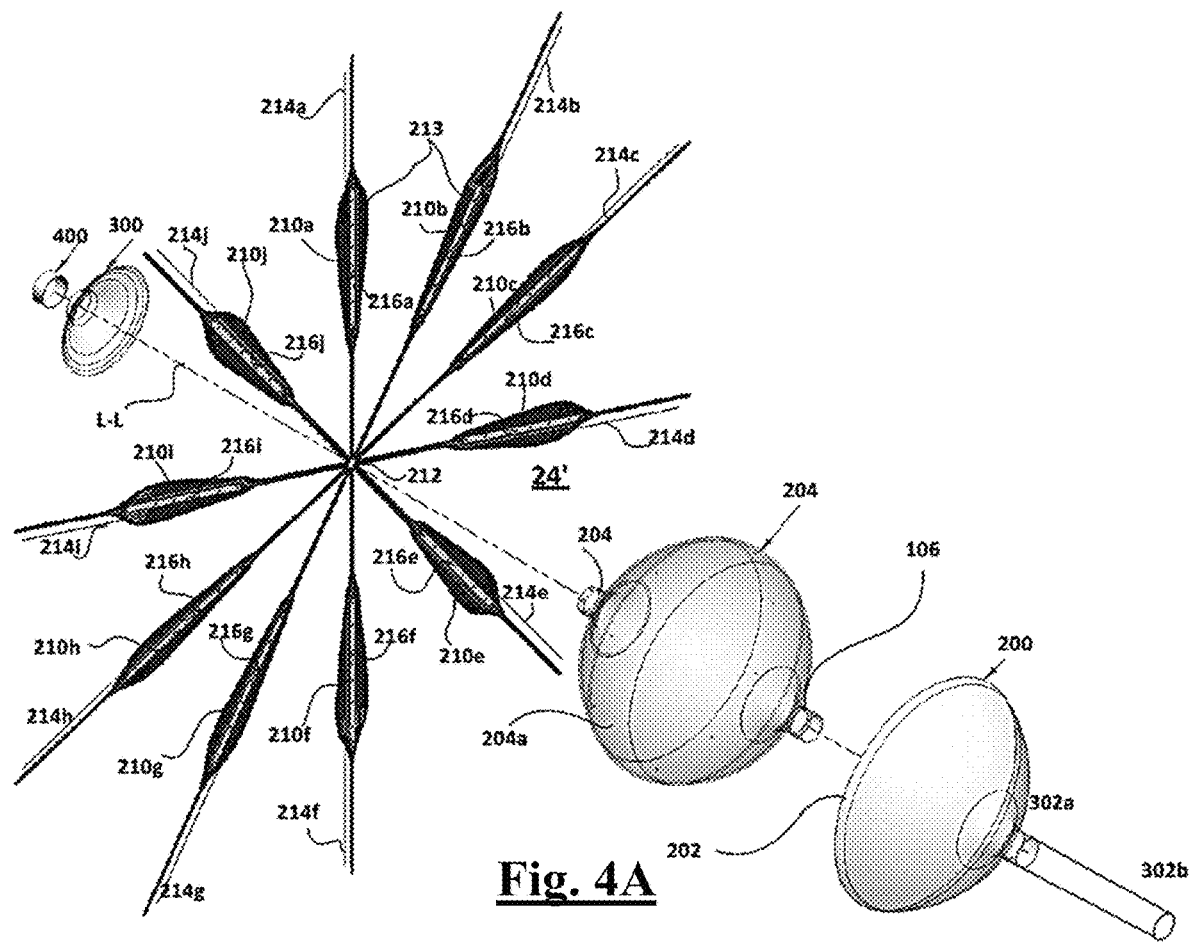
FIG. 4A is an exploded perspective view of the medical probe which shows a base balloon or first expandable membrane with radiating electrode assemblies that are partially covered by respective second and third expandable membranes.

Yet another embodiment of the catheter was utilized in the study, referenced here as probe 24'. FIG. 4A illustrates an exploded perspective view of the electrophysiology probe 24' that includes a tubular member 302 extending along a longitudinal axis L-L from a first (proximal) end 302b to a second (or distal) end 302a. A first expandable membrane 204 is attached to the tubular member 302 near the distal end 302b. The membrane 204 has an outer surface 204a and an inner surface 204b disposed about the longitudinal axis L-L. The outer surface 204a is exposed to the ambient environment while the inner surface 204b is exposed to the internal volume of the balloon defined by the membrane 204. The first expandable membrane 204 has a first expandable distal membrane portion 208 being coupled to the second end 302a of the tubular member 302 and second expandable distal membrane portion 206 spaced apart from the first expandable distal membrane portion 208 along the longitudinal axis L-L.

It is noted that first expandable membrane 204 is configured to be expanded from a compressed shape (generally tubular configuration) to a balloon (or generally spheroidal) shaped member. A plurality of electrodes (210a, 210b, 210c, 210d, 210e, 210f, 210g, 210h, 210i and 210j, which may be referred to singularly or collectively as "electrode 210") are disposed on the outer surface 204a of the first expandable membrane 204. The electrodes 210 are arranged so that they radiate from a generally common center or centroid substrate 212 near the second expandable distal membrane portion 208 which is distal to the tubular member 302. The electrodes 210a-210j may have one or more wires, i.e., bifilar 214a-214j, respectively, connected to each of the plurality of electrodes 210a-210j via a connection junction 216a-216j. Each of the wires 214a-214j (which may be singular in form "wire" or plural "wires" will be collectively referred to as "wire 214") is connected to the connection point at the "underside" surface of the electrode 210. The underside surface of each electrode 210 is the electrode surface that is not exposed to the ambient environment and is typically bonded to the outer surface 204a of the membrane 204. As the connection point 216 (typically a solder point) is generally at the center of the electrode, the wire is covered by the underside surface of each electrode. However, as each wire or bifilar 214a-214j extends toward the tubular member 302, the electrode surface or the substrate on which the electrode is bonded thereto becomes smaller thereby leaving the wire or bifilars 214a-214j exposed.

Figure 4B:
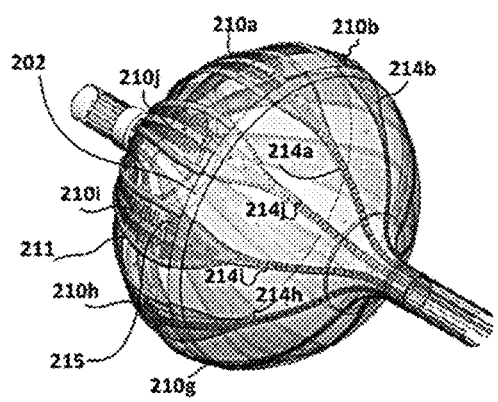
FIG. 4B illustrates an assembled medical probe of FIG. 3.
Figure 5:
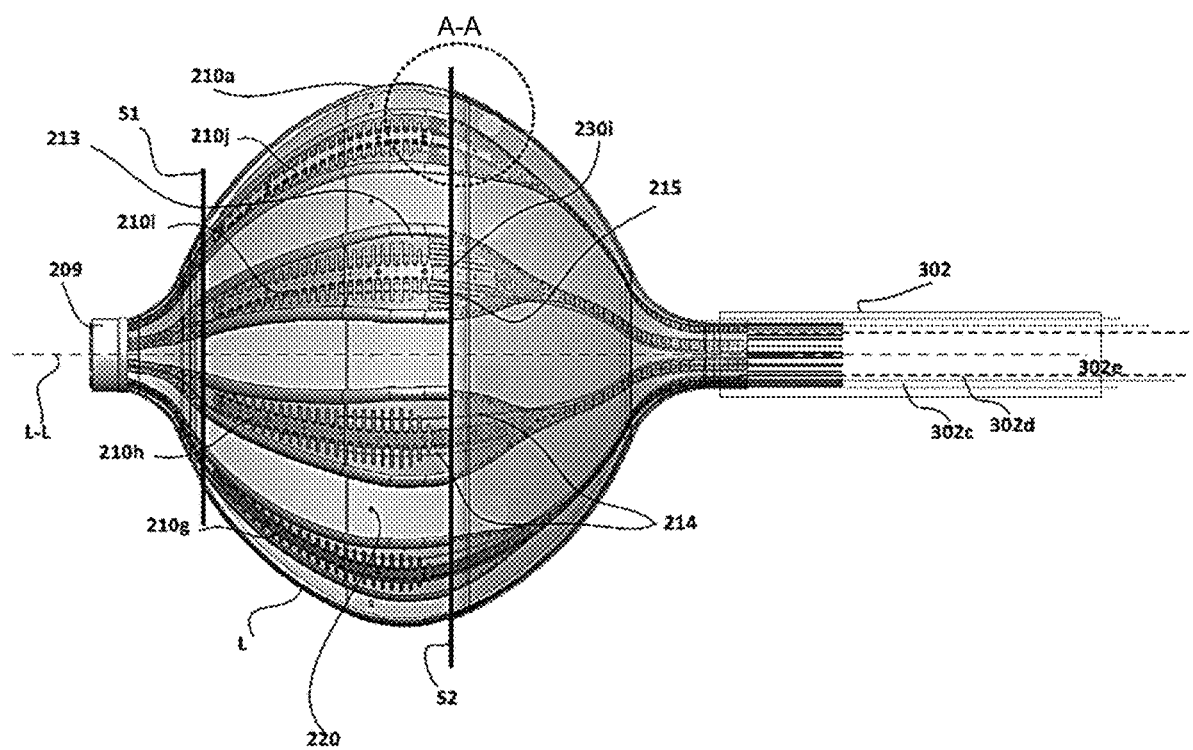
FIG. 5 is a side view of the medical probe of FIG. 3.
Figure 7:
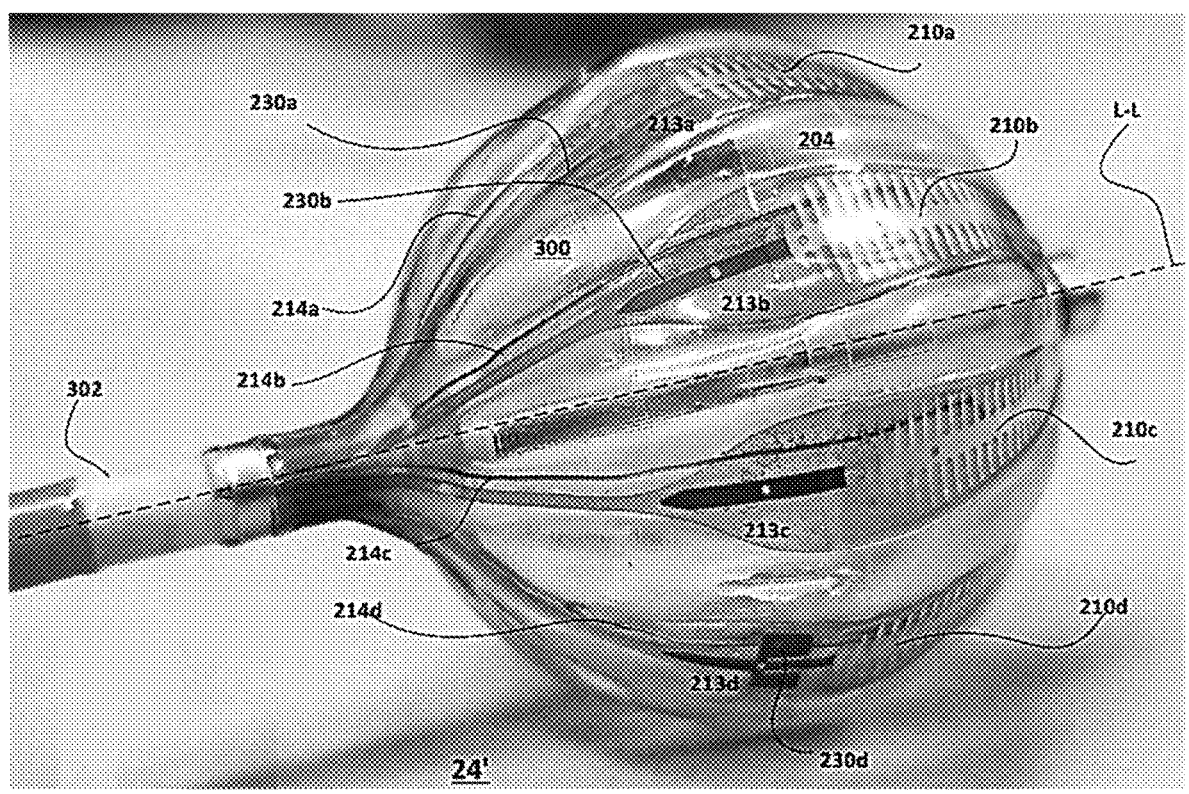
FIG. 7 is a photograph of an actual prototype according to an embodiment described and illustrated herein.

As can be seen in FIG. 4B, when group of wires 214a-214j are mounted on the membrane 204, each wire 214 is configured to extend from the tubular member 302 to the respective electrode 210 such that each wire follows the topographic outer surface 204a of membrane 204. In extending the wires 214 toward the tubular member 302, the wires 214 become exposed to the ambient environment (e.g., biological tissues or blood) as each wire 214 leaves the underside surface of each electrode or the underside surface of the substrate 213 (FIG. 5). As each wire 214 may be used to conduct or transmit electrical energy or signals, it would be detrimental to expose the wires 214 to the ambient biological tissue environment. As such, we have devised a second expandable membrane 200 that encapsulates the one or more wires (214a-214j) between the second expandable membrane 204 and the first expandable membrane 200 so that the wires 214a-214j are constrained between the first and second expandable membrane (FIG. 7). Such configuration eliminates the exposure of the wires to the ambient environment yet still allowing the electrodes/thermocouples to be exposed to biological tissues so that the electrodes and thermocouples to work for their intended purposes. Moreover, as the wires 214 are constrained or captured between the first and second membranes, there is virtually no likelihood of the wires being entangled or mis-connected to the wrong electrode or thermocouple during assembly. In the preferred embodiment, each wire of the bifilar is coupled to a temperature sensor in the form of a thermocouple 216 disposed on or near each electrode 210.

It is noted that tubular member 302 defines a first internal passageway in the form of a lumen 302c, shown here as dashed lines in FIG. 5, that extends from the first end 302a to the second end 302b of tubular member 302 so that the one or more wires are disposed in the first lumen 302c. To allow other instruments (e.g., guide wires, optical sensor etc.) to be delivered through the balloon 204 (and outside of the distal-most portion 209 of balloon) the tubular member 302 can be provided with a second lumen 302d that extends through the membrane portions 206 and 208 to allow for another instrument to pass through the second lumen 302d. Additionally, the tubular member 302 can be provided with yet another internal passageway in the form of a third lumen 302e. Irrigation fluid can be provided in either of the second lumen 302d or third lumen 302e so that the irrigation fluid flows into the internal volume of the membrane 204, through openings or pores 220 provided through the membrane inner surface 204b and outer surface 204a to outside of the membrane 204 to the ambient environment (e.g., biological tissues or organ). Each electrode may have four irrigation openings formed on the electrode such that the electrode irrigation openings are aligned with the pores 220 of the membrane. In the preferred embodiment, lumen 302c, lumen 302d and 302e are configured or extruded as concentric passageways, in the form of a tube 302e within tube 302d within a tube 302c with outer tubular member 302. Tubular member 302 can be a suitable biocompatible polymer as is known to those skilled in the art.

Referring to FIG. 4B, the plurality of electrodes 210a-210j extend from a substrate centroid 212 equiangularly about the longitudinal axis L-L from the first expandable distal membrane portion 208 towards the second expandable distal membrane portion 206 such that the second expandable membrane 200 encapsulates a portion of each of the electrodes (210a-210j) proximate the second expandable membrane portion 206. The second expandable membrane 200 has a border 202 (FIG. 4A) that extends over a proximal portion (i.e., fish-head 115) of the electrode 210 outer surface (FIG. 4B) while allowing the electrode fish-bone pattern 210 to be exposed to the ambient environment.

That is, each of the plurality of electrodes 210a-210j defines a fishbone pattern not covered by the second expandable membrane 200 to allow the fishbone electrodes to be exposed to the ambient environment. Each electrode (210a-210j) is coupled to the outer surface of the first expandable membrane 204 via a substrate 213 which itself is connected to or bonded to the outer surface 204a of the first expandable membrane 204. The electrode 210a-210j can have a portion of its perimeter bonded directly to membrane 204. A suitable seal 211 can be formed so that the seal 211 runs along the outer perimeter of the substrate 213 of each electrode (210a-210j). In a preferred embodiment, the seal 211 can be provided in the form of a polyurethane seal.

Referring to FIG. 5, a radiopaque marker 230 is defined by a proximal fish-head portion of each electrode such that there can be respective radiopaque markers 230a, 230b, 230c, 230d, 230e, 230f, 230g, 230h, 230i and 230j for corresponding electrodes 210a-210j. To ensure that the location of each electrode can be determined while inside a body organ with x-rays, each electrode 210 may have a radiopaque marker (230a-230j) with each marker having a configuration different from other radiopaque markers on the other electrodes.

Referring back to FIG. 4A, a third expandable membrane 300 can be disposed proximate the first expandable distal membrane portion 208 so that the third expandable membrane 300 encircles an outer surface portion of the first expandable membrane 204 about the longitudinal axis L-L proximate the distal portion 209 of the membrane 204. The third expandable membrane encapsulates a portion of the substrate 213 (FIG. 5) for each of the plurality of electrodes near distal portion 209 of membrane 204. Preferably, the third expandable membrane 300 allows for encapsulation of the substrates 213 of each electrode (210a-210j) as the substrates 213 converge to centroid 212 near the distal portion 209 of the membrane 204. A retaining ring 209 is disposed about the third expandable membrane 300 (near distal portion 208 of membrane 204) to hold the third expandable membrane 300 as well as the substrates 213 to the first expandable membrane 204. The third expandable membrane 300 can be bonded to the first expandable membrane 204 thereby capturing the substrate 213 therebetween the two membranes (204 and 300).

Figure 6A:
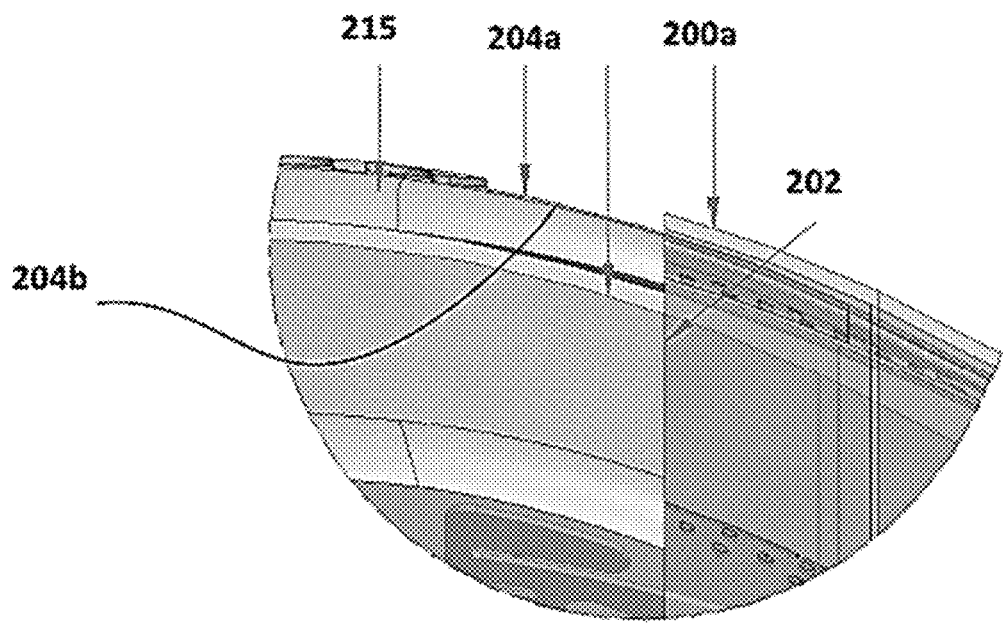
FIG. 6A is a blown-up side view of a portion of the membrane of FIG. 4A.
Figure 6B:
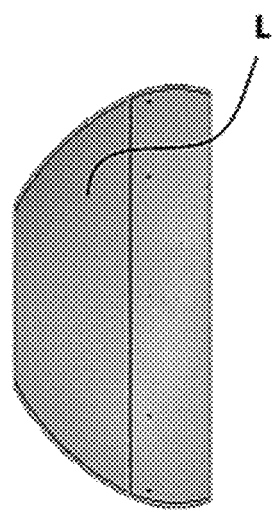
FIG. 6B illustrates a lateral or circumferential surface area (shaded portion) not covered by the hemispherical second and third expandable membranes of FIG. 3.

Referring to FIG. 6A, a blown-up side view of a portion of the membrane of FIG. 4A is shown. FIG. 6B shows a lateral or circumferential surface area (shaded portion) that is not covered. In particular, the surface area of the membrane 204 that is exposed (i.e., not covered) by second expandable membrane 200 and a third expandable membrane has a circumferential surface area L delineated between a virtual slice S1 (defined by the intersection of third expandable membrane 300 with first expandable membrane 204) orthogonal to axis L-L and virtual slice S2 orthogonal to the longitudinal axis L-L whereby slice S2 is defined by the intersection of the second expandable membrane 200 to the first expandable membrane 204. For clarity, it can be seen in FIG. 6B that if the first expandable membrane 204 approximates a sphere (when membrane 204 is expanded to its service characteristic) then the circumferential surface area L can be determined once the parameters of the spheroid body is known. In the preferred embodiment, shown in FIG. 7, the first expandable membrane 204 includes a circumferential surface area L (FIGS. 5 and 6B) of approximately 52% of a total surface area of the first expandable membrane 204. That is, the circumferential surface area L is the exposed surface area (without any electrode or substrate) of first expandable membrane 204 or outer circumferential area of first expandable membrane 204 that is also not covered by the second expandable membrane 200 and third expandable membrane 300. Further, it is noted that each substrate 213 for each electrode 210 includes a substrate surface area approximately 8% of the exposed outer circumferential surface area L of the first expandable membrane 204. In the preferred embodiments, the second expandable membrane 200 and third expandable membrane 300 cover approximately half of the outer surface area of the first expandable membrane 204.

In the preferred embodiments, the first expandable membrane includes a generally spheroidal member with a diameter as referenced to the longitudinal axis L-L of about 30 millimeters and the second expandable membrane and the third expandable membrane each includes a hemi-spherical member with the respective major diameter of each hemi-spherical member being less than 30 mm. In the preferred embodiments, the total surface area of membrane 204 is about 4500 squared-mm while the circumferential surface area L is about 2400 squared-mm and each flexible substrate 213 is about 200 squared-mm when the membrane 204 is at its fully expanded (i.e., designed) configuration, shown exemplarily in FIG. 7.

The balloon 204 of the diagnostic/therapeutic catheter has an exterior wall or membrane 204a of a bio-compatible material, for example, formed from a plastic such as polyethylene terephthalate (PET), polyurethane or PEBAX®. The tubular shaft 302 and the distal shaft end 302a define a longitudinal axis L-L of the balloon 204. The balloon 204 is deployed, in a collapsed configuration as described in commonly-owned U.S. patent application Ser. No. 15/939,154 filed on Mar. 28, 2018 via the lumen 23 of the probe 20 in this prior application, which is incorporated by reference herein to this present application). The membrane 204a of the balloon 204 is formed with irrigation pores or apertures 220 (shown in FIG. 5) through which the fluid (e.g., saline) can exit from the interior of the balloon 204 to outside the balloon for cooling the tissue ablation site at the ostium.

As described earlier in relation to FIG. 4B, membrane 24 supports and carries a combined electrode and temperature sensing member which is constructed as a multi-layer flexible circuit electrode assembly 210a-210j. The "flex circuit electrode assembly" 210a-210j may have many different geometric configurations than as shown here. In the illustrated embodiment, the flex circuit electrode assembly 210a-210j has a plurality of radiating substrates or strips 213a-213j, as best seen in FIG. 2. The substrates 213a-213j are evenly distributed about the distal end 209 and the balloon 204. Each substrate 213a-213j has wider proximal portion that gradually tapers to a narrower distal portion as referenced to the longitudinal axis.

For simplicity, the flex circuit electrode assembly 210 is described with respect to one of its substrate 213 as shown in FIG. 5, although it is understood that following description may apply to each substrate 213 of the assembly 210. The flex circuit electrode assembly 210 includes a flexible and resilient sheet substrate material 213, constructed of suitable bio-compatible materials, for example, polyimide. In some embodiments, the sheet substrate material 213 has a greater heat resistance (or a higher melting temperature) compared to that of the balloon membrane 204. In some embodiments, the substrate material 213 is constructed of a thermoset material having a decomposition temperature that is higher than the melting temperature of the balloon membrane 204 by approximately 24 degrees Celsius or more.

The substrate material 213 is formed with one or more irrigation pores or apertures (not labeled) that are in alignment with the irrigation apertures 220 of the balloon member 204 so that fluid passing through the irrigation apertures 220 and (not labeled) can pass to the ablation site on the ostium.

The substrate material 213 has a first or outer surface facing away from the balloon membrane 204, and a second or inner surface facing the balloon membrane 204. On its outer surface, the substrate material 213 supports and carries the contact electrodes 210. The configuration or trace of the contact electrode 210 may resemble a "fishbone" but it should be noted that the invention is not limited to such configuration. In contrast to an area or "patch" ablation electrode, the fingers of the contact electrode 210 advantageously increase the circumferential or equatorial contact surface of the contact electrode 210 with the ostium while void regions between adjacent fingers advantageously allow the balloon 204 to collapse inwardly or expand radially as needed at locations along its equator. In the illustrated embodiment, the fingers have different lengths, some being longer, others being shorter. For example, the plurality of fingers includes a distal finger, a proximal finger and fingers therebetween, where each of the fingers in between has a shorter adjacent finger. For example, each finger has a length different from its distal or proximal immediately adjacent neighboring finger(s) such that the length of each finger generally follows the tapered configuration of each substrate 213. In the illustrated embodiment, there are 22 fingers extending across (past each lateral side of) the elongated portion. In some embodiments, the contact electrode 210 includes gold with a seed layer between the gold and the membrane 204. The seed layer may include titanium, tungsten, palladium, silver, or combinations thereof.

Figure 8:
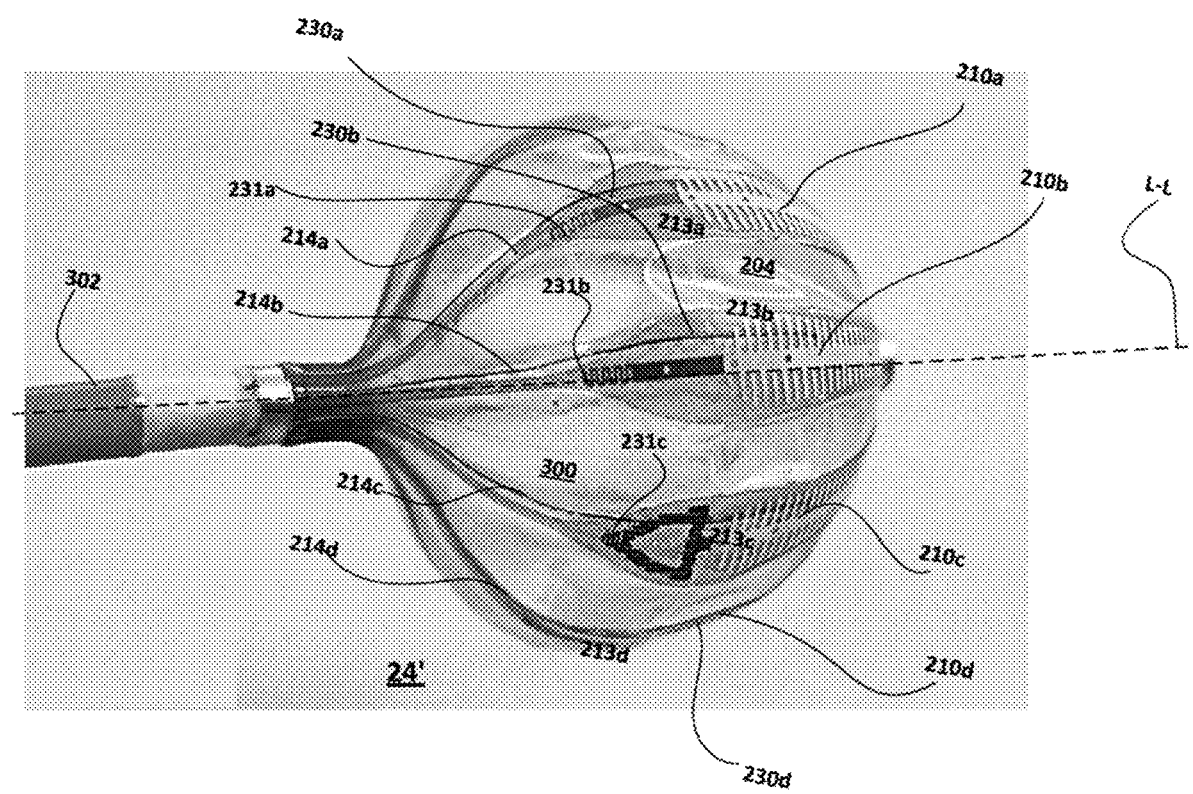
FIG. 8 is a photograph of yet another prototype of the embodiments described and illustrated herein.

As shown in FIG. 8, the flexible electrode may have its radiopaque marker in the variation identified as 231a, 231b, 231c and so on to assist in the identification of the electrode being energized. The markers 231a-231j have various serpentine configurations (as compared to FIG. 7) to allow for increased flexibility due to the presence of the second membrane 200 which tend to reduce the flexibility of the device near the markers 231a-231j.

Figure 9:
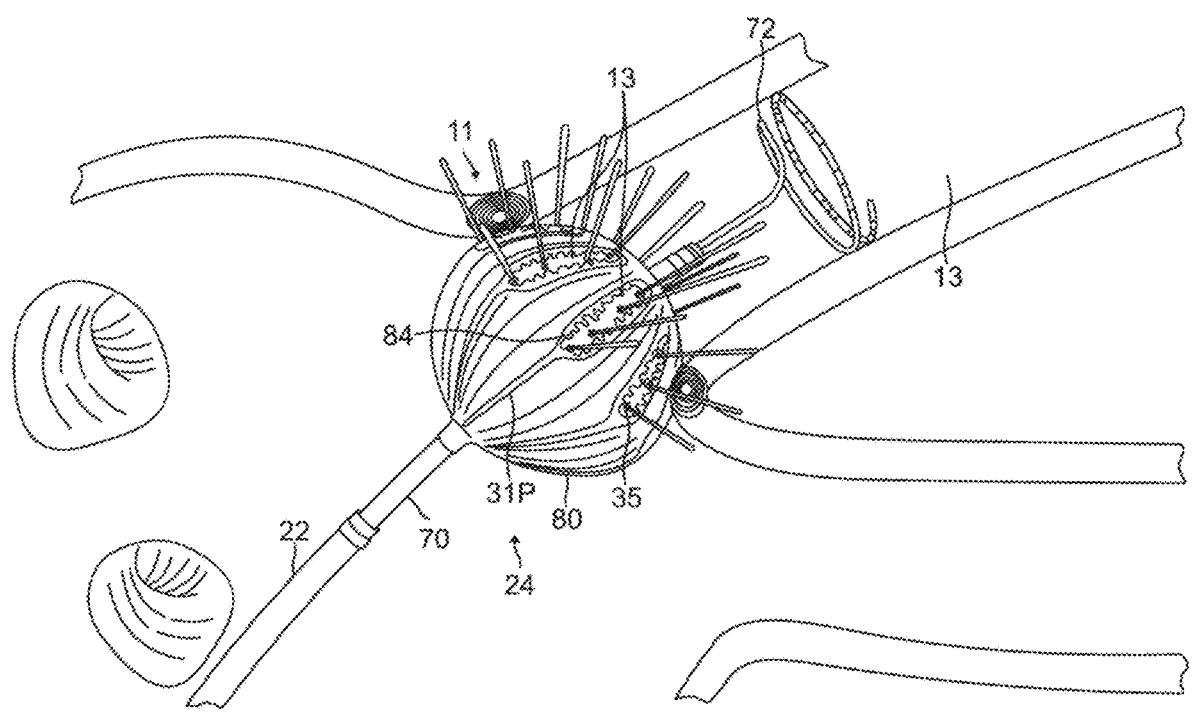
FIG. 9 is a side view of a distal end of the catheter of FIG. 2 deployed in the region of a pulmonary vein and its ostium.

The membrane 26 supports and carries a combined electrode and temperature sensing member which is constructed as a multi-layer flexible circuit electrode assembly 84. The "flex circuit electrode assembly" 84 can have many different geometric configurations. In the illustrated embodiment, the flex circuit electrode assembly 84 has a plurality of radiating substrates or strips 30. One or more electrodes 33 on each substrate come into galvanic contract with the ostium 11 during an ablation procedure, during which electrical current flows from the electrodes 33 to the ostium 11, as shown in FIG. 9.

The circuit which contains the electrodes 33 can be made of a very flexible and resilient polyimide substrate (e.g., about 0.001 inch thick) with a layer of gold on the top (exterior surface) and a layer of gold plated copper on the back side (between the circuit and the balloon 80). In order to deliver current to the electrodes 33, a bifilar wire can be connected to each electrode 33, routed through the catheter 24, and terminated in the connector in the handle 42. The bifilar wire can be made of one copper and one constantan wire. The copper wire can be used for RF delivery. In order to fit the catheter 24 into the sheath, it is necessary to first collapse the balloon 80 with its flexible electrodes 33 to a smaller diameter by moving the distal end of the balloon 80 forward a specific distance to provide the elongation necessary to decrease the balloon's outer diameter (OD).

Figure 10:
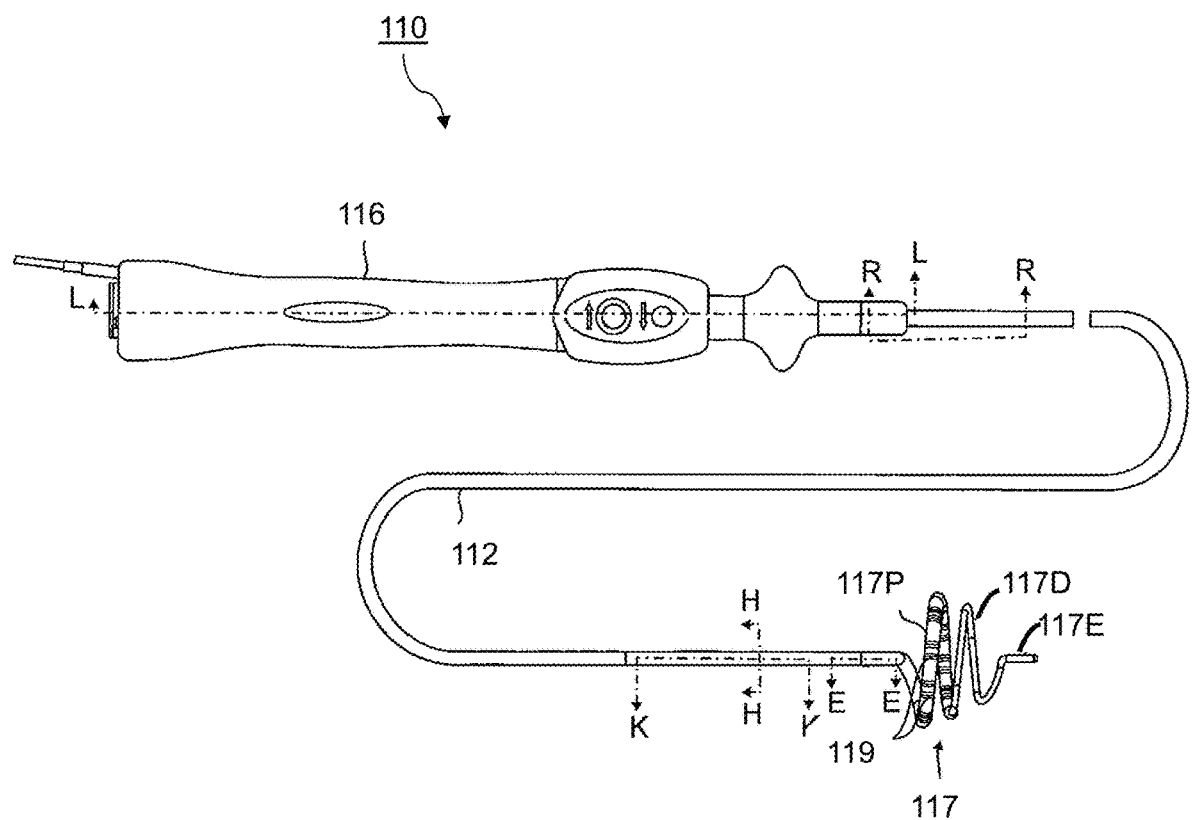
FIG. 10 is a top plan view of an example diagnostic catheter of the present disclosure.
Figure 11:
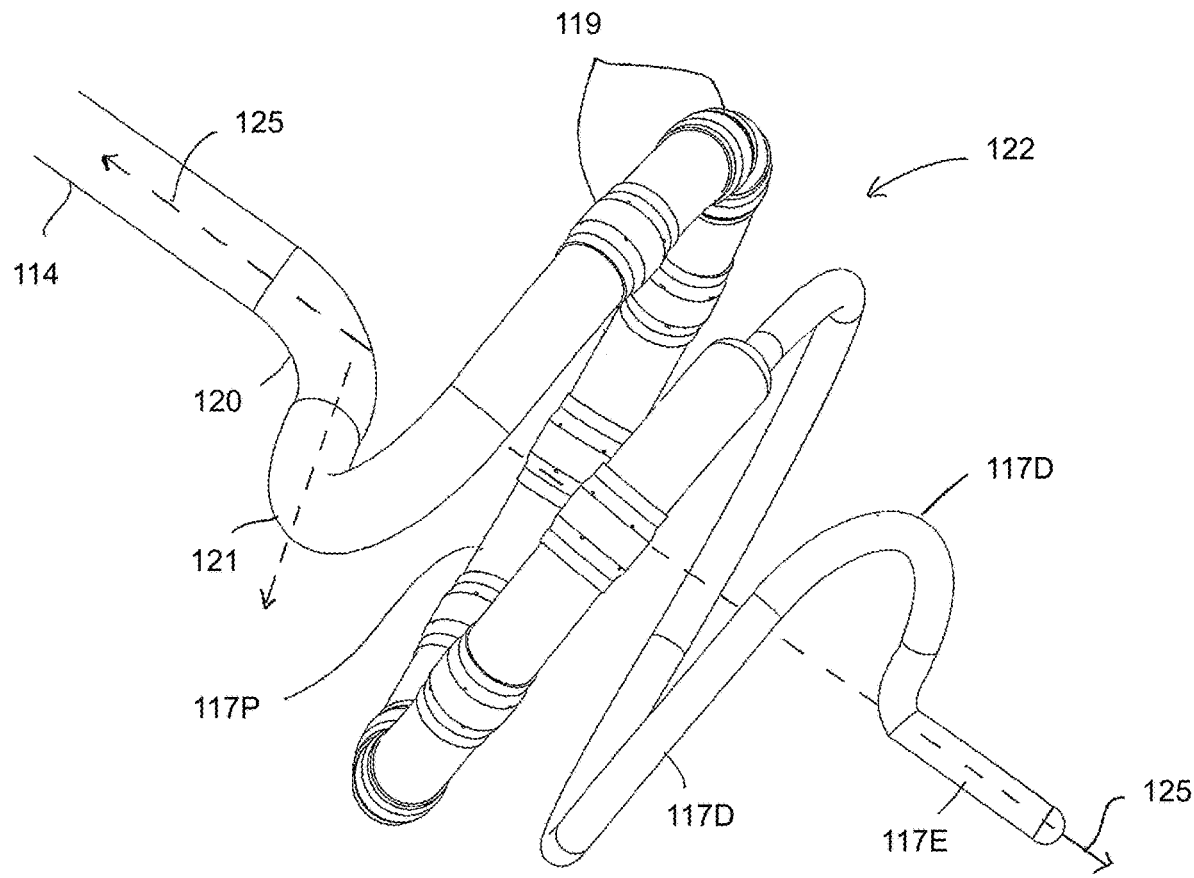
FIG. 11 is a detailed view of a distal assembly of the diagnostic catheter of FIG. 5.

One example of diagnostic catheter 110 used in this disclosure is shown in FIGS. 10-11 and includes lasso-type structures to facilitate maneuvering and positioning in the heart. Catheter 110 can be understood as including features more clearly described in Appendix 2 of U.S. 62/754,275 which includes U.S. Pat. Nos. 5,718,241; 6,198,974; 6,484,118; 6,987,995; 7,142,903; 7,274,957; 7,377,906; 7,591,799; 7,593,760; 7,720,517; 7,853,302; 8,000,765; 8,021,327; 8,275,440; and 8,348,888, each of which are incorporated by reference in their entirety as if set forth verbatim herein. Such catheters 110 can be used to produce curved, circular, looped or otherwise closed ablation paths, as well as sensing electrical activity along a curve, circle, loop or closed pattern for electrical potential and anatomical mapping.

Catheter 110 can therefore be an electrophysiological recording and stimulation of the atrial region of the heart and can be used in conjunction with catheter 24, as well as other ancillary equipment. Catheter 110's distal end can be a circular spine with ring electrodes located circularly and are used for stimulation and recording within the atria. The looped distal end is available in multiple diameters (15 mm, 20 mm and 25 mm) to achieve an optimal contact in variably sized pulmonary veins. In some examples, the loop tip can be a circular spine with ten electrodes bonded to its surface, a straight distal tip section and a hypotube shaft. The ten electrodes can be used for stimulation and recording within the atria of the heart and oriented circularly on the loop to achieve appropriate circumferential contact with the inside of the PV. Nominal electrode spacing can include 4.5 mm for the 15 mm loop, 6 mm for the 20 mm loop, and 8 mm for the 25 mm loop.

Catheter 110 according to the disclosed example can include an elongated body that can include an insertion shaft or catheter body 112 having a longitudinal axis, and an intermediate section 114 distal of the catheter body that can be uni- or bi-directionally deflected off axis from the catheter body longitudinal axis. A resilient three-dimensional distal assembly 117, with ring electrodes 119 disposed along a nonlinear or curved distal portion, extends from the elongated body 112 or the intermediate section 114. The helical form is oriented obliquely relative to a longitudinal axis 125 of the catheter 110 extending from the intermediate section 114. The term "obliquely", in this respect means that the plane P in space that best fits the helical form is angled relative to the longitudinal axis 125. An angle θ between the plane P and the axis 125 ranges between about 45 to 105 degrees, preferably between about 75 to 105 degrees, and more preferably about 90 degrees. Moreover, the helical form 122 of the distal assembly 117 spirals or subtends in a predetermined manner.

The distal assembly 117 can have an electrode-carrying proximal loop 117P, and a soft "pigtail" that includes a distal loop 117D and a distal straight end section 117E, wherein the distal' loop 117D and the distal straight end section 117E have a greater resiliency than the resiliency of the electrode-carrying proximal loop 117P. The pitch of the helical form 122 of the distal assembly 117 is selected to provide a gentle pressure for ensuring contact of all of ring electrodes 119 with tissue. It is understood that tapering of the helical form 122 ensures that the smaller distal loop 117D can fit into the tubular region or pulmonary vein which ensures placement of accuracy of the larger proximal loop 117P and the ring electrodes 119 carried thereon at an ostium 111 of the tubular region 113, e.g., a pulmonary vein. The greater flexibility of the distal loop 117D and the distal straight end section 117E provides an atraumatic leading element that guides distal assembly 117 into the tubular region or pulmonary vein and ensures placement accuracy of the distal assembly.

The catheter 110 enters a patient's body through a guiding sheath that has been inserted in a body cavity, such as a heart chamber. Due to the flexible construction of the distal assembly 117, the helical form 122 readily straightens for insertion into the guiding sheath. When exposed and unconstrained, the distal assembly 117 reassumes the helical form 122 which is maneuvered to engage the tissue surface frontally with some or all of the ring electrodes 119 on the proximal loop 117P contacting the tissue surface simultaneously.

Figure 12:
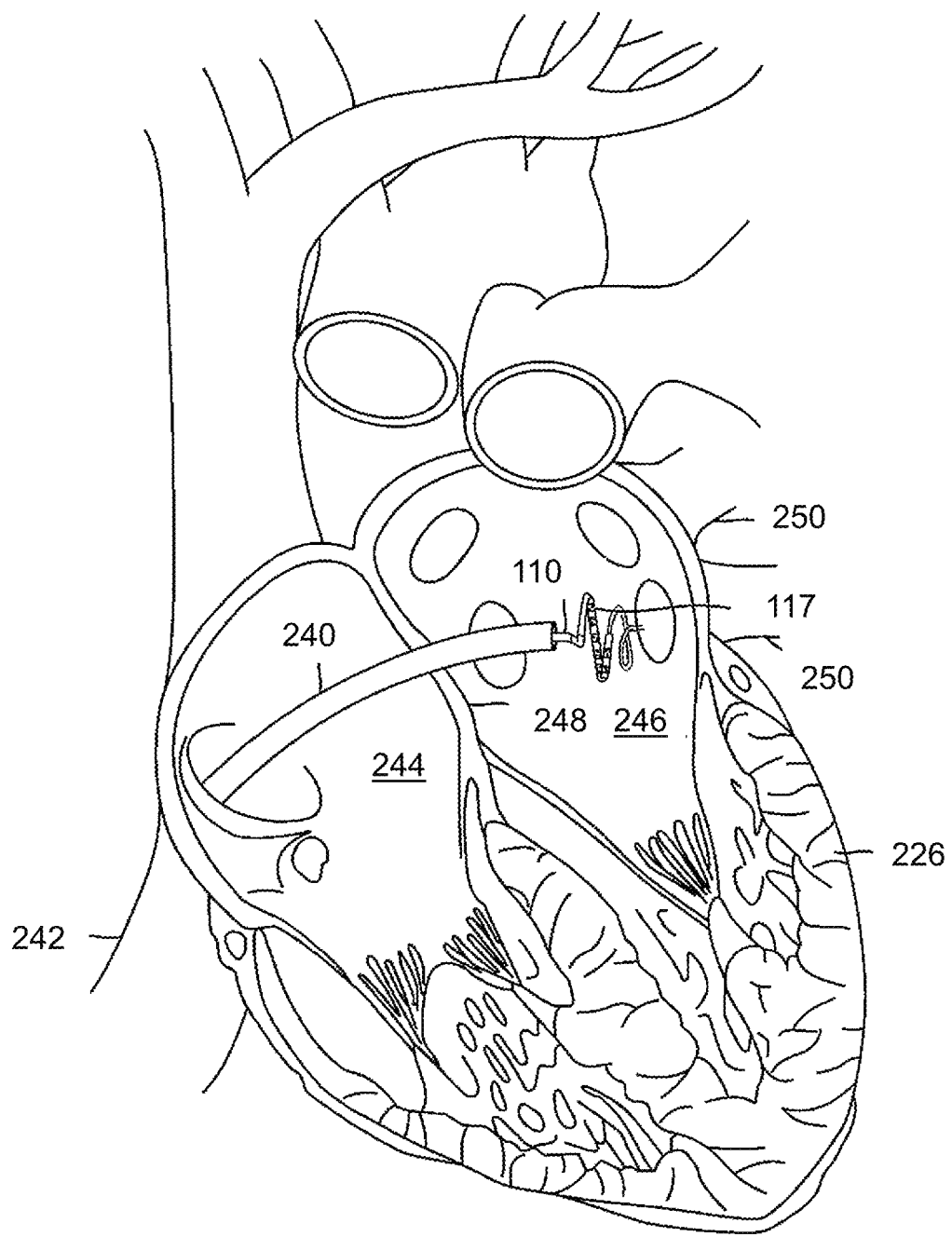
FIG. 12 is a schematic sectional view of a heart showing insertion of a diagnostic catheter according to FIGS. 10 and 11 and into the left atrium.

FIG. 12 is a schematic sectional view of heart 226, showing insertion of catheter 110 into the heart. To insert catheter 110, the user first passes a guiding sheath 240 percutaneously through the vascular system and into right atrium 244 of the heart through ascending vena cava 242. The sheath penetrates through interatrial septum 248, typically via the fossa ovalis, into left atrium 246. Alternatively, other approach paths can be used. Catheter 110 is then inserted through the guiding sheath until the distal assembly 117 of the catheter 110 extends past the distal end of the guiding sheath 240 into the left atrium 246.

Operator aligns the longitudinal axis of guiding sheath 240 (and of catheter 110) inside left atrium 246 with the axis of one of pulmonary veins. Alignment can be performed under fluoroscopic or other means of visualization. The user advances the catheter 110 distally toward the pulmonary vein so that the soft distal end 117E first enters the pulmonary vein, followed by the soft distal loop 117D, both of which guide the positioning and placement of the electrode-carrying proximal loop 117P onto the ostium. The user can apply a force F in the axial direction to press the proximal loop 117P onto the ostium to ensure contact between the ring electrodes 119 and the tissue.

The operator can rotate the catheter 110 about its axis within the guiding sheath 240 so that the proximal loop 117P traces an annular path around the inner circumference of the vein. Meanwhile, the user can actuate an RF generator to ablate the tissue in contact with the AR electrodes along the path. Simultaneously, impedance and/or PV potential recordings can be made with the IR and/or RR electrodes. After completing this procedure around one pulmonary vein, the user can shift the sheath 240 and catheter 110 and repeat the procedure around one or more of the other pulmonary veins.

Study Overview

Figure 13:
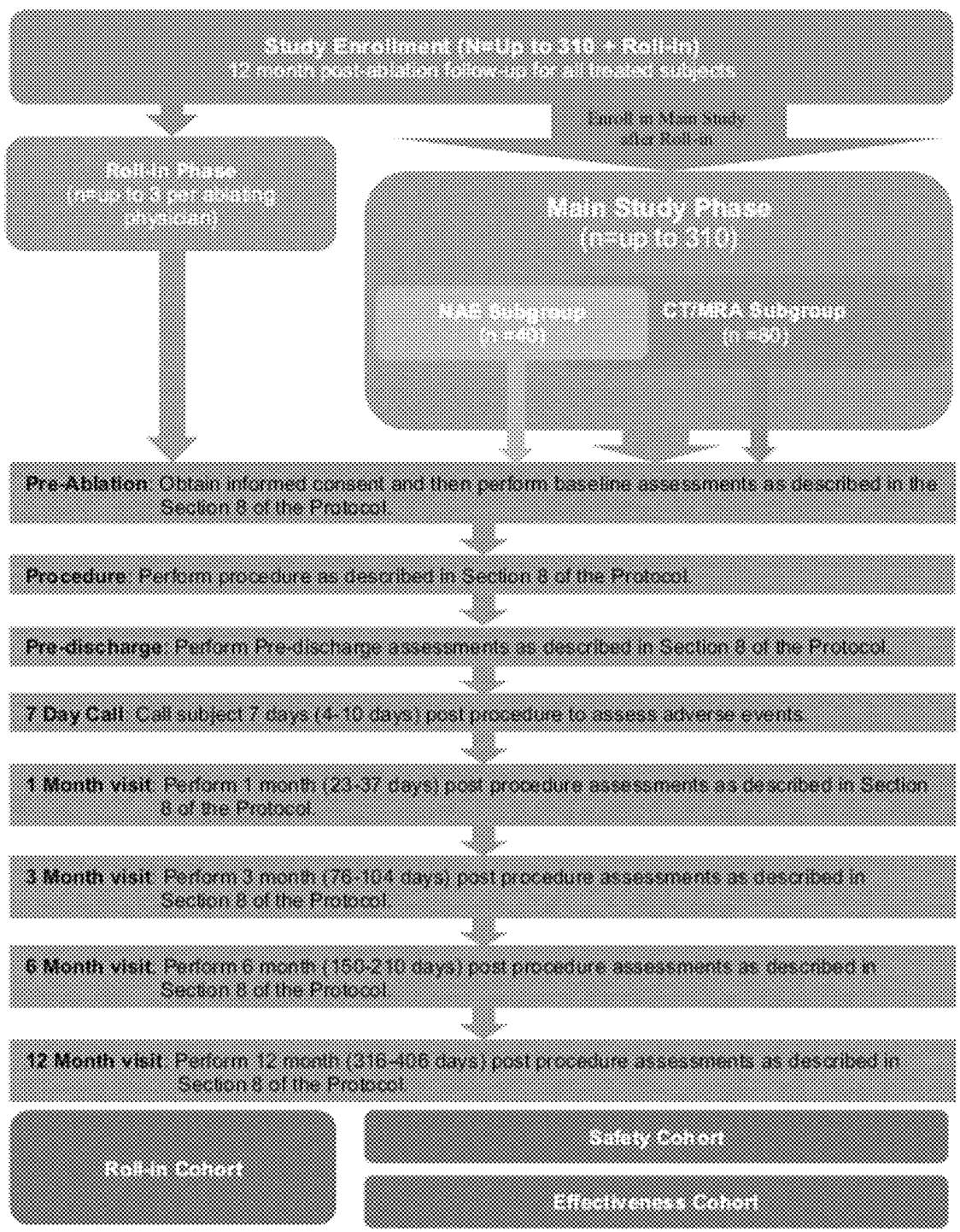
FIG. 13 shows a schematic overview of the study of this disclosure.

This disclosure is more clearly understood with a corresponding study discussed more particularly below with respect to treatment of PAF. FIG. 13 in particular provides a schematic overview of the subject study protocol of this disclosure as Appendix 3 and Appendix 4, each of which are incorporated by reference in their entirety as if set forth verbatim herein. The purpose of this study was to establish the overall safety and effectiveness of the catheter 24, in conjunction with the catheter 110 and multi-electrode RF generator, for the isolation of the atrial pulmonary veins in treatment of subjects with drug refractory, symptomatic, paroxysmal atrial fibrillation is clinically safe and clinically effective.

The study is a prospective, multicenter, single arm clinical evaluation utilizing catheters 24 and 110. The sample size for the study is primarily driven by the safety endpoint. An adaptive Bayesian design can be used to determine the sample size based on the safety endpoint alone. Sample size selection interim analyses can be performed when 80, 130, 180, and 230 evaluable subjects are enrolled in the main study (e.g., mITT Population). Safety outcome at 30 days will be used as a proxy for the primary safety endpoint at each interim. The final safety analysis is on complete follow-up for the primary safety endpoint for all evaluable patients in the main study. Predictive probabilities of success are used to determine whether the sample size at each interim analysis will be sufficient or if the trial enrollment will continue. Sample size simulations were performed using performance goals of 15% and 80% respectively for the safety and effectiveness endpoint rates.

At the time of each interim analysis, predictive probabilities of success are estimated using the available data from all evaluable subjects in the mITT population, assuming a non-informative uniform prior distribution for the primary safety rate. Enrollment is stopped if the predictive probability of trial success at any interim is greater than 90%, or if the predictive probability of trial success with the maximum sample size is less than a futility bound of 6.5%. Otherwise, enrollment continues until the next interim or the final sample size. Analysis of the effectiveness endpoint is performed at the final sample size determined for the safety endpoint. Power for the effectiveness endpoint assessment is >80% at all sample sizes N30 subjects.

The primary safety and effectiveness endpoints are evaluated using exact tests for binomial proportions at a one-sided 5% significance level.

In order to control for operational bias, the timing and results of the interim analyses are not revealed to study investigators unless an interim analysis results in a decision to stop enrollment. The interim analyses are conducted seamlessly with no interruption to study enrollment unless indicated by an interim analysis. The predicted probability of study success or summary results which are calculated at the time of the interim analysis is not disseminated by the statistician performing the interim analysis until the time of the final database lock for the CSR.

Analyses for primary effectiveness endpoint included null and alternative hypotheses, including Ho: PE<0.80 and Ha: PE>0.80. It is understood that primary effectiveness (PE) can mean proportion of patients with acute procedural success defined as confirmation of entrance block in treated PVs after adenosine and/or isoproterenol challenge (with or without the use of a focal catheter). The per-protocol population is used as the primary analysis population. Subjects with missing effectiveness endpoints data will be excluded in the primary analysis. Sensitivity analyses for missing data is performed using the PP and population to assess the impact of missing data on the primary effectiveness outcome and are described in the Statistical Analysis Plan (SAP).

With respect ablation parameters of the study, electrodes 33 of catheter 24 can make contact with the tissue due to the balloon 80 and length of the electrodes, which each helps in accommodating variable anatomy. The power needed to create a circumferential contiguous lesion in the ostium to the pulmonary vein is therefore less than that of other RF catheters. Power delivery from each electrode is regulated by the generator and is determined by user input and by the temperature read by the thermocouple located on the electrode.

When used with the catheter 24, the irrigation pump of the study delivered a continuous infusion of 5 mL/minute of room temperature heparinized saline (1 u heparin/1 mL saline) when not delivering RF current. To inflate the balloon and during ablation, the high flow setting was used to deliver 35 mL/minute. The recommended operating parameters for the catheter 24 are presented in FIG. 14.

The study duration is approximately 2.5 years; 1.5 years for the enrollment phase and an additional 1 year to complete follow-up. It is understood that data is presented herein for purposes of illustration and should not be construed as limiting the scope of the disclosed technology in any way or excluding any alternative or additional embodiments.

The study can demonstrate the clinical safety and acute effectiveness of the balloon catheter 24 when used with catheter 110 for the isolation of the atrial pulmonary veins in treatment of drug refractory Paroxysmal Atrial Fibrillation (PAF). Specifically, the study can demonstrate the clinical safety based on the incidence of early-onset (within 7 days of ablation procedure) primary adverse events (PAE). FIG. 15 shows a table summarizing intensity or severity of each AE assessed according to classifications. The study can also demonstrate the long term effectiveness based on the proportion of acute procedural success, whereby success in this context can be defined as confirmation of entrance block in treated pulmonary veins after adenosine and/or isoproterenol challenge, including subjects with or without the use of a focal ablation catheter and/or with freedom from documented AF/AT/Atypical (Left side) AFL episodes based on electrocardiographic data through the effectiveness evaluation period (day 91-365 post index procedure). Subjects with drug refractory, symptomatic PAF were enrolled and the patient population size included a maximum of 310 evaluable subjects (though fewer or more subjects could be investigated as needed or required, including populations such as 80, 130, and 180). Subjects can be evaluated prior to the procedure, prior to discharge, and post procedure at 7 days (4-10 days), 1 month (23-37 days), 3 months (76-104 days), 6 months (150-210 days), and 12 months (316-406 days).

The primary objective of the study was demonstrating the clinical safety and acute effectiveness of the balloon catheter 24 in conjunction with catheter 110, in the isolation of the atrial pulmonary veins in for the treatment of drug refractory PAF. Secondary objectives included to determine the early-onset (within 7 days), peri-procedural (30 day), and long-term (12 month) safety rates associated with the use of balloon catheter 24, the acute procedural success, defined as confirmation of entrance block in treated PVs after adenosine and/or isoproterenol challenge, of the balloon catheter 24 (with or without the use of a focal catheter). Also to evaluate Health Economics outcomes and Quality of Life (QoL) data for subjects treated with the balloon catheter 24, and to evaluate, within a subset of the Main Study population, the comparative incidence of pre-procedure and post-procedure symptomatic and asymptomatic cerebral emboli, as determined by MRI evaluations. The presence of emboli-associated neurological deficits was evaluated, using the NIHSS, mRS, and general neurological assessments.

Primary endpoints of the study include acute effectiveness and acute safety. Acute safety can include included incidence of early onset Primary Adverse Events (PAE) (within 7 days of an ablation procedure which used one or more of the investigational devices). Throughout this disclosure, it is understood that an adverse event (AE) is any untoward medical occurrence in a subject whether or not related to the investigational medical device. For purposes of this disclosure, an AE can be any undesirable experience (sign, symptom, illness, abnormal laboratory value, or other medical event) occurring to a subject during the course of the study, whether or not it is related to the device or procedure. Physical findings (including vital signs) observed at follow-up, or preexisting physical findings that worsen compared to baseline, are adverse events if the investigator determines they are clinically significant. As to the study, any medical condition present at the time that the subject is screened is considered as baseline and not reported as an AE. Such conditions should be added to background medical history, if not previously reported. However, if the study subject's condition deteriorates at any time during the study, it can be recorded as an AE.

Similarly, adverse events can be considered if any of the following apply: event is cardiovascular in nature, the event is a serious adverse event, causality is related to investigational device, ablation procedure, or unknown in nature. In contrast, the following clinical events were not considered an adverse event for this study: minor pericarditis attributable to the ablation procedure defined as pleuritic chest discomfort with or without pericardial rub and ECG changes, AF/AFL/AT recurrence requiring pharmacological or synchronized electrical cardioversion during the hospitalization for the index ablation procedure, or throughout the duration of the study. However, new onset of left atrial flutter occurring post-ablation is an AE, and re-ablation for AF or pre-existing AFL/AT itself is not an AE, however any procedural complication is considered an AE and shall be reported within the applicable timelines.

A serious adverse event (SAE) in this disclosure are those considered any event that meets one or more of the following criteria: leads to a death, leads to a serious deterioration in the health of a subject that resulted in a life-threatening illness or injury, a permanent impairment of a body structure or a body function, in-patient hospitalization or prolongation of an existing hospitalization, medical or surgical intervention to prevent life-threatening illness or injury or permanent impairment to body structure or a body function, leads to fetal distress, fetal death or a congenital abnormality or birth defect. It is understood that planned hospitalization for a condition present prior to the subject's enrollment in the study cannot meet the definition of an SAE. An AE would meet the criterion of "hospitalization" if the event necessitated an admission to a health care facility (e.g., an overnight stay). Emergency room visits that do not result in admission to the hospital were evaluated for one of the other serious outcomes. For further reference, FIG. 15 is provided summarizing classifications for the intensity or severity of each AE.

In the study, PAEs included the following AEs: device or procedure related death, Atrio-Esophageal Fistula, Myocardial Infarction, Cardiac Tamponade/Perforation, Thromboembolism Stroke/Cerebrovascular Accident (CVA), Transient Ischemic Attach (TIA), Phrenic Nerve Paralysis, Pulmonary Vein Stenosis, Pericarditis, Pulmonary Edema, Major Vascular Access Complication/Bleeding, and Hospitalization (initial or prolonged). In the study, events were considered as primary AEs even if they occur greater than one week (7 days) post-procedure. Events related to hospitalization were excluded solely due to arrhythmia recurrence or non-medically urgent cardioversion.

Secondary endpoints of the study as to safety included incidence of individual PAEs from the primary composite, incidence of Unanticipated (Serious) Adverse Device Effects (USADEs), incidence of Serious Adverse Events (SAEs) within 7 days (early-onset), >7-30 days (peri-procedural), and >30 days (late onset) of initial ablation procedure, incidence of non-serious adverse events, acute procedural success defined as confirmation of entrance block in treated pulmonary veins (PVs) after adenosine challenge (with or without the use of a focal catheter), pulmonary vein isolation (PVI) touch-up by focal catheter among all targeted veins and by subject during the index procedure, use of focal catheter ablation for non-PV triggers during the index procedure, freedom from documented AF/AT/Atypical (left-side) AFL episodes based on electrocardiographic data through the effectiveness evaluation period (day 91-365 post index procedure) off Class I and III AADs, average number of RF applications, and RF time, required to isolate common pulmonary veins, incidence of hospitalization for cardiovascular events (with hospitalization defined as prolonged stay ≥2 nights post standard index procedure or in-patient stay not concurrent with index procedure ≥1 calendar day), Health Economics data including but not limited to index procedure workflow costs, Quality of Life (QoL), and hospital cost, incidence of pre-procedure and post-ablation asymptomatic and symptomatic cerebral emboli as determined by MRI evaluations in Neurological Assessment Evaluable (NAE) subjects, frequency, anatomic location, and size (diameter and volume) of cerebral emboli by MRI evaluations at baseline, post-ablation and during follow-up (if new lesions observed) in NAE subjects, incidence of new or worsening neurologic deficits at baseline, post-ablation and follow-up in NAE subjects, Summary of National Institutes of Health Stroke Scale (NIHSS) and Modified Rankin Scale (mRS) scores at baseline, post-ablation and during follow-up, summary of MoCA scores at baseline, 1 month follow-up and during further follow-up, and hospitalization for cardiovascular events (hospitalization defined as prolonged stay nights post index procedure or in-patient stay not concurrent with index procedure 1 calendar day (if lesions were identified in prior evaluation) in NAE subjects.

Secondary endpoints of the study as to effectiveness included percentage (%) of PVI touch-up by focal catheter among all targeted veins and by subject; percentage (%) of subjects with use of focal catheter ablation for non-PV triggers; percentage (%) of subjects with freedom from documented, symptomatic atrial fibrillation (AF), atrial tachycardia (AT), or atypical (left side) atrial flutter (AFL) episodes (episodes >30 seconds on arrhythmia monitoring device from day 91 to 180); and percentage (%) of subjects with freedom from documented, atrial fibrillation (AF), atrial tachycardia (AT), or atypical (left side) atrial flutter (AFL) episodes (episodes >30 seconds on arrhythmia monitoring device from day 91 to 180).

Secondary endpoints of the study as to additional analyses on procedural characteristics, including but not limited to total procedure time, ablation time, RF application time, balloon dwell time, time to effect PVI, number and time of RF applications per PV location, and fluoroscopy time and dose.

Secondary endpoints of the study as to health economic assessments included index procedural workflow costs, hospital costs, and quality of life.

NAE safety endpoints include incidence of pre-procedure and post-ablation asymptomatic and symptomatic cerebral emboli as determined by MRI evaluations in NAE subjects; frequency, anatomic location, and size (diameter and volume) of cerebral emboli by MRI evaluations at baseline, post-ablation and during follow-up (if new lesions observed)

in NAE subjects; incidence of new or worsening neurologic deficits at baseline, post-ablation and follow-up in NAE subjects; and summary of NIHSS and mRS scores at baseline, post-ablation and during follow-up (if lesions were identified in prior evaluation) in NAE subjects.

Subjects enrolled in a NAE subgroup are assessed for incidences of symptomatic and asymptomatic pre-ablation and post-ablation cerebral emboli, with either an absence of neurological symptoms (asymptomatic) or with emboli-associated neurological symptoms (symptomatic). The NAE subgroup is a prospective design with consecutive enrollment. Roll-in subjects can NOT be eligible for the NAE subgroup. This approach minimizes the confounding influence of a learning curve during early use of a medical device. The sample size of 40 subjects in this subgroup can provide at least 95% probability of observing at least one event if the true ACE rate is greater than or equal to 8%. Enrollment in the NAE subgroup can be terminated prior to achieving the target 40 subjects if study enrollment ends early after a planned interim look.

Subjects enrolled in the Modified Intent-To-Treat (mITT) population included enrolled subjects meeting eligibility criteria and had the study catheter inserted. The safety population (SP) included all enrolled subjects who have undergone insertion of the study catheter. The Per Protocol (PP) Population was a subset of the mITT population and included subjects enrolled and meet all eligibility criteria, had undergone RF ablation with the study catheter, and had been treated for the study-related arrhythmia.

Primary effectiveness endpoints as to clinical effectiveness in the study was determined by those events where there was freedom from documented AF, atrial tachycardia (AT), or Atypical (left-side) atrial flutter (AFL) episodes (e.g., >30 seconds on arrhythmia monitoring device) based on electrocardiographic data through the effectiveness evaluation period (day 91-365 post index procedure). Additionally, if a subject met any one of the following criteria, then the subject was considered as chronic effectiveness failure: Acute procedural failure (i.e., failure to confirm entrance block in clinically relevant pulmonary veins post-procedure), repeat ablation or surgical treatment for AF/AT/Atypical (left-side) AFL after the blanking period (after day 90 post index procedure), DC cardioversion for AF/AT/Atypical (left-side) AFL after the blanking period (after day 90 post index procedure), continuous AF/AT/AFL on a standard 12-lead ECG even if the recording is less than 30 seconds in duration (after day 90 post index procedure), a new Class I and/or Class III AAD is prescribed for AF during effectiveness evaluation period (e.g., day 91-365 post index procedure) or prescribed during the blanking period and continued past 90 days, a previously failed Class I and/or Class III AAD (failed at or before screening) was taken for AF at a greater dose than the highest ineffective historical dose during the effectiveness evaluation period (e.g., day 91-365 post index procedure), and amiodarone was prescribed post index ablation procedure.

During this study, current AF management guidelines and the institution's standard of care practices are followed as closely as possible for AAD therapy. FIG. 16 shows a table illustrating classifications based on AAD therapy administered in the blanking and post-blanking periods in the study.

It is understood that prior to the procedure, uninterrupted anticoagulation therapy was in place at least 1 month prior to the ablation procedure. If receiving warfarin/coumadin therapy, subjects had an international normalized ratio (INR) ≥2 for at least 3 weeks prior to treatment and the subject's must be confirmed to be ≥2 within 48 hours pre-procedure. Any INR<2 within 3 weeks prior to ablation was understood to lead to exclusion of the subject or postponement of the study procedure until the INR is ≥2 for at least 3 weeks prior to treatment.

Anticoagulation therapy was not interrupted or stopped prior to the procedure (e.g., no doses should be missed or omitted) and daily regimen was continued. During the procedure, a heparin bolus was administered prior to transseptal puncture an ACT of 350-400 was targeted seconds prior to inserting the balloon 80 and throughout the procedure. ACT levels were checked every 15-30 minutes during the procedure to ensure an ACT target of 350-400 seconds. All recordings (ACT level, timing of heparin administration and dose) were documented in the medical records as source documentation. All tubing and sheath was continuously flushed with heparinized saline.

After the procedure, anticoagulation therapy was strongly recommended for at least 2 months following ablation. Additional medications needed to treat clinical indications were at the discretion of the clinical investigation physician AAD management during the study was at the discretion of the investigator.

Secondary effectiveness endpoints included acute procedural success defined as confirmation of entrance block in treated PVs after adenosine challenge (with or without the use of a focal catheter), PVI touch-up by focal catheter among all targeted veins and by subject during the index procedure, use of focal catheter ablation for non-PV triggers during the index procedure, freedom from documented symptomatic AF/AT/Atypical (left-side) AFL episodes based on electrocardiographic data through the effectiveness evaluation period (day 91-365 post index procedure) off Type I and III antiarrhythmic drugs (AADs), and average number of RF applications, and RF time, required to isolate common pulmonary veins.

Patient Selection

The criteria for patient selection, method or uses, personnel, facilities, and training specified in this study were intended to minimize the risk to subjects undergoing this procedure.

Patients were prescreened carefully prior to enrollment in the study to ensure compliance with the inclusion and exclusion criteria. The risk of PNP was minimized by monitoring the PN with pacing maneuvers before the ablation. Ablation was stopped immediately if evidence of PN impairment is observed, and the balloon can be repositioned. The risk of PV stenosis can be minimized by not positioning the balloon within the tubular portion of the target PV. The balloon should not be inflated while the catheter is positioned inside the pulmonary vein; rather, it is always to be inflated in the atrium, then positioned at the PV ostium.

The risk of an embolus in the study was reduced by quickly terminating the application of current after an impedance rise, which limits the size of the coagulum on the electrode. It has been observed that thrombi can form on the transseptal sheath almost immediately after crossing the septum. Optimal anti-coagulation, using Heparin to achieve an ACT of 350 seconds, during procedure and early Heparin administration, prior to transseptal puncture, can substantially decreases the risk. This risk can be reduced by the use anticoagulant therapy, at the discretion of the investigator.

The risk of ACE can be minimized by implementing an anti-coagulation regimen prior to balloon introduction into the left atrium and during procedure to avoid thrombi/emboli during procedure. Investigators are instructed to remove air bubbles and to minimize catheter exchange during procedure to mitigate the of risk air introduction. A single transseptal technique, with administration of heparin bolus prior to transseptal puncture, is also implemented. In order to help prevent esophageal injury, intraluminal esophageal temperature monitoring is required for the study to ensure the physician has accurate information about the location of the esophagus relative to intended sites of ablation.

Following procedures, all subjects are maintained on systemic oral anticoagulation therapy for at least two months post-procedure, beginning within 6 hours post-procedure. After two-months post-procedure, a decision regarding continuation of systemic anti-coagulation agents is made based on the subject's risk for thromboembolism. Systemic oral anticoagulation can be continued beyond two-months post-ablation in subjects with $CHA_2DS_2$-VASc score ≥2.

For each included patient, age, gender and cardiovascular risk factors (e.g., diabetes mellitus, obesity, smoking, high blood pressure, hyperlipidemia) were recorded. Initial imaging was brain CT with cervical and intracranial angiography or brain MRI with time of flight angiography, depending on hospital protocol. The ASPECT (Alberta Stroke Program Early CT) score was evaluated by experienced neuroradiologists on either modality, and the NIHSS score by neurologists. Patients were treated up to 12 hours from time of stroke onset or time last known well in case of wake-up stroke.

Inclusion criteria for the study included the following:
Diagnosed with Symptomatic PAF;
Selected for AF ablation procedure for pulmonary vein isolation; Able and willing to comply with uninterrupted per-protocol
Diagnosed with Symptomatic PAF, including at least three (3) symptomatic episodes of AF with attacks lasting ≥1 minute) within six (6) months prior to enrollment, and at least one (1) AF episode must be electrocardiographically documented within twelve (12) months prior to enrollment. Electrocardiographic documentation can include, but is not limited to, electrocardiogram (ECG), Holter monitor, or telemetry strip;
Failing at least one (1) Class I or Class III AAD as evidenced by recurrent symptomatic AF or intolerable side effects to the AAD;
Willingness to comply with anticoagulation requirements (e.g., warfarin, rivaroxaban, dabigatran, apixaban);
Age 18-75 years; and
Able and willing to comply with all pre-procedure, post-procedure, and follow-up testing and visit requirements.
Exclusion criteria for the study included the following:
AF secondary to electrolyte imbalance, thyroid disease, or reversible or non-cardiac cause;
Previous surgical or catheter ablation for AF;
Patients known to require ablation outside the PV ostia and CTI region (e.g. AVRT, AVNRT, atrial tachycardia, VT and WPW);
Previously diagnosed with persistent or long-standing persistent AF and/or Continuous AF>7 days, or >48 hrs terminated by cardioversion;
Any percutaneous coronary intervention within the past 2 months;
Valve repair or replacement or presence of a prosthetic valve;
Any carotid stenting or endarterectomy within the past 6 months;
Any carotid stenting or endarterectomy;
Coronary artery bypass grafting (CABG), cardiac surgery (e.g. ventriculotomy, atriotomy), or valvular cardiac surgical or percutaneous procedure within the past 6 months;
Documented left atrium (LA) thrombus within 1 day prior to the index procedure;
LA antero posterior diameter >50 mm;
Any PV with a diameter 26 mm
Left Ventricular Ejection Fraction (LVEF)<40%;
Contraindication to anticoagulation (e.g. heparin);
History of blood clotting or bleeding abnormalities;
Myocardial infarction within the past 2 months;
Documented thromboembolic event (including transient ischemic attack) within the past 12 months;
Rheumatic Heart Disease;
Uncontrolled heart failure or New York Heart Association (NYHA) function class III or IV;
Awaiting cardiac transplantation or other cardiac surgery within the next 12 months;
Unstable angina;
Acute illness or active systemic infection or sepsis;
Diagnosed atrial myxoma or presence of an interatrial baffle or patch;
Presence of implanted pacemaker or implantable cardioverter defibrillator (ICD), or tissue-embedded, iron-containing metal fragments);
Significant pulmonary disease, (e.g. restrictive pulmonary disease, constrictive or chronic obstructive pulmonary disease) or any other disease or malfunction of the lungs or respiratory system that produces chronic symptoms;
Significant congenital anomaly or medical problem that, in the opinion of the investigator, would preclude enrollment in this study;
Women who are pregnant (as evidenced by pregnancy test if pre-menopausal), lactating, or who are of child bearing age and plan on becoming pregnant during the course of the clinical investigation;
Enrollment in an investigational study evaluating another device, biologic, or drug;
Has known pulmonary vein stenosis;
Presence of intramural thrombus, tumor or other abnormality that precludes vascular access, or manipulation of the catheter;
Presence of an inferior vena cava filter;
Presence of a condition that precludes vascular access;
Life expectancy or other disease processes likely to limit survival to less than 12 months;
Presenting contra-indication for the devices (e.g. TTE, CT, etc.) used in the study, as indicated in the respective instructions for use;
Categorized as a vulnerable population and requires special treatment with respect to safeguards of well-being
Additional exclusion criteria for Neurological Assessment Evaluable (NAE) subjects include contraindication
Patient on amiodarone at any time during the past 3 months prior to enrollment;
Contraindication to use of contrast agents for MRI such as advanced renal disease;
Presence of iron-containing metal fragments in the body; and
Unresolved pre-existing neurological deficit.

Results of the Study

In the study, 95 patients were treated. Patients (age 60.3±9.81 yrs, 64.2% male) underwent PVI at 6 centers using a multielectrode RF balloon catheter (RFB). Eight subjects were enrolled as part of the roll-in phase. Main population consisted of 87 subjects of whom two were considered to be ineligible, resulting in an evaluable cohort of 85 subjects. Acute success, a primary effectiveness endpoint of the study, was defined as sustained PV entrance block upon Adenosine/Isoproterenol challenge. Single-shot success was defined as PVI before adenosine challenge with one valid 60 second ablation. Time to isolation was the observed RF ablation time to reach a pure single-shot success. Recurrence of symptomatic AF/AT/AFL was documented with weekly transtelephonic monitoring from 3-6 months, and Holter monitoring at 6 months.

During the study, investigators collected the following data: RF ablation parameters per PV, number of RF application(s) per target PV, number of RF application(s) required with a focal catheter (if applicable), total RF duration per target PV, total time of RF application with the balloon catheter 24 until PV isolation of targeted vein was achieved (TTI=time to isolate), total time of RF application with the focal catheter (if applicable), PV acute reconnection, RF ablation parameters per application, Targeted vein, Ablation number of the generator, Total Duration of RF energy per application, Balloon Inflation Index prior to target PV application, Identification of posterior and/or pacing electrodes, Ablation parameters (impedance, temperature, power, number of active electrodes per application, and total duration of RF application. Also, RF duration of posterior/anterior electrode, etc.) can be collected during the ablation procedure via the generator log files, ablation parameters, PV isolation information, including but not limited to percentage of targeted PV isolated on first shot, RF application and percentage of targeted PV with acute reconnection on adenosine (ATP) and/or isoproterenol challenge, procedural parameters, including but not limited to: Duration of time in mapping (LA and PVs), Total RF duration (consecutive time of RF energy delivered by multi-electrode RF balloon catheter and focal catheter (if applicable)), Total PVI time with balloon catheter (Duration of time from $1^{st}$ RF application to final RF application), Total PVI time with focal catheter (if applicable), Total procedure time (from first femoral puncture to catheter removal), Total fluoroscopy time and dose, Total Balloon dwell time (from first RF balloon insertion until RF balloon removal), ECG data, Total fluid delivered via ablation catheter, Total fluid delivered via intravenous line (if captured), Fluid output (if captured), Net Fluid input, ACT level and timepoint of heparin administration, Strategy to evaluate the proximity to the phrenic nerve, Strategy used to minimize risk of esophageal injury, Type of temperature probe, cut-off temperature and any abnormal increases in temperature observed.

Figure 17:
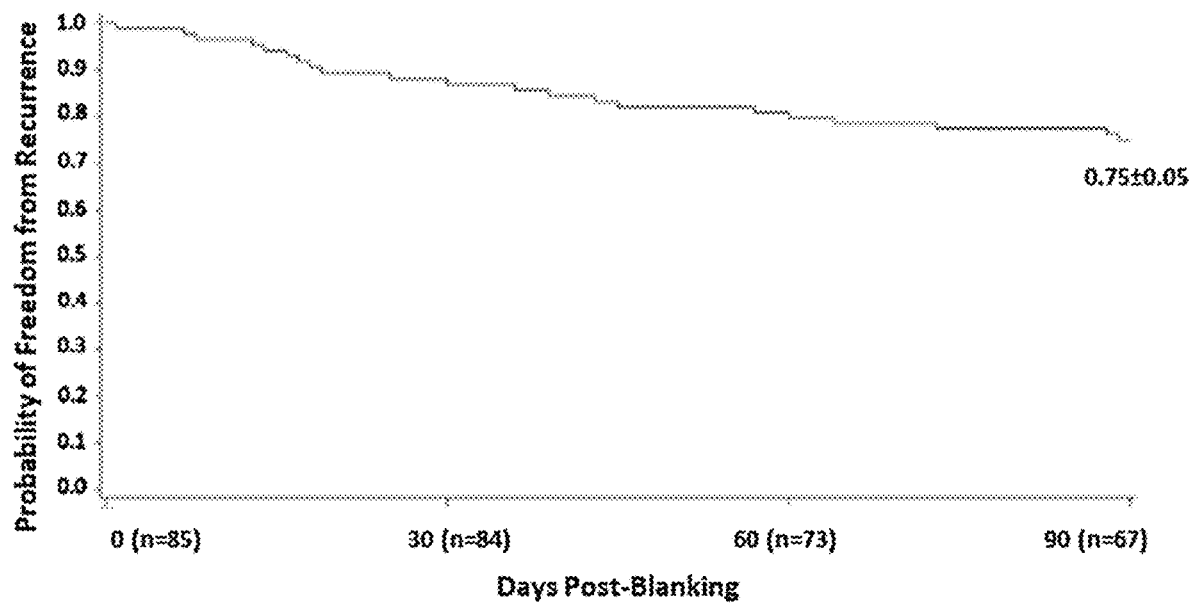
FIG. 17 shows example information from the study of this disclosure.

Ablation procedures were performed under general anesthesia in 47/87 (54.0%) subjects, and under conscious sedation in 40/87 (45.9%) subjects. One primary AE (retroperitoneal bleed) occurred in 1/85 (1.2%) patient. Acute success was achieved in all 82 evaluable pts (100%) undergoing Aden/Iso challenge; 3 pts did not receive Aden/Iso challenge and were excluded from this analysis. Single-shot successes were 74.7%, 57.9%, 72.3%, and 68.7% for the LIPV, LSPV, RIPV, and RSPV. Time to isolation per vein was 8.2±4.95, 10.6±7.71, 8.7±4.70 and 8.8±6.45 sec for the LIPV, LSPV, RIPV, and RSPV, respectively. Ablations were performed with procedure time 87.6±22.25 min, RF time 6.1±2.37 min, with 7.5±3.25 RF applications, RFB LA dwell time 40.3±16.69 min, and fluoroscopy time 10.9±9.12 min. After the first roll-in cases, the total procedure and fluoroscopy times decreased to 76.0 min and 10.5 min. The Kaplan-Meier estimate of freedom from documented symptomatic AF/AT/AFL recurrence at 6 months was 80.9% (standard error [SE], 4.3% as shown in FIG. 17).

In a prior study feasibility study using the multi-electrode balloon catheter of this disclosure that included 40 enrolled patients, enrolled patients were similarly screened for silent cerebral lesions (SCL), also known as ACE. A secondary analysis of the results of the first study of this disclosure and the prior study evaluated the impact of certain ablation workflow modifications on the incidence of SCL following PVI with the herein described multi-electrode RF balloon catheter in patients with symptomatic PAF.

In the prior study, the ablation workflow included (1) irrigation flow rate during RF application: 35 mL/minute, (2) maximum power setting: 15 W, (3) maximum temperature setting: 65° C. (maximum temperature lowered to 60° C. after 7 patients), (4) maximum application time anterior electrodes: 60 seconds, and (5) maximum application time posterior electrodes: 20 seconds.

In contrast, the first study of this study included an ablation workflow as follows: (1) eliminating dual transseptal access, (2) using an over-the-wire mini lasso, (3) continuously irrigating all side ports, (4) bolus dosing with heparin before trans-septal puncture, (5) maintaining activated clotting time (ACT) at 350 to 400 seconds, and (6) maximum temperature setting: 55° C. An example ablation workflow for the first study of this disclosure is shown in FIG. 18.

Analyses of MRI data were performed in the neurologic assessment—evaluable (NAE) analysis population, which included all enrolled patients who met eligibility criteria, had catheter 24 of this disclosure inserted, received RF energy, completed the pre- and post-ablation brain MRI examinations, and completed ≥1 post-ablation neurologic assessment. Incidences of SCL were evaluated using diffusion-weighted MRI 72 hours prior to the ablation procedure, as well as within 48 hours post-procedure.

Figure 19A:
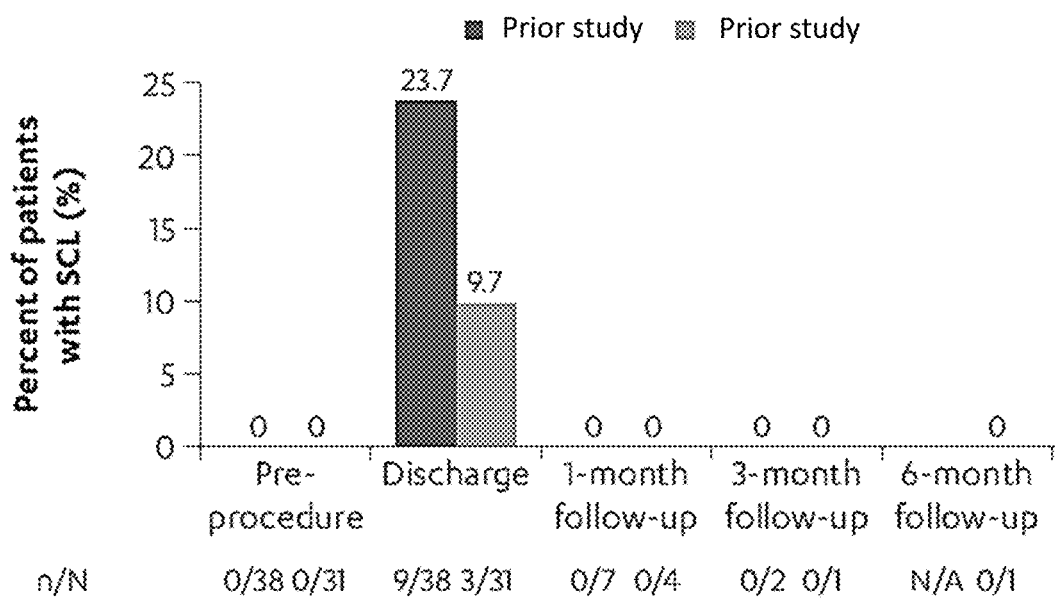
FIG. 19A shows a graph summarizing silent cerebral lesions by visit from the first study of this disclosure compared with a prior study.
Figure 19B:
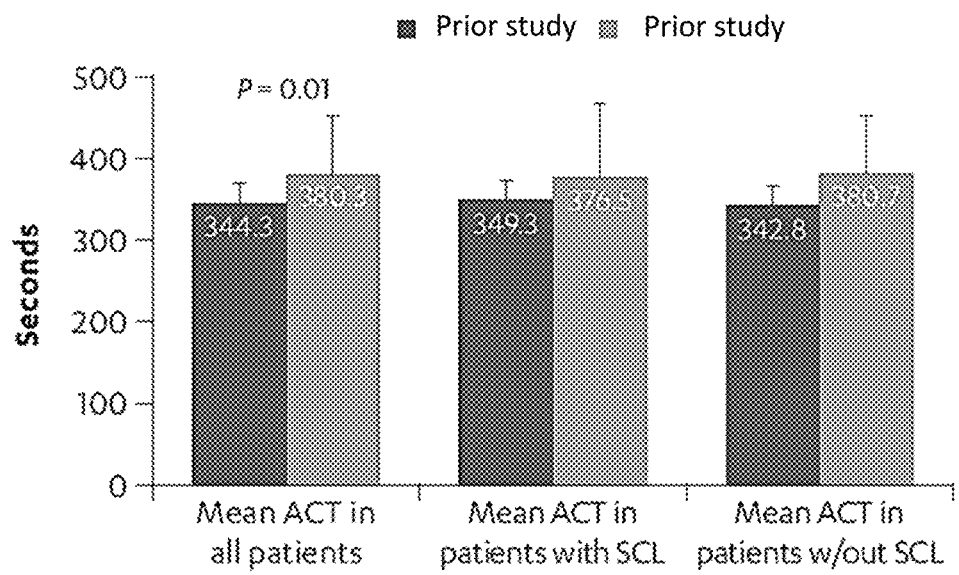
FIG. 19B shows a graph summarizing mean activated clotting time in patients with and without silent cerebral lesion from the first study of this disclosure compared with a prior study.

In the prior study and the first study, patients with identifiable lesions or neurologic symptoms had a follow-up MRI to determine lesion progress, until lesions were resolved. The anatomic location and size (diameter and volume) of SCL determined by MRI evaluations were also recorded. All patients underwent neurologic and cognitive assessments, including NIHSS assessments. In the NAE populations of the 2 studies, the prior study (N=38) and the first study (N=31), mean (standard deviation) ages were 60.8 (10.04) and 59.3 (8.08) years, respectively, and 57.9% and 71.0% of patients, respectively, were male, as shown in FIG. 18. SCL incidences at discharge were 23.7% (10 lesions in 9 patients) in the prior study and 9.7% (3 lesions in 3 patients) in the first study of this disclosure as seen in FIG. 19A. FIG. 19B in contrast shows a graph summarizing mean activated clotting time in patients with and without silent cerebral lesion from the first study of this disclosure compared with a prior study.

In the depicted results, it can be seen that modifications to the ablation workflow between the prior study and the first study of this disclosure led to a substantially lower incidence of SCL following PAF ablation using the RF balloon catheter of this disclosure. These reductions in the incidence of SCL were accompanied by a lower incidence of minor stroke. In addition, patients in the first study had higher ACT than patients in the prior study. Taken together, these results suggest that the modifications to the ablation workflow, including stringent anticoagulation control, eliminating dual trans-septal access, and reducing the maximum temperature setting to 55° C., in the first study contributed to lower incidence of SCL.

FIG. 20 depicts a method or use 2000 for administering a procedure for treating atrial fibrillation. The method or use 2000 can include 2010 delivering a multi-electrode radiofrequency balloon catheter to one or more targeted pulmonary veins; 2020 ablating tissue of the pulmonary vein using the multi-electrode radiofrequency balloon catheter; and 2030 achieving a predetermined effectiveness rate of pulmonary vein isolation.

FIG. 21 depicts a method or use 2100 for administering a procedure for treating atrial fibrillation. The method or use 2100 can include 2110 delivering a multi-electrode radiofrequency balloon catheter to one or more targeted pulmonary veins; 2120 ablating tissue of the pulmonary vein using the multi-electrode radiofrequency balloon catheter; and 2130 achieving a predetermined success rate of pulmonary vein isolation.

FIG. 22 depicts a method or use 2200 for administering a procedure for treating atrial fibrillation. The method or use 2200 can include 2210 delivering a multi-electrode radiofrequency balloon catheter to one or more targeted pulmonary veins; 2220 ablating tissue of the pulmonary vein using the multi-electrode radiofrequency balloon catheter; and 2230 achieving pulmonary vein isolation and at least a 97% safety endpoint within seven (7) days of successful pulmonary vein isolation.

FIG. 23 depicts a method or use 2300 for administering a procedure for treating atrial fibrillation. The method or use 2300 can include 2310 delivering a multi-electrode radiofrequency balloon catheter to one or more targeted pulmonary veins; 2320 ablating tissue of the pulmonary vein using the multi-electrode radiofrequency balloon catheter; and 2330 achieving pulmonary vein isolation and at least a 90% safety endpoint within seven (7) days of successful pulmonary vein isolation.

FIG. 24 depicts a method or use 2400 to treat a plurality of patients for paroxysmal atrial fibrillation. The method or use 2400 can include delivering a multi-electrode radiofrequency balloon catheter having a plurality of independently controllable electrodes for radiofrequency ablation and a multi-electrode diagnostic catheter to one or more targeted pulmonary veins; 2420 ablating tissue of the one or more targeted pulmonary veins with one or more of the plurality of the electrodes independently controlled multi-electrode radiofrequency balloon catheter; 2430 diagnosing the one or more targeted pulmonary veins using the multi-electrode diagnostic catheter; and 2440 achieving at least one of a predetermined clinical effectiveness and acute effectiveness of the method or use based on use of the multi-electrode radiofrequency balloon catheter and the multi-electrode diagnostic catheter in the isolation of the one or more targeted pulmonary veins.

FIG. 25 depicts a method or use 2500 to treat a plurality of patients for paroxysmal atrial fibrillation. The method or use 2500 can include 2510 delivering a multi-electrode radiofrequency balloon catheter having a plurality of independently controllable electrodes for radiofrequency ablation and a multi-electrode diagnostic catheter to one or more targeted pulmonary veins; 2520 ablating tissue of one or more targeted pulmonary veins with one or more of the plurality of the electrodes independently controlled multi-electrode radiofrequency balloon catheter; 2530 diagnosing all targeted pulmonary veins using the multi-electrode diagnostic catheter; and 2540 achieving a predetermined rate of adverse events based on use of the multi-electrode radiofrequency balloon catheter and the multi-electrode diagnostic catheter in the isolation of all targeted pulmonary veins, during and approximately 6 months after the method or use.

Figure 26:
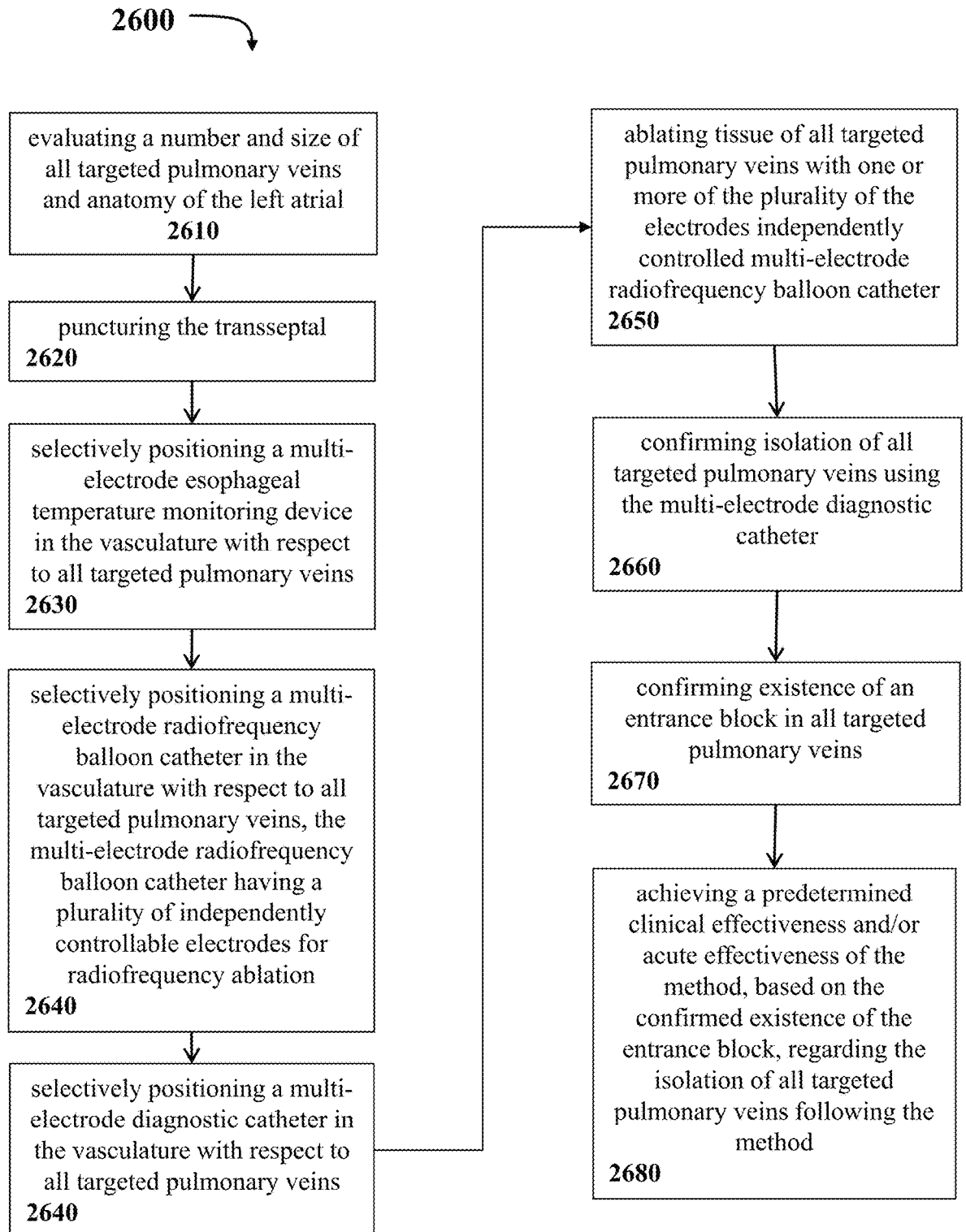
FIG. 26 depicts a graphical overview of one method or use according to this disclosure.

FIG. 26 depicts a method or use 2600 to treat a plurality of patients for paroxysmal atrial fibrillation. The method or use 2600 can include 2610 evaluating a number and size of all targeted pulmonary veins and anatomy of the left atrial; 2620 puncturing the transseptal; 2630 selectively positioning a multi-electrode esophageal temperature monitoring device in the vasculature with respect to all targeted pulmonary veins; 2640 selectively positioning a multi-electrode radiofrequency balloon catheter in the vasculature with respect to all targeted pulmonary veins, the multi-electrode radiofrequency balloon catheter having a plurality of independently controllable electrodes for radiofrequency ablation; 2650 ablating tissue of all targeted pulmonary veins with one or more of the plurality of the electrodes independently controlled multi-electrode radiofrequency balloon catheter; 2660 confirming isolation of all targeted pulmonary veins using the multi-electrode diagnostic catheter; 2670 confirming existence of an entrance block in all targeted pulmonary veins; and 2680 achieving a predetermined clinical effectiveness and/or acute effectiveness of the method or use, based on the confirmed existence of the entrance block, regarding the isolation of all targeted pulmonary veins following the method or use.

FIG. 27 depicts a method 2700 to treat a plurality of patients for paroxysmal atrial fibrillation. The method 2700 can include 2710 administering a heparin bolus prior to transseptal puncture; 2720 providing transseptal access for a multi-electrode radiofrequency balloon catheter and a mapping catheter across a septum; 2730 using a lasso catheter for at least one septum puncture; 2740 irrigating, by the balloon catheter, continuously at or about all targeted veins; 2750 confirming activated clotting time between approximately about 350 and 400 seconds prior to inserting the balloon catheter into a left atrium; and 2760 performing pulmonary vein ablation with the balloon catheter with a maximum temperature setting of the balloon catheter being approximately about 55° C. thereby achieving at least one of a predetermined clinical effectiveness and acute effectiveness of the multi-electrode radiofrequency balloon catheter in the isolation of the targeted pulmonary veins, during and approximately 3 months after ablation.

The method or uses, systems, and devices of this disclosure demonstrated high rates of substantial clinical effectiveness and safety in patients suffering from PAF. The specific configurations, choice of materials and the size and shape of various elements can be varied according to particular design specifications or constraints requiring a system or method or use constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

The following clauses list non-limiting embodiments of the disclosure:

1. A method or use to treat a plurality of patients for paroxysmal atrial fibrillation, the method or use comprising the steps of:

delivering a multi-electrode radiofrequency balloon catheter having a plurality of independently controllable electrodes for radiofrequency ablation and a multi-electrode diagnostic catheter to one or more targeted pulmonary veins;

ablating tissue of the one or more targeted pulmonary veins with one or more of the plurality of the electrodes independently controlled multi-electrode radiofrequency balloon catheter;

diagnosing the one or more targeted pulmonary veins using the multi-electrode diagnostic catheter; and achieving at least one of a predetermined clinical effectiveness and acute effectiveness of the multi-electrode radiofrequency balloon catheter and the multi-electrode diagnostic catheter in the isolation of the one or more targeted pulmonary veins, during and approximately 3 months after the ablating step.

2. The method or use of clause 1, wherein acute effectiveness is defined by confirming if there is an entrance block in all targeted pulmonary veins after adenosine and/or isoproterenol challenge.

3. The method or use of clause 2, further comprising: determining the acute effectiveness determined at approximately 3 months after the ablating step; and generating an estimated acute effectiveness at approximately 12 months after the ablating step based on the acute effectiveness determined at approximately 3 months.

4. The method or use of clause 3, wherein the estimated acute effectiveness at approximately 12 months is substantially similar to the acute effectiveness determined at approximately 3 months.

5. The method or use of clause 2, wherein the acute effectiveness is further defined by success greater than 90% for the plurality of patients.

6. The method or use of clause 2, wherein the acute effectiveness is further defined by success greater than 95% for the plurality of patients.

7. The method or use of clause 2, wherein a Type-1 error rate for power the acute effectiveness and the clinical effectiveness of all targeted veins are controlled at approximately a 5% level, the method or use further comprising:

determining whether the ablating is clinically successful for the plurality of patients if both the acute effectiveness and the clinical effectiveness indications are controlled at approximately the 5% level.

8. The method or use of clause 2, wherein the acute effectiveness is at least 80% for the plurality of patients being at least 80 patients.

9. The method or use of clause 2, wherein the acute effectiveness is at least 80% for the plurality of patients being at least 130 patients.

10. The method or use of clause 2, wherein the acute effectiveness is at least 80% for the plurality of patients being at least 180 patients.

11. The method or use of clause 2, wherein the acute effectiveness is at least 80% for the plurality of patients being at least 230 patients.

12. The method or use of clause 2, wherein the acute effectiveness is further defined by confirming if there is an entrance block in all targeted pulmonary veins after adenosine and/or isoproterenol challenge using a focal ablation catheter.

13. The method or use of clause 2, wherein the acute effectiveness is further defined by confirming if there is an entrance block in all targeted pulmonary veins after adenosine and/or isoproterenol challenge without using a focal ablation catheter.

14. The method or use of clause 1, wherein the ablating is administered on the plurality of patients diagnosed with symptomatic paroxysmal atrial fibrillation.

15. The method or use of clause 1, wherein the step of diagnosing further comprises:

electrophysiological mapping of the heart.

16. The method or use of clause 1, wherein the multi-electrode diagnostic catheter further comprises a high torque shaft with a halo-shaped tip section containing a plurality of pairs of electrodes visible under fluoroscopy.

17. The method or use of clause 1, wherein the plurality of patients is at least 80.

18. The method or use of clause 1, wherein the plurality of patients is at least 130.

19. The method or use of clause 1, wherein the plurality of patients is at least 180.

20. The method or use of clause 1, wherein the plurality of patients is at least 230.

21. The method or use of clause 1, wherein the predetermined acute effectiveness is defined by ulceration being absent in the plurality of patients after the ablating.

22. The method or use of clause 1, wherein the predetermined acute effectiveness is defined by a complication rate of approximately 13% or fewer of the plurality of patients experiencing esophageal erythema after the ablating.

23. The method or use of clause 1, wherein the predetermined acute effectiveness is defined by a complication rate of approximately 25% or fewer of the plurality of patients experiencing new asymptomatic cerebral embolic lesions after the ablating.

24. The method or use of clause 1, wherein the predetermined acute effectiveness is defined by a complication rate of approximately 20% or fewer of the plurality of patients experiencing new asymptomatic cerebral embolic lesions after the ablating.

25. The method or use of clause 1, wherein the predetermined acute effectiveness is defined by a complication rate of approximately 5-9% or fewer of the plurality of patients experiencing a primary adverse event by approximately 7 or more days after the ablating.

26. The method or use of clause 1, wherein inclusion criteria for the plurality of patients comprises:

a diagnosis with symptomatic paroxysmal atrial fibrillation; and a patient capability to comply with uninterrupted per-protocol anticoagulation requirements.

27. The method or use of clause 1, wherein the predetermined acute effectiveness is defined by a total procedure time.

28. The method or use of clause 1, wherein the predetermined acute effectiveness is defined by a total ablation time.

29. The method or use of clause 1, wherein the predetermined acute effectiveness is defined by a total RF application time.

30. The method or use of clause 1, wherein the predetermined acute effectiveness is defined by a total dwell time of the multi-electrode radiofrequency balloon catheter.

31. The method or use of clause 1, wherein the predetermined acute effectiveness is defined by a total time to isolate all targeted pulmonary veins.

32. The method or use of clause 1, wherein the predetermined acute effectiveness is defined by a number and a total time of applications by the multi-electrode radiofrequency balloon catheter per location of all targeted pulmonary veins.

33. The method or use of clause 1, wherein the predetermined acute effectiveness is defined by a number and a total time of applications by the multi-electrode radiofrequency balloon catheter per patient.

34. The method or use of clause 1, wherein the predetermined acute effectiveness is defined by a number and a total time of applications by the multi-electrode radiofrequency balloon catheter per targeted vein.

35. The method or use of any previous clause, wherein the multi-electrode radiofrequency balloon catheter comprises:
a compliant balloon with a plurality of electrodes bonded configured to deliver RF energy to tissue of the pulmonary vein and sense temperature at each electrode.

36. The method or use of clause 1, wherein clinical effectiveness is defined by an incidence of early onset of one or more adverse events within a predetermined time of the method or use being implemented.

37. The method or use of clause 36, wherein the predetermined time is at least 7 days.

38. The method or use of clause 36, wherein the one or more adverse events comprise: death, atrio-esophageal fistula, myocardial infarction, cardiac tamponade/perforation, thromboembolism, stroke, TIA (Transient Ischemic Attack), phrenic nerve paralysis, pulmonary vein stenosis, and the major vascular access bleeding.

39. The method or use of clause 36, wherein the one or more adverse events comprise: incidence of individual adverse events from a primary composite; incidence of serious adverse device effect; incidence of serious adverse events within 7 days, at least 7-30 days, and at least 30 days following the ablating; incidence of non-serious adverse events; incidence of pre- and post-ablation asymptomatic and symptomatic cerebral emboli as determined by MRI evaluation; and frequency, anatomic location, and size (diameter and volume) of cerebral emboli by MRI evaluations at baseline, post-ablation and during follow-up.

40. The method or use of clause 36, wherein the one or more adverse events for approximately 5-9% of the plurality of patients, the one or more adverse events comprising:
NIHSS (National Institute of Health Stroke Scale) scores at baseline, post-ablation and during follow-up;
a summary of MoCA (Montreal Cognitive Assessment) and mRS (Modified Ranking Scale) scores at baseline, 1 month and during further follow-up; a rate of hospitalization for cardiovascular events; a percentage (%) of pulmonary vein isolation touch-up by focal catheter among the one or more targeted veins;
a percentage (%) of subjects with use of focal catheter ablations for non-PV triggers;
a percentage (%) of subjects with freedom from documented symptomatic atrial fibrillation (AF), atrial tachycardia (AT), or atypical (left side) atrial flutter (AFL) episodes (episodes >30 seconds on arrhythmia monitoring device from day 91 to 180);
a percentage (%) of subjects with freedom from documented atrial fibrillation (AF), atrial tachycardia (AT), or atypical (left side) atrial flutter (AFL);
one or more episodes that endure for 30 or more seconds on an arrhythmia monitoring device from day 91 to 180 following the ablating; and
one or more procedural parameters including total procedure and ablation time, balloon dwell time, RF application time, a number of RF applications, fluoroscopy time and dose.

41. The method or use of clause 1, wherein the acute safety rate includes complication rates of 10% or less and is defined by incidence of asymptomatic cerebral embolic lesions at a discharge magnetic resonance imaging (MRI).

42. The method or use of clause 1, wherein the acute effectiveness rate is 100% and is defined by electrically isolating all targeted pulmonary veins without use of a focal ablation catheter.

43. The method or use of clause 1, wherein the acute effectiveness rate is defined by a freedom from documented atrial fibrillation, atrial tachycardia, or atypical atrial flutter episodes based on electrocardiographic data through an effectiveness evaluation period (1 year).

44. The method or use of clause 1, wherein the acute effectiveness rate is defined by pulmonary vein isolation touch-up by a focal catheter among all targeted pulmonary veins.

45. The method or use of clause 1, wherein the predetermined clinical effectiveness rate is defined by 10% or less complication rates related to incidence of post-ablation symptomatic and asymptomatic cerebral emboli as compared to pre-ablation.

46. The method or use of clause 1, wherein the multi-electrode diagnostic catheter is configured for electrophysiological recording and stimulation of the atrial region of the heart and is used in conjunction with the multi-electrode radiofrequency balloon catheter.

47. A method or use to treat a plurality of patients for paroxysmal atrial fibrillation, the method or use comprising the steps of:
delivering a multi-electrode radiofrequency balloon catheter having a plurality of independently controllable electrodes for radiofrequency ablation and a multi-electrode diagnostic catheter to one or more targeted pulmonary veins; and
ablating tissue of one or more targeted pulmonary veins with one or more of the plurality of the electrodes independently controlled multi-electrode radiofrequency balloon catheter;
diagnosing all targeted pulmonary veins using the multi-electrode diagnostic catheter; and
achieving a predetermined rate of adverse events based on use of the multi-electrode radiofrequency balloon catheter and the multi-electrode diagnostic catheter in the isolation of all targeted pulmonary veins, during and approximately 6 months after the use.

48. A method or use to treat a plurality of patients for paroxysmal atrial fibrillation, the method or use comprising the steps of:
evaluating a number and size of all targeted pulmonary veins and anatomy of the left atrial;
puncturing the transseptal;
selectively positioning a multi-electrode esophageal temperature monitoring device in the vasculature with respect to all targeted pulmonary veins;
selectively positioning a multi-electrode radiofrequency balloon catheter in the vasculature with respect to all targeted pulmonary veins, the multi-electrode radiofrequency balloon catheter having a plurality of independently controllable electrodes for radiofrequency ablation;
selectively positioning a multi-electrode diagnostic catheter in the vasculature with respect to all targeted pulmonary veins;
ablating tissue of all targeted pulmonary veins with one or more of the plurality of the electrodes independently controlled multi-electrode radiofrequency balloon catheter;
confirming isolation of all targeted pulmonary veins using the multi-electrode diagnostic catheter;

confirming existence of an entrance block in all targeted pulmonary veins; and achieving a predetermined clinical effectiveness and/or acute effectiveness of the method or use, based on the confirmed existence of the entrance block, regarding the isolation of all targeted pulmonary veins following the method or use.

49. The method or use according to any of the preceding clauses, further comprising: mapping all targeted pulmonary veins using the diagnostic catheter.

50. The method or use according to any of the preceding clauses, wherein exclusion criteria for the plurality of patients comprises at least one of the following:
   atrial fibrillation secondary to electrolyte imbalance, thyroid disease, or reversible or non-cardiac cause;
   previous surgical or catheter ablation for atrial fibrillation;
   anticipated to receive ablation outside all targeted pulmonary veins ostia and CTI region;
   previously diagnosed with persistent, longstanding atrial fibrillation and/or continuous atrial fibrillation >7 days, or >48 hrs terminated by cardioversion;
   any percutaneous coronary intervention (PCI) within the past 2 months;
   valve repair or replacement and presence of a prosthetic valve;
   any carotid stenting or endarterectomy;
   coronary artery bypass grafting, cardiac surgery, valvular cardiac surgical or percutaneous procedure within the past 6 months;
   documented left atrium thrombus on baseline imaging;
   LA antero posterior diameter greater than 50 mm;
   any pulmonary vein with a diameter greater than or equal to 26 mm;
   left ventricular ejection fraction less than 40%;
   contraindication to anticoagulation;
   history of blood clotting or bleeding abnormalities;
   myocardial infarction within the past 2 months;
   documented thromboembolic event within the past 12 months;
   rheumatic heart disease;
   awaiting cardiac transplantation or other cardiac surgery within the next 12 months;
   unstable angina;
   acute illness or active systemic infection or sepsis;
   diagnosed atrial myxoma or interatrial baffle or patch;
   presence of implanted pacemaker, implantable cardioverter defibrillator, tissue-embedded, or iron-containing metal fragments;
   significant pulmonary disease or any other disease or malfunction of the lungs or respiratory system that produces chronic symptoms;
   significant congenital anomaly;
   pregnancy or lactating;
   enrollment in an investigational study evaluating another device, biologic, or drug;
   pulmonary vein stenosis;
   presence of intramural thrombus, tumor or other abnormality that precludes vascular access, or manipulation of the catheter;
   presence of an IVC filter;
   presence of a condition that precludes vascular access;
   life expectancy or other disease processes likely to limit survival to less than 12 months;
   contraindication to use of contrast agents for MiI;
   presence of iron-containing metal fragments in the patient; or
   unresolved pre-existing neurological deficit.

51. The method or use of any previous clause, wherein the multi-electrode radiofrequency balloon catheter comprises:
   a compliant balloon with a plurality of electrodes configured to deliver RF energy to tissue of all targeted pulmonary veins and sense temperature at each electrode.

52. The method or use of clause 51, wherein the plurality of electrodes is oriented circularly to circumferentially contact with an ostia of the pulmonary vein.

53. The method or use of clause 51, further comprising using the plurality of electrodes for visualization, stimulation, recording, and ablation.

54. The method or use of clause 51, wherein each electrode is configured so an amount of power delivered to each electrode is controlled independently.

55. The method or use of clause 51, wherein the multi-electrode radiofrequency balloon catheter further comprises a proximal handle, a distal tip, and a middle section disposed therebetween.

56. The method or use of clause 55, wherein the proximal handle is a deflection thumb knob allowing for unidirectional deflection, a balloon advancement mechanism, and a luer fitting for balloon inflation and irrigation.

57. The method or use of clause 51, wherein the multi-electrode radiofrequency balloon catheter further comprises
   a high-torque shaft configured to be rotated to facilitate accurate positioning of the catheter tip to a desired; and
   a unidirectional braided deflectable tip section.

58. The method or use of any preceding clause, further comprising:
   controlling irrigation to the multi-electrode radiofrequency balloon catheter with an irrigation pump.

59. The method or use of any preceding clause, further comprising:
   administering uninterrupted anticoagulation therapy at least 1 month prior to the procedure.

60. The method or use of any preceding clause, wherein if the patient is receiving warfarin/coumadin therapy, the patient must have an international normalized ratio (INR)≥2 for at least 3 weeks prior to the procedure.

61. The method or use of any preceding clause, wherein if the patient is receiving warfarin/coumadin therapy, the patient must be confirmed to have an international normalized ratio (INR)≥2 within 48 hours pre-procedure.

62. The method or use of any preceding clause, further comprising: continuing anticoagulation therapy prior to the procedure.

63. The method or use of any preceding clause, further comprising:
   administering a transseptal puncture;
   confirming an activated clotting time target of ≥350 sec. prior to inserting the multi-electrode radiofrequency balloon catheter into the left atrium and maintaining throughout the procedure;
   introducing the multi-electrode radiofrequency balloon catheter;
   introducing of a multi-electrode circular diagnostic catheter;
   ablating the pulmonary vein with the multi-electrode radiofrequency balloon catheter;
   determining in real time pulmonary vein isolation with the multi-electrode circular diagnostic catheter; and
   confirming whether an entrance is blocked in the pulmonary vein.

64. The method or use of any preceding clause, wherein the multi-electrode circular diagnostic catheter comprises:
   an elongated body having a longitudinal axis;

a distal assembly distal the elongated body, the distal assembly having a helical form comprising a proximal loop and a distal loop, and a shape-memory support member extending through at least the proximal loop, the proximal loop and the distal loop being oriented obliquely at an angle relative to the longitudinal axis of the elongated body;

at least one irrigated ablation ring electrode mounted on the proximal loop;

a control handle proximal the elongated body; and a contraction wire having a proximal end in the control handle and a distal end anchored in the proximal loop, the control handle including a first control member configured to actuate the contraction wire to contract the proximal loop, wherein the proximal loop has a first flexibility and the distal loop has a second flexibility, and the second flexibility is greater than the first flexibility.

65. A method or use of treating a plurality of patients for paroxysmal atrial fibrillation by applying energy to tissue of a subject's heart proximate to an esophagus, phrenic nerve, or lung, the method or use comprising the steps of:

achieving at least one of a predetermined clinical effectiveness and acute effectiveness of the procedure based on use of a multi-electrode radiofrequency balloon catheter and a multi-electrode diagnostic catheter in the isolation of the one or more targeted pulmonary veins by:

positioning an expandable member proximate to the left atrium, the expandable member of the multi-electrode radiofrequency balloon catheter having a longitudinal axis and including a plurality of electrodes disposed about the longitudinal axis, each electrode capable of being energized independently, the plurality of electrodes including a first electrode having a first radiopaque marker and a second electrode having a second radiopaque marker different from the first radiopaque marker;

viewing an image of the expandable member as well as the first and second radiopaque markers in the left atrium;

determining an orientation of the first and second radiopaque markers with respect to a portion of the left atrium closest to the esophagus, phrenic nerve, or lung, of the subject;

moving one of the first and second radiopaque markers to a portion of the left atrium closest to the esophagus, phrenic nerve or lung;

energizing one or more electrodes indexed to the one of the radiopaque markers proximate the portion close to the esophagus, phrenic nerve, or lung, at a lower energization setting as compared to other electrodes to create a transmural lesion in the left atrium with little or no effect to adjacent anatomical structures; and electrophysiologically recording and stimulating the atrial region of the tissue proximate to the esophagus, phrenic nerve, or lung using the multi-electrode diagnostic catheter.

66. A clinically effective device to treat atrial fibrillation in a group of patients, the device comprising an end probe coupled to a tubular member that extends along a longitudinal axis from a proximal portion to a distal portion, the end probe comprising:

a first expandable membrane coupled to the tubular member;

a plurality of electrodes disposed generally equiangularly about the longitudinal axis on an outer surface of the first expandable membrane;

at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane; and wherein the device is configured to achieve a predetermined effectiveness rate of pulmonary vein isolation in the group of patients.

67. A clinically effective device to administer a procedure for cardiac electrophysiological ablation of pulmonary veins of the atria and treatment of drug refractory recurrent symptomatic pulmonary atrial fibrillation, the device comprising:

an end probe coupled to a tubular member that extends along a longitudinal axis from a proximal portion to a distal portion, the end probe comprising:

a first expandable membrane coupled to the tubular member;

a plurality of electrodes disposed generally equiangularly about the longitudinal axis on an outer surface of the first expandable membrane;

at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane so that each of the plurality of electrodes is independently controlled to achieve a predetermined effectiveness rate of pulmonary vein isolation.

68. A clinically effective device to administer a procedure for cardiac electrophysiological ablation of pulmonary veins of the atria and treatment of drug refractory recurrent symptomatic pulmonary atrial fibrillation, the device comprising:

an end probe coupled to a tubular member that extends along a longitudinal axis from a proximal portion to a distal portion, the end probe comprising:

a first expandable membrane coupled to the tubular member;

a plurality of electrodes disposed generally equiangularly about the longitudinal axis on an outer surface of the first expandable membrane;

at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane so that each of the plurality of electrodes is independently controlled to achieve pulmonary vein isolation and at least a 97% safety endpoint within seven (7) days of successful pulmonary vein isolation.

69. A clinically effective device to administer a procedure for cardiac electrophysiological ablation of pulmonary veins of the atria and treatment of drug refractory recurrent symptomatic pulmonary atrial fibrillation, the device comprising:

an end probe coupled to a tubular member that extends along a longitudinal axis from a proximal portion to a distal portion, the end probe comprising:

a first expandable membrane coupled to the tubular member;

a plurality of electrodes disposed generally equiangularly about the longitudinal axis on an outer surface of the first expandable membrane;

at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane so that each of the plurality of electrodes is independently controlled to achieve pulmonary vein isolation and at least a 90% safety endpoint within seven (7) days of successful pulmonary vein isolation.

70. The device of one of the preceding clauses, wherein the predetermined effectiveness rate includes complication rates of 10% or less and is defined by existence or non-existence of asymptomatic cerebral embolic lesions at a discharge magnetic resonance imaging (MRI).

71. The device of one of the preceding clauses, wherein the predetermined effectiveness rate includes complication rates of approximately 0% and is defined by existence or non-existence of esophageal injury erythema.

72. The device of one of the preceding clauses, wherein the predetermined effectiveness rate is approximately 100% and is defined by electrically isolating all targeted pulmonary veins without use of a focal ablation catheter.

73. The device of one of the preceding clauses, wherein the predetermined effectiveness rate is defined by a freedom from documented atrial fibrillation, atrial tachycardia, or atypical atrial flutter episodes based on electrocardiographic data through an effectiveness evaluation period.

74. The device of Clause 73, wherein the effectiveness evaluation period is approximately one year.

75. The device of one of the preceding clauses, wherein the predetermined effectiveness rate is defined by pulmonary vein isolation touch-up by a focal catheter among all targeted pulmonary veins.

76. The device of one of the preceding clauses, wherein the predetermined effectiveness rate is defined by using focal catheter ablation for non-PV triggers during the index procedure.

77. The device of one of the preceding clauses, wherein the predetermined effectiveness rate comprises a long-term effectiveness rate.

78. The device of one of the preceding clauses, wherein the predetermined effectiveness rate is defined by an average number of Radio-Frequency applications per patient and Radio-Frequency time required to isolate all pulmonary veins.

79. The device of one of the preceding clauses, wherein the predetermined effectiveness rate is defined by an average number of Radio-Frequency applications per vein and Radio-Frequency time required to isolate common pulmonary veins.

80. The device of one of the preceding clauses, wherein the predetermined effectiveness rate is defined by an average number of Radio-Frequency applications per patient and Radio-Frequency time required to isolate common pulmonary veins.

81. The device of one of the preceding clauses, wherein the predetermined effectiveness rate is defined by determining incidence of complication rates being 10% or less of post-ablation symptomatic and asymptomatic cerebral emboli as compared to pre-ablation.

82. The device of one of the preceding clauses, wherein the predetermined effectiveness rate is defined by evaluating a presence of emboli-associated neurological deficits by at least one of NIHSS and mRS assessments.

83. The device of any previous clause, wherein the end probe is configured for use in catheter-based cardiac electrophysiological mapping of the atria.

84. The device of any previous clause, wherein the end probe is configured for cardiac ablation.

85. The device of any previous clause, wherein the end probe comprises: the plurality of electrodes bonded to the first expandable membrane and configured to deliver Radio-Frequency energy to tissue of the pulmonary vein and sense temperature at each electrode.

86. The device of any previous clause, wherein the plurality of electrodes is oriented circularly to circumferentially contact with an ostia of the pulmonary vein.

87. The device of any previous clause, wherein the device is further configured for using the plurality of electrodes for visualization, stimulation, recording, and ablation.

88. The device of any previous clause, wherein each electrode is configured so an amount of power delivered to each electrode is controlled independently.

89. The device of any previous clause, wherein the end probe further comprises a proximal handle, a distal tip, and a middle section disposed therebetween.

90. The device of any previous clause, wherein the proximal handle is a deflection thumb knob allowing for unidirectional deflection, a balloon advancement mechanism, and a luer fitting for balloon inflation and irrigation.

91. The device of any previous clause, wherein the end probe further comprises a high-torque shaft configured to be rotated to facilitate accurate positioning of the catheter tip to a desired; and a unidirectional braided deflectable tip section.

92. The device of any previous clause, wherein the end probe further comprises:

a first substrate disposed on the membrane, the first substrate including a first radiopaque marker of a first form disposed thereon; and a second substrate disposed on the membrane, the second substrate including a second radiopaque marker of a second form disposed thereon, the second form being different from the first form.

93. The device of any previous clause, further comprising an irrigation pump to provide irrigation fluid to the first expandable membrane and out of the first expandable membrane.

94. The device of any preceding clause, wherein the effectiveness evaluation period is at least 91 days following a delivery of the end probe to the pulmonary vein; and ablation of tissue proximate the pulmonary vein with the end probe.

95. The device of any preceding clause, wherein the effectiveness evaluation period is less than or equal to one year following a delivery of the end probe to the pulmonary vein; and ablation of tissue proximate the pulmonary vein with the end probe.

96. The device of any previous clause, wherein the predetermined success rate is 60% for a population size of at least 40 patients.

97. The device of any previous clause, wherein a population size for the predetermined success rate is at least 300 patients.

98. The device of any previous clause, wherein a population size for the predetermined success rate is at least 200 patients.

99. The device of any previous clause, wherein a population size for the predetermined success rate is at least 100 patients.

100. The device of any previous clause, wherein a population size for the predetermined success rate is at least 50 patients.

101. The device of any previous clause, wherein the predetermined success rate is at least 60%.

102. The device of any previous clause, wherein the predetermined success rate is determined by evaluation of the patient 7 days following a delivery of the end probe to the pulmonary vein and ablation of tissue proximate the pulmonary vein with the end probe.

103. The device of any previous clause, wherein the predetermined success rate is determined by evaluation of the patient 1 month following a delivery of the end probe to the pulmonary vein; and ablation of tissue proximate the pulmonary vein with the end probe.

104. The device of any previous clause, wherein the predetermined success rate is determined by evaluation of the patient 6 months following a delivery of the end probe to the pulmonary vein; and ablation of tissue proximate the pulmonary vein with the end probe.

105. The device of any previous clause, wherein the predetermined success rate is determined by evaluation of the patient 12 months following a delivery of the end probe to the pulmonary vein; and ablation of tissue proximate the pulmonary vein with the end probe.

106. The device of any previous clause, wherein the predetermined success rate further comprises: confirmation of an entrance block in the pulmonary vein after at least one of adenosine and isoproterenol challenge.

107. The device of any previous clause, wherein the patient suffering at least one of the following events is deemed as unsuccessful pulmonary vein isolation, including:
  device or procedure related death;
  atrio-esophageal fistula, myocardial infarction;
  cardiac Tamponade/Perforation;
  thromboembolism;
  stroke/Cerebrovascular Accident (CVA);
  transient Ischemic Attach (TIA);
  phrenic Nerve Paralysis, Pulmonary Vein Stenosis;
  pericarditis;
  pulmonary Edema;
  major Vascular Access Complication/Bleeding; and
  hospitalization (initial or prolonged).

108. The device of any previous clause, wherein the patient suffering at least one of the following events is deemed as unsuccessful pulmonary vein isolation, comprising:
  acute procedural failure;
  repeat ablation or surgical treatment for AF/AT/Atypical (left-side) AFL after the blanking period (after day 90 post index procedure);
  DC cardioversion for AF/AT/Atypical (left-side) AFL, continuous AF/AT/AFL on a standard 12-lead ECG even if the recording is less than 30 seconds in duration (after day 90 post index procedure);
  a new Class I and/or Class III AAD is prescribed for AF during effectiveness evaluation period (day 91-365 post index procedure) or prescribed during the blanking period and continued past 90 days;
  a previously failed Class I and/or Class III AAD (failed at or before screening) is taken for AF at a greater dose than the highest ineffective historical dose during the effectiveness evaluation period; and
  amiodarone is prescribed post procedure.

109. The device any previous clause, wherein the safety endpoint is defined by a patient suffering a primary adverse event.

110. The device of any previous clause, wherein at least one risk factor for the patient is selected from the group consisting of:
  at least three (3) symptomatic episodes of atrial fibrillation that last lasting ≥1 minute within six (6) months before the device;
  at least one (1) atrial fibrillation episode electrocardiographically documented within twelve (12) months prior to enrollment, whereby electrocardiographic documentation can include, but is not limited to, electrocardiogram (ECG), Holter monitor, or telemetry strip;
  failing at least one (1) Class I or Class III AAD as evidenced by recurrent symptomatic atrial fibrillation or intolerable side effects to the AAD;
  age 18-75 years;
  secondary to electrolyte imbalance;
  thyroid disease;
  reversible or non-cardiac cause; and
  previous surgical or catheter ablation for atrial fibrillation.

111. The device of any previous clause, wherein the patient has at least one risk factor selected from the group consisting of:
  Patients known to require ablation outside the PV ostia and CTI region;
  Previously diagnosed with persistent or long-standing persistent atrial fibrillation and/or Continuous atrial fibrillation 7 days following the device procedure;
  any percutaneous coronary intervention within the past 2 months;
  repair or replacement or presence of a prosthetic valve;
  any carotid stenting or endarterectomy within the past 6 months;
  Coronary artery bypass grafting, cardiac surgery or valvular cardiac surgical procedure within the past 6 months;
  Documented left atrium thrombus within 1 day prior to the device procedure;
  left atrium antero posterior diameter >50 mm;
  Left Ventricular Ejection Fraction <40%;
  Contraindication to anticoagulation;
  History of blood clotting or bleeding abnormalities;
  Myocardial infarction within the past 2 months;
  Documented thromboembolic event (including transient ischemic attack) within the past 12 months;
  Rheumatic Heart Disease;
  Uncontrolled heart failure or New York Heart Association (NYHA) function class III or IV;
  Awaiting cardiac transplantation or other cardiac surgery within the next 12 months;
  Unstable angina;
  Acute illness or active systemic infection or sepsis;
  Diagnosed atrial myxoma or presence of an interatrial baffle or patch;
  Presence of implanted pacemaker or implantable cardioverter defibrillator (ICD);
  Significant pulmonary disease or any other disease or malfunction of the lungs or respiratory system that produces chronic symptoms;
  Significant congenital anomaly;
  women who are pregnant;
  enrollment in an investigational study evaluating another device, biologic, or drug;
  known pulmonary vein stenosis;

presence of intramural thrombus, tumor or other abnormality that precludes vascular access, or manipulation of the catheter;

presence of an inferior vena cava filter;

presence of a condition that precludes vascular access;

life expectancy or other disease processes likely to limit survival to less than 12 months;

presenting contra-indication for the devices; and patient on amiodarone at any time during the past 3 months prior to enrollment.

112. The device of any previous clause, wherein if the patient is receiving warfarin/coumadin therapy, the patient must have an international normalized ratio ≥2 for at least 3 weeks prior to the procedure.

113. The device of any previous clause, wherein if the patient is receiving warfarin/coumadin therapy, the patient must be confirmed to be ≥2 within 48 hours pre-procedure.

114. The device of any previous clause, wherein anticoagulation therapy is provided prior to the procedure.

115. The device of any previous clause, wherein an activated clotting time of 350-400 seconds is targeted prior to insertion of the catheter and throughout the procedure.

116. The device of any previous clause, wherein an activated clotting time levels are checked every 15-30 minutes during the procedure to ensure an activated clotting time target of 350-400 seconds.

117. The device of any previous clause, wherein the multi-electrode circular diagnostic catheter comprises:

an elongated body having a longitudinal axis;

a distal assembly distal the elongated body, the distal assembly having a helical form comprising a proximal loop and a distal loop, and a shape-memory support member extending through at least the proximal loop, the proximal loop and the distal loop being oriented obliquely at an angle relative to the longitudinal axis of the elongated body;

at least one irrigated ablation ring electrode mounted on the proximal loop;

a control handle proximal the elongated body; and a contraction wire having a proximal end in the control handle and a distal end anchored in the proximal loop, the control handle including a first control member configured to actuate the contraction wire to contract the proximal loop, wherein the proximal loop has a first flexibility and the distal loop has a second flexibility, and the second flexibility is greater than the first flexibility.

118. A method or use of administering a procedure for treating atrial fibrillation, comprising:

delivering a multi-electrode radiofrequency balloon catheter to one or more targeted pulmonary veins;

ablating tissue of the pulmonary vein using the multi-electrode radiofrequency balloon catheter; and achieving a predetermined effectiveness rate of pulmonary vein isolation.

119. The method or use of clause 118, wherein the predetermined effectiveness rate includes complication rates of 10% or less and is defined by existence of asymptomatic cerebral embolic lesions at a discharge magnetic resonance imaging (MRI).

120. The method or use of clause 118, wherein the predetermined effectiveness rate is defined by a freedom from documented atrial fibrillation, atrial tachycardia, or atypical atrial flutter episodes based on electrocardiographic data through an effectiveness evaluation period.

121. The method or use of clause 120, wherein the effectiveness evaluation period is approximately one year.

122. The method or use of clause 118, wherein the predetermined effectiveness rate is defined by pulmonary vein isolation touch-up by a focal catheter among all targeted pulmonary veins.

123. The method or use of clause 118, wherein the predetermined effectiveness rate is defined by using focal catheter ablation for non-PV triggers during the index procedure.

124. The method or use of clause 118, wherein the predetermined effectiveness rate comprises a long-term effectiveness rate.

125. The method or use of clause 118, wherein the predetermined effectiveness rate is defined by an average number of RF applications per patient and RF time required to isolate all pulmonary veins.

126. The method or use of clause 118, wherein the predetermined effectiveness rate is defined by an average number of RF applications per vein and RF time required to isolate common pulmonary veins.

127. The method or use of clause 118, wherein the predetermined effectiveness rate is defined by an average number of RF applications per patient and RF time required to isolate common pulmonary veins.

128. The method or use of clause 118, wherein the predetermined effectiveness rate is defined by determining incidence of complication rates being 10% or less of post-ablation symptomatic and asymptomatic cerebral emboli as compared to pre-ablation.

129. The method or use of clause 118, wherein the predetermined effectiveness rate is defined by evaluating a presence of emboli-associated neurological deficits by at least one of NIHSS and mRS assessments.

130. The method or use of any previous clause, wherein the multi-electrode radiofrequency balloon catheter is configured for use in catheter-based cardiac electrophysiological mapping of the atria.

131. The method or use of any previous clause, wherein the multi-electrode radiofrequency balloon catheter is configured for cardiac ablation.

132. The method or use of any previous clause, wherein the multi-electrode radiofrequency balloon catheter comprises:

a compliant balloon with a plurality of electrodes bonded configured to deliver RF energy to tissue of the pulmonary vein and sense temperature at each electrode.

133. The method or use of clause 132, wherein the plurality of electrodes is oriented circularly to circumferentially contact with an ostia of the pulmonary vein.

134. The method or use of clause 132, further comprising: using the plurality of electrodes for visualization, stimulation, recording, and ablation.

135. The method or use of clause 132, wherein each electrode is configured so an amount of power delivered to each electrode is controlled independently.

136. The method or use of clause 132, wherein the multi-electrode radiofrequency balloon catheter further comprises a proximal handle, a distal tip, and a middle section disposed therebetween.

137. The method or use of clause 136, wherein the proximal handle is a deflection thumb knob allowing for unidirectional deflection, a balloon advancement mechanism, and a luer fitting for balloon inflation and irrigation.

138. The method or use of clause 132, wherein the multi-electrode radiofrequency balloon catheter further comprises a high-torque shaft configured to be rotated to facilitate accurate positioning of the catheter tip to a desired; and a unidirectional braided deflectable tip section.

139. The method or use of clause 132, wherein the balloon has a membrane, the balloon having a distal end and a proximal end defining a longitudinal axis, the multi-electrode radiofrequency balloon catheter further comprises:

a first substrate disposed on the membrane, the first substrate including a first radiopaque marker of a first form disposed thereon; and a second substrate disposed on the membrane, the second substrate including a second radiopaque marker of a second form disposed thereon, the second form being different from the first form.

140. The method or use of any preceding clause, further comprising:

controlling irrigation to the multi-electrode radiofrequency balloon catheter with an irrigation pump.

141. The method or use of any preceding clause, wherein the effectiveness evaluation period is at least 91 days following:

the delivering the multi-electrode radiofrequency balloon catheter to the pulmonary vein; and the ablating tissue of the pulmonary vein using the multi-electrode radiofrequency balloon catheter.

142. The method or use of any preceding clause, wherein the effectiveness evaluation period is less than or equal to one year following:

the delivering the multi-electrode radiofrequency balloon catheter to the pulmonary vein; and the ablating tissue of the pulmonary vein using the multi-electrode radiofrequency balloon catheter.

143. A method or use of administering a procedure for treating atrial fibrillation, comprising:

delivering a multi-electrode radiofrequency balloon catheter to a pulmonary vein;

ablating tissue of the pulmonary vein using the multi-electrode radiofrequency balloon catheter; and achieving a predetermined success rate of pulmonary vein isolation.

144. The method or use of clause 143, wherein the predetermined success rate is 60% for a population size of at least 40 patients.

145. The method or use of any previous clause, wherein a population size for the predetermined success rate is at least 300 patients.

146. The method or use of any previous clause, wherein a population size for the predetermined success rate is at least 200 patients.

147. The method or use of any previous clause, wherein a population size for the predetermined success rate is at least 100 patients.

148. The method or use of any previous clause, wherein a population size for the predetermined success rate is at least 50 patients.

149. The method or use of any previous clause, wherein the predetermined success rate is at least 60%.

150. The method or use of any previous clause, wherein the predetermined success rate is determined by evaluating the patient 7 days following:

the delivering the multi-electrode radiofrequency balloon catheter to the pulmonary vein; and the ablating tissue of the pulmonary vein using the multi-electrode radiofrequency balloon catheter.

151. The method or use of any previous clause, wherein the predetermined success rate is determined by evaluating the patient 1 month following:

the delivering the multi-electrode radiofrequency balloon catheter to the pulmonary vein; and the ablating tissue of the pulmonary vein using the multi-electrode radiofrequency balloon catheter.

152. The method or use of any previous clause, wherein the predetermined success rate is determined by evaluating the patient 6 months following:

the delivering the multi-electrode radiofrequency balloon catheter to the pulmonary vein; and the ablating tissue of the pulmonary vein using the multi-electrode radiofrequency balloon catheter.

153. The method or use of any previous clause, wherein the predetermined success rate is determined by evaluating the patient 12 months following:

the delivering the multi-electrode radiofrequency balloon catheter to the pulmonary vein; and the ablating tissue of the pulmonary vein using the multi-electrode radiofrequency balloon catheter.

154. The method or use of any previous clause, wherein the predetermined success rate further comprises:

confirming an entrance block in the pulmonary vein after at least one of adenosine and isoproterenol challenge.

155. The method or use of any previous clause, wherein the delivering step further comprises using a focal catheter.

156. The method or use of any preceding clause, wherein the patient suffering at least one of the following events is deemed as unsuccessful pulmonary vein isolation, including:

device or procedure related death;
atrio-esophageal fistula, myocardial infarction;
cardiac Tamponade/Perforation;
thromboembolism;
stroke/Cerebrovascular Accident (CVA);
transient Ischemic Attach (TIA);
phrenic Nerve Paralysis, Pulmonary Vein Stenosis;
pericarditis;
pulmonary Edema;
major Vascular Access Complication/Bleeding; and
hospitalization (initial or prolonged).

157. The method or use of any preceding clause, wherein the patient suffering at least one of the following events is deemed as unsuccessful pulmonary vein isolation, comprising:

acute procedural failure;
repeat ablation or surgical treatment for AF/AT/Atypical (left-side) AFL after the blanking period (after day 90 post index procedure);
DC cardioversion for AF/AT/Atypical (left-side) AFL, continuous AF/AT/AFL on a standard 12-lead ECG even if the recording is less than 30 seconds in duration (after day 90 post index procedure);
a new Class I and/or Class III AAD is prescribed for AF during effectiveness evaluation period (day 91-365 post index procedure) or prescribed during the blanking period and continued past 90 days;
a previously failed Class I and/or Class III AAD (failed at or before screening) is taken for AF at a greater dose than the highest ineffective historical dose during the effectiveness evaluation period; and
amiodarone is prescribed post procedure.

158. A method or use for administering a procedure for cardiac electrophysiological ablation of pulmonary veins of the atria and treating drug refractory recurrent symptomatic pulmonary atrial fibrillation, comprising:

delivering a multi-electrode radiofrequency balloon catheter to a pulmonary vein;

ablating tissue of the pulmonary vein using the multi-electrode radiofrequency balloon catheter; and achieving a predetermined effectiveness rate of pulmonary vein isolation.

159. A method or use for administering a procedure for cardiac electrophysiological ablation of pulmonary veins of the atria and treating drug refractory recurrent symptomatic pulmonary atrial fibrillation, comprising:

delivering a multi-electrode radiofrequency balloon catheter to a pulmonary vein;

ablating tissue of the pulmonary vein using the multi-electrode radiofrequency balloon catheter; and achieving pulmonary vein isolation and at least a 97% safety endpoint within seven (7) days of successful pulmonary vein isolation.

160. A method or use for administering a procedure for cardiac electrophysiological ablation of pulmonary veins of the atria and treating drug refractory recurrent symptomatic pulmonary atrial fibrillation, comprising:

delivering a multi-electrode radiofrequency balloon catheter to a pulmonary vein;

ablating tissue of the pulmonary vein using the multi-electrode radiofrequency balloon catheter; and achieving pulmonary vein isolation and at least a 90% safety endpoint within seven (7) days of successful pulmonary vein isolation.

161. The method or use of any preceding clause, wherein the safety endpoint is defined by a patient suffering a primary adverse event.

162. The method or use of any preceding clause, wherein at least one risk factor for the patient is selected from the group consisting of:

at least three (3) symptomatic episodes of atrial fibrillation that last lasting ≥1 minute within six (6) months before the method or use;

at least one (1) atrial fibrillation episode electrocardiographically documented within twelve (12) months prior to enrollment. Electrocardiographic documentation can include, but is not limited to, electrocardiogram (ECG), Holter monitor, or telemetry strip;

failing at least one (1) Class I or Class III AAD as evidenced by recurrent symptomatic atrial fibrillation or intolerable side effects to the AAD;

age 18-75 years;

secondary to electrolyte imbalance;

thyroid disease;

reversible or non-cardiac cause; and previous surgical or catheter ablation for atrial fibrillation.

163. The method or use of any preceding clause, wherein the patient has at least one risk factor selected from the group consisting of:

Patients known to require ablation outside the PV ostia and CTI region;

Previously diagnosed with persistent or long-standing persistent atrial fibrillation and/or Continuous atrial fibrillation 7 days following the method or use procedure;

any percutaneous coronary intervention within the past 2 months;

repair or replacement or presence of a prosthetic valve;

any carotid stenting or endarterectomy within the past 6 months;

Coronary artery bypass grafting, cardiac surgery or valvular cardiac surgical procedure within the past 6 months;

Documented left atrium thrombus within 1 day prior to the method or use procedure;

left atrium antero posterior diameter >50 mm;

Left Ventricular Ejection Fraction <40%;

Contraindication to anticoagulation;

History of blood clotting or bleeding abnormalities;

Myocardial infarction within the past 2 months;

Documented thromboembolic event (including transient ischemic attack) within the past 12 months;

Rheumatic Heart Disease;

Uncontrolled heart failure or New York Heart Association (NYHA) function class III or IV;

Awaiting cardiac transplantation or other cardiac surgery within the next 12 months;

Unstable angina;

Acute illness or active systemic infection or sepsis;

Diagnosed atrial myxoma or presence of an interatrial baffle or patch;

Presence of implanted pacemaker or implantable cardioverter defibrillator (ICD);

Significant pulmonary disease or any other disease or malfunction of the lungs or respiratory system that produces chronic symptoms;

Significant congenital anomaly;

women who are pregnant;

enrollment in an investigational study evaluating another device, biologic, or drug;

known pulmonary vein stenosis;

presence of intramural thrombus, tumor or other abnormality that precludes vascular access, or manipulation of the catheter;

presence of an inferior vena cava filter;

presence of a condition that precludes vascular access;

life expectancy or other disease processes likely to limit survival to less than 12 months;

presenting contra-indication for the devices; and patient on amiodarone at any time during the past 3 months prior to enrollment.

164. The method or use of any preceding clause, further comprising:

administering uninterrupted anticoagulation therapy at least 1 month prior to the procedure.

165. The method or use of any preceding clause, wherein if the patient is receiving warfarin/coumadin therapy, the patient must have an international normalized ratio ≥2 for at least 3 weeks prior to the procedure.

166. The method or use of any preceding clause, wherein if the patient is receiving warfarin/coumadin therapy, the patient must be confirmed to be ≥2 within 48 hours pre-procedure.

167. The method or use of any preceding clause, further comprising: continuing anticoagulation therapy prior to the procedure.

168. The method or use of any preceding clause, further comprising: targeting an activated clotting time of 350-400 seconds prior to inserting the catheter and throughout the procedure.

169. The method or use of any preceding clause, further comprising: checking an activated clotting time levels every 15-30 minutes during the procedure to ensure an activated clotting time target of 350-400 seconds.

170. The method or use of any preceding clause, further comprising:

administering a transseptal puncture;

confirming an activated clotting time target of ≥350 sec. prior to inserting the multi-electrode radiofrequency balloon catheter into the left atrium and maintaining throughout the procedure;

introducing the multi-electrode radiofrequency balloon catheter;

introducing of a multi-electrode circular diagnostic catheter;

ablating the pulmonary vein with the multi-electrode radiofrequency balloon catheter;

determining in real time pulmonary vein isolation with the multi-electrode circular diagnostic catheter; and confirming whether an entrance is blocked in the pulmonary vein.

171. The method or use of any preceding clause, wherein the multi-electrode circular diagnostic catheter comprises:

an elongated body having a longitudinal axis;

a distal assembly distal the elongated body, the distal assembly having a helical form comprising a proximal loop and a distal loop, and a shape-memory support member extending through at least the proximal loop, the proximal loop and the distal loop being oriented obliquely at an angle relative to the longitudinal axis of the elongated body;

at least one irrigated ablation ring electrode mounted on the proximal loop;

a control handle proximal the elongated body; and a contraction wire having a proximal end in the control handle and a distal end anchored in the proximal loop, the control handle including a first control member configured to actuate the contraction wire to contract the proximal loop, wherein the proximal loop has a first flexibility and the distal loop has a second flexibility, and the second flexibility is greater than the first flexibility.

172. A method or use of pulmonary vein isolation by applying energy to tissue of a subject's heart proximate to an esophagus, phrenic nerve, or lung, the method or use comprising the steps of:

achieving a predetermined effectiveness rate according to any of the previous clauses by:

positioning an expandable member proximate to the left atrium, the expandable member having a longitudinal axis and including a plurality of electrodes disposed about the longitudinal axis, each electrode capable of being energized independently, the plurality of electrodes including a first electrode having a first radiopaque marker and a second electrode having a second radiopaque marker different from the first radiopaque marker;

viewing an image of the expandable member as well as the first and second radiopaque markers in the left atrium;

determining an orientation of the first and second radiopaque markers with respect to a portion of the left atrium closest to the esophagus, phrenic nerve, or lung, of the subject;

moving one of the first and second radiopaque markers to a portion of the left atrium closest to the esophagus, phrenic nerve or lung; and energizing one or more electrodes indexed to the one of the radiopaque markers proximate the portion close to the esophagus, phrenic nerve, or lung, at a lower energization setting as compared to other electrodes to create a transmural lesion in the left atrium with little or no effect to adjacent anatomical structures.

173. Use of an independently controlled multi-electrode radiofrequency balloon catheter to treat paroxysmal atrial fibrillation, comprising:

delivering a multi-electrode radiofrequency balloon catheter having a plurality of independently controllable electrodes for radiofrequency ablation and a multi-electrode diagnostic catheter to one or more targeted pulmonary veins;

ablating tissue of the one or more targeted pulmonary veins with one or more of the plurality of the electrodes independently controlled multi-electrode radiofrequency balloon catheter;

diagnosing the one or more targeted pulmonary veins using the multi-electrode diagnostic catheter; and achieving at least one of a predetermined clinical effectiveness and acute effectiveness of the multi-electrode radiofrequency balloon catheter and the multi-electrode diagnostic catheter in the isolation of the one or more targeted pulmonary veins, during and approximately 3 months after the ablating step.

174. Use according to Clause 173, wherein acute effectiveness is defined by confirming if there is an entrance block in all targeted pulmonary veins after adenosine and/or isoproterenol challenge.

175. Use according to Clause 174, further comprising:

determining the acute effectiveness determined at approximately 3 months after the ablating step; and generating an estimated acute effectiveness at approximately 12 months after the ablating step based on the acute effectiveness determined at approximately 3 months.

176. Use according to Clause 175, wherein the estimated acute effectiveness at approximately 12 months is substantially similar to the acute effectiveness determined at approximately 3 months.

177. Use according to Clause 174, wherein the acute effectiveness is further defined by success greater than 90% for the plurality of patients.

178. Use according to Clause 174, wherein the acute effectiveness is further defined by success greater than 95% for the plurality of patients.

179. Use according to Clause 174, wherein a Type-1 error rate for power the acute effectiveness and the clinical effectiveness of all targeted veins are controlled at approximately a 5% level, use further comprising:

determining whether the ablating is clinically successful for the plurality of patients if both the acute effectiveness and the clinical effectiveness indications are controlled at approximately the 5% level.

180. Use according to Clause 174, wherein the acute effectiveness is at least 80% for the plurality of patients being at least 80 patients.

181. Use according to Clause 174, wherein the acute effectiveness is at least 80% for the plurality of patients being at least 130 patients.

182. Use according to Clause 174, wherein the acute effectiveness is at least 80% for the plurality of patients being at least 180 patients.

183. Use according to Clause 174, wherein the acute effectiveness is at least 80% for the plurality of patients being at least 230 patients.

184. Use according to Clause 174, wherein the acute effectiveness is further defined by confirming if there is an entrance block in all targeted pulmonary veins after adenosine and/or isoproterenol challenge using a focal ablation catheter.

185. Use according to Clause 174, wherein the acute effectiveness is further defined by confirming if there is an entrance block in all targeted pulmonary veins after adenosine and/or isoproterenol challenge without using a focal ablation catheter.

186. Use according to Clause 173, wherein the ablating is administered on the plurality of patients diagnosed with symptomatic paroxysmal atrial fibrillation.

187. Use according to Clause 173, wherein the step of diagnosing further comprises: electrophysiological mapping of the heart.

188. Use according to Clause 173, wherein the multi-electrode diagnostic catheter further comprises a high torque shaft with a halo-shaped tip section containing a plurality of pairs of electrodes visible under fluoroscopy.

189. Use according to Clause 173, wherein the plurality of patients is at least 80.

190. Use according to Clause 173, wherein the plurality of patients is at least 130.

191. Use according to Clause 173, wherein the plurality of patients is at least 180.

192. Use according to Clause 173, wherein the plurality of patients is at least 230.

193. Use according to Clause 173, wherein the predetermined acute effectiveness is defined by ulceration being absent in the plurality of patients after the ablating.

194. Use according to Clause 173, wherein the predetermined acute effectiveness is defined by a complication rate of approximately 13% or fewer of the plurality of patients experiencing esophageal erythema after the ablating.

195. Use according to Clause 173, wherein the predetermined acute effectiveness is defined by a complication rate of approximately 25% or fewer of the plurality of patients experiencing new asymptomatic cerebral embolic lesions after the ablating.

196. Use according to Clause 173, wherein the predetermined acute effectiveness is defined by a complication rate of approximately 20% or fewer of the plurality of patients experiencing new asymptomatic cerebral embolic lesions after the ablating.

197. Use according to Clause 173, wherein the predetermined acute effectiveness is defined by a complication rate of approximately 5-9% or fewer of the plurality of patients experiencing a primary adverse event by approximately 7 or more days after the ablating.

198. Use according to Clause 173, wherein inclusion criteria for the plurality of patients comprises:
a diagnosis with symptomatic paroxysmal atrial fibrillation; and
a patient capability to comply with uninterrupted per-protocol anticoagulation requirements.

199. Use according to Clause 173, wherein the predetermined acute effectiveness is defined by a total procedure time.

200. Use according to Clause 173, wherein the predetermined acute effectiveness is defined by a total ablation time.

201. Use according to Clause 173, wherein the predetermined acute effectiveness is defined by a total RF application time.

202. Use according to Clause 173, wherein the predetermined acute effectiveness is defined by a total dwell time of the multi-electrode radiofrequency balloon catheter.

203. Use according to Clause 173, wherein the predetermined acute effectiveness is defined by a total time to isolate all targeted pulmonary veins.

204. Use according to Clause 173, wherein the predetermined acute effectiveness is defined by a number and a total time of applications by the multi-electrode radiofrequency balloon catheter per location of all targeted pulmonary veins.

205. Use according to Clause 173, wherein the predetermined acute effectiveness is defined by a number and a total time of applications by the multi-electrode radiofrequency balloon catheter per patient.

206. Use according to Clause 173, wherein the predetermined acute effectiveness is defined by a number and a total time of applications by the multi-electrode radiofrequency balloon catheter per targeted vein.

207. Use according to Clause 173, wherein the multi-electrode radiofrequency balloon catheter comprises:
a compliant balloon with a plurality of electrodes bonded configured to deliver RF energy to tissue of the pulmonary vein and sense temperature at each electrode.

208. Use according to Clause 173, wherein clinical effectiveness is defined by an incidence of early onset of one or more adverse events within a predetermined time of the use being implemented.

209. Use according to Clause 208, wherein the predetermined time is at least 7 days.

210. Use according to Clause 208, wherein the one or more adverse events comprise: death, atrio-esophageal fistula, myocardial infarction, cardiac tamponade/perforation, thromboembolism, stroke, TIA (Transient Ischemic Attack), phrenic nerve paralysis, pulmonary vein stenosis, and the major vascular access bleeding.

211. Use according to Clause 208, wherein the one or more adverse events comprise: incidence of individual adverse events from a primary composite; incidence of serious adverse device effect; incidence of serious adverse events within 7 days, at least 7 to 30 days, and at least 30 days following the ablating; incidence of non-serious adverse events; incidence of pre- and post-ablation asymptomatic and symptomatic cerebral emboli as determined by MRI evaluation; and frequency, anatomic location, and size (diameter and volume) of cerebral emboli by MRI evaluations at baseline, post-ablation and during follow-up.

212. Use according to Clause 208, wherein the one or more adverse events for approximately 5-9% of the plurality of patients, the one or more adverse events comprising:
NIHSS (National Institute of Health Stroke Scale) scores at baseline, post-ablation and during follow-up;
a summary of MoCA (Montreal Cognitive Assessment) and mRS (Modified Ranking Scale) scores at baseline, 1 month and during further follow-up; a rate of hospitalization for cardiovascular events; a percentage (%) of pulmonary vein isolation touch-up by focal catheter among the one or more targeted veins;
a percentage (%) of subjects with use of focal catheter ablations for non-PV triggers;
a percentage (%) of subjects with freedom from documented symptomatic atrial fibrillation (AF), atrial tachycardia (AT), or atypical (left side) atrial flutter (AFL) episodes (episodes >30 seconds on arrhythmia monitoring device from day 91 to 180);
a percentage (%) of subjects with freedom from documented atrial fibrillation (AF), atrial tachycardia (AT), or atypical (left side) atrial flutter (AFL);
one or more episodes that endure for 30 or more seconds on an arrhythmia monitoring device from day 91 to 180 following the ablating; and
one or more procedural parameters including total procedure and ablation time, balloon dwell time, RF application time, a number of RF applications, fluoroscopy time and dose.

213. Use according to Clause 173, wherein the acute safety rate includes complication rates of 10% or less and is defined by incidence of asymptomatic cerebral embolic lesions at a discharge magnetic resonance imaging (MRI).

214. Use according to Clause 173, wherein the acute effectiveness rate is 100% and is defined by electrically isolating all targeted pulmonary veins without use of a focal ablation catheter.

215. Use according to Clause 173, wherein the acute effectiveness rate is defined by a freedom from documented atrial fibrillation, atrial tachycardia, or atypical atrial flutter episodes based on electrocardiographic data through an effectiveness evaluation period (1 year).

216. Use according to Clause 173, wherein the acute effectiveness rate is defined by pulmonary vein isolation touch-up by a focal catheter among all targeted pulmonary veins.

217. Use according to Clause 173, wherein the predetermined clinical effectiveness rate is defined by 10% or less complication rates related to incidence of post-ablation symptomatic and asymptomatic cerebral emboli as compared to pre-ablation.

218. Use according to Clause 173, wherein the multi-electrode diagnostic catheter is configured for electrophysiological recording and stimulation of the atrial region of the heart and is used in conjunction with the multi-electrode radiofrequency balloon catheter.

219. Use of an independently controlled multi-electrode radiofrequency balloon catheter to treat a plurality of patients for paroxysmal atrial fibrillation, comprising:
  delivering a multi-electrode radiofrequency balloon catheter having a plurality of independently controllable electrodes for radiofrequency ablation and a multi-electrode diagnostic catheter to one or more targeted pulmonary veins; and
  ablating tissue of one or more targeted pulmonary veins with one or more of the plurality of the electrodes independently controlled multi-electrode radiofrequency balloon catheter;
  diagnosing all targeted pulmonary veins using the multi-electrode diagnostic catheter; and
  achieving a predetermined rate of adverse events based on use of the multi-electrode radiofrequency balloon catheter and the multi-electrode diagnostic catheter in the isolation of all targeted pulmonary veins, during and approximately 6 months after use.

220. Use of an independently controlled multi-electrode radiofrequency balloon catheter to treat a plurality of patients for paroxysmal atrial fibrillation, comprising:
  evaluating a number and size of all targeted pulmonary veins and anatomy of the left atrial;
  puncturing the transseptal;
  selectively positioning a multi-electrode esophageal temperature monitoring device in the vasculature with respect to all targeted pulmonary veins;
  selectively positioning a multi-electrode radiofrequency balloon catheter in the vasculature with respect to all targeted pulmonary veins, the multi-electrode radiofrequency balloon catheter having a plurality of independently controllable electrodes for radiofrequency ablation;
  selectively positioning a multi-electrode diagnostic catheter in the vasculature with respect to all targeted pulmonary veins;
  ablating tissue of all targeted pulmonary veins with one or more of the plurality of the electrodes independently controlled multi-electrode radiofrequency balloon catheter;
  confirming isolation of all targeted pulmonary veins using the multi-electrode diagnostic catheter;
  confirming existence of an entrance block in all targeted pulmonary veins;
  achieving a predetermined clinical effectiveness and/or acute effectiveness of the method or use, based on the confirmed existence of the entrance block, regarding the isolation of all targeted pulmonary veins following the method or use.

221. Use of any previous clause, further comprising: mapping all targeted pulmonary veins using the diagnostic catheter.

222. Use of any previous clause, wherein exclusion criteria for the plurality of patients comprises at least one of the following:
  atrial fibrillation secondary to electrolyte imbalance, thyroid disease, or reversible or non-cardiac cause;
  previous surgical or catheter ablation for atrial fibrillation;
  anticipated to receive ablation outside all targeted pulmonary veins ostia and CTI region;
  previously diagnosed with persistent, longstanding atrial fibrillation and/or continuous atrial fibrillation >7 days, or >48 hrs terminated by cardioversion;
  any percutaneous coronary intervention (PCI) within the past 2 months;
  valve repair or replacement and presence of a prosthetic valve;
  any carotid stenting or endarterectomy;
  coronary artery bypass grafting, cardiac surgery, valvular cardiac surgical or percutaneous procedure within the past 6 months;
  documented left atrium thrombus on baseline imaging;
  LA antero posterior diameter greater than 50 mm;
  any pulmonary vein with a diameter greater than or equal to 26 mm;
  left ventricular ejection fraction less than 40%;
  contraindication to anticoagulation;
  history of blood clotting or bleeding abnormalities;
  myocardial infarction within the past 2 months;
  documented thromboembolic event within the past 12 months;
  rheumatic heart disease;
  awaiting cardiac transplantation or other cardiac surgery within the next 12 months;
  unstable angina;
  acute illness or active systemic infection or sepsis;
  diagnosed atrial myxoma or interatrial baffle or patch;
  presence of implanted pacemaker, implantable cardioverter defibrillator, tissue-embedded, or iron-containing metal fragments;
  significant pulmonary disease or any other disease or malfunction of the lungs or respiratory system that produces chronic symptoms;
  significant congenital anomaly;
  pregnancy or lactating;
  enrollment in an investigational study evaluating another device, biologic, or drug;
  pulmonary vein stenosis;
  presence of intramural thrombus, tumor or other abnormality that precludes vascular access, or manipulation of the catheter;
  presence of an IVC filter;
  presence of a condition that precludes vascular access;
  life expectancy or other disease processes likely to limit survival to less than 12 months;
  contraindication to use of contrast agents for MRI;
  presence of iron-containing metal fragments in the patient; or
  unresolved pre-existing neurological deficit.

223. Use of any previous clause, wherein the multi-electrode radiofrequency balloon catheter comprises:
  a compliant balloon with a plurality of electrodes configured to deliver RF energy to tissue of all targeted pulmonary veins and sense temperature at each electrode.

224. Use according to Clause 223, wherein the plurality of electrodes is oriented circularly to circumferentially contact with an ostia of the pulmonary vein.

225. Use according to Clause 223, further comprising using the plurality of electrodes for visualization, stimulation, recording, and ablation.

226. Use according to Clause 223, wherein each electrode is configured so an amount of power delivered to each electrode is controlled independently.

227. Use according to Clause 223, wherein the multi-electrode radiofrequency balloon catheter further comprises a proximal handle, a distal tip, and a middle section disposed therebetween.

228. Use according to Clause 227, wherein the proximal handle is a deflection thumb knob allowing for unidirectional deflection, a balloon advancement mechanism, and a luer fitting for balloon inflation and irrigation.

229. Use according to Clause 223, wherein the multi-electrode radiofrequency balloon catheter further comprises
a high-torque shaft configured to be rotated to facilitate accurate positioning of the catheter tip to a desired; and
a unidirectional braided deflectable tip section.

230. Use of any previous clause, further comprising:
controlling irrigation to the multi-electrode radiofrequency balloon catheter with an irrigation pump.

231. Use of any previous clause, further comprising:
administering uninterrupted anticoagulation therapy at least 1 month prior to the procedure.

232. Use of any previous clause, wherein if the patient is receiving warfarin/coumadin therapy, the patient must have an international normalized ratio (INR)≥2 for at least 3 weeks prior to the procedure.

233. Use of any previous clause, wherein if the patient is receiving warfarin/coumadin therapy, the patient must be confirmed to have an international normalized ratio (INR)≥2 within 48 hours pre-procedure.

234. Use of any previous clause, further comprising: continuing anticoagulation therapy prior to the procedure.

235. Use of any previous clause, further comprising:
administering a transseptal puncture;
confirming an activated clotting time target of ≥350 sec. prior to inserting the multi-electrode radiofrequency balloon catheter into the left atrium and maintaining throughout the procedure;
introducing the multi-electrode radiofrequency balloon catheter;
introducing of a multi-electrode circular diagnostic catheter;
ablating the pulmonary vein with the multi-electrode radiofrequency balloon catheter;
determining in real time pulmonary vein isolation with the multi-electrode circular diagnostic catheter; and
confirming whether an entrance is blocked in the pulmonary vein.

236. Use of any previous clause, wherein the multi-electrode circular diagnostic catheter comprises:
an elongated body having a longitudinal axis;
a distal assembly distal the elongated body, the distal assembly having a helical form comprising a proximal loop and a distal loop, and a shape-memory support member extending through at least the proximal loop, the proximal loop and the distal loop being oriented obliquely at an angle relative to the longitudinal axis of the elongated body;
at least one irrigated ablation ring electrode mounted on the proximal loop;
a control handle proximal the elongated body; and
a contraction wire having a proximal end in the control handle and a distal end anchored in the proximal loop, the control handle including a first control member configured to actuate the contraction wire to contract the proximal loop,
wherein the proximal loop has a first flexibility and the distal loop has a second flexibility, and the second flexibility is greater than the first flexibility.

237. Use of an independently controlled multi-electrode radiofrequency balloon catheter to treat a plurality of patients for paroxysmal atrial fibrillation by applying energy to tissue of a subject's heart proximate to an esophagus, phrenic nerve, or lung, comprising:
achieving at least one of a predetermined clinical effectiveness and acute effectiveness of the procedure based on use of the multi-electrode radiofrequency balloon catheter and a multi-electrode diagnostic catheter in the isolation of the one or more targeted pulmonary veins by:
positioning an expandable member proximate to the left atrium, the expandable member of the multi-electrode radiofrequency balloon catheter having a longitudinal axis and including a plurality of electrodes disposed about the longitudinal axis, each electrode capable of being energized independently, the plurality of electrodes including a first electrode having a first radiopaque marker and a second electrode having a second radiopaque marker different from the first radiopaque marker;
viewing an image of the expandable member as well as the first and second radiopaque markers in the left atrium;
determining an orientation of the first and second radiopaque markers with respect to a
portion of the left atrium closest to the esophagus, phrenic nerve, or lung, of the subject;
moving one of the first and second radiopaque markers to a portion of the left atrium
closest to the esophagus, phrenic nerve or lung;
energizing one or more electrodes indexed to the one of the radiopaque markers proximate the portion close to the esophagus, phrenic nerve, or lung, at a lower energization setting as compared to other electrodes to create a transmural lesion in the left atrium with little or no effect to adjacent anatomical structures; and
electrophysiologically recording and stimulating the atrial region of the tissue proximate to the esophagus, phrenic nerve, or lung using the multi-electrode diagnostic catheter.

238. Use of administering an independently controlled multi-electrode radiofrequency balloon catheter for a procedure for atrial fibrillation, comprising:
delivering a multi-electrode radiofrequency balloon catheter to one or more targeted pulmonary veins;
ablating tissue of the pulmonary vein using the multi-electrode radiofrequency balloon catheter; and
achieving a predetermined effectiveness rate of pulmonary vein isolation.

239. Use according to Clause 238, wherein the predetermined effectiveness rate includes complication rates of 10% or less and is defined by existence of asymptomatic cerebral embolic lesions at a discharge magnetic resonance imaging (MRI).

240. Use according to Clause 238, wherein the predetermined effectiveness rate is defined by a freedom from documented atrial fibrillation, atrial tachycardia, or atypical atrial flutter episodes based on electrocardiographic data through an effectiveness evaluation period.

241. Use according to Clause 240, wherein the effectiveness evaluation period is approximately one year.

242. Use according to Clause 238, wherein the predetermined effectiveness rate is defined by pulmonary vein isolation touch-up by a focal catheter among all targeted pulmonary veins.

243. Use according to Clause 238, wherein the predetermined effectiveness rate is defined by using focal catheter ablation for non-PV triggers during the index procedure.

244. Use according to Clause 238, wherein the predetermined effectiveness rate comprises a long term effectiveness rate.

245. Use according to Clause 238, wherein the predetermined effectiveness rate is defined by an average number of RF applications per patient and RF time required to isolate all pulmonary veins.

246. Use according to Clause 238, wherein the predetermined effectiveness rate is defined by an average number of RF applications per vein and RF time required to isolate common pulmonary veins.

247. Use according to Clause 238, wherein the predetermined effectiveness rate is defined by an average number of RF applications per patient and RF time required to isolate common pulmonary veins.

248. Use according to Clause 238, wherein the predetermined effectiveness rate is defined by determining incidence of complication rates being 10% or less of post-ablation symptomatic and asymptomatic cerebral emboli as compared to pre-ablation.

249. Use according to Clause 238, wherein the predetermined effectiveness rate is defined by evaluating a presence of emboli-associated neurological deficits by at least one of NIHSS and mRS assessments.

250. Use of any previous clause, wherein the multi-electrode radiofrequency balloon catheter is configured for use in catheter-based cardiac electrophysiological mapping of the atria.

251. Use of any previous clause, wherein the multi-electrode radiofrequency balloon catheter is configured for cardiac ablation.

252. Use of any previous clause, wherein the multi-electrode radiofrequency balloon catheter comprises:
a compliant balloon with a plurality of electrodes bonded configured to deliver RF energy to tissue of the pulmonary vein and sense temperature at each electrode.

253. Use according to Clause 252, wherein the plurality of electrodes is oriented circularly to circumferentially contact with an ostia of the pulmonary vein.

254. Use according to Clause 252, further comprising: using the plurality of electrodes for visualization, stimulation, recording, and ablation.

255. Use according to Clause 252, wherein each electrode is configured so an amount of power delivered to each electrode is controlled independently.

256. Use according to Clause 252, wherein the multi-electrode radiofrequency balloon catheter further comprises a proximal handle, a distal tip, and a middle section disposed therebetween.

257. Use according to Clause 256, wherein the proximal handle is a deflection thumb knob allowing for unidirectional deflection, a balloon advancement mechanism, and a luer fitting for balloon inflation and irrigation.

258. Use according to Clause 252, wherein the multi-electrode radiofrequency balloon catheter further comprises
a high-torque shaft configured to be rotated to facilitate accurate positioning of the catheter tip to a desired; and
a unidirectional braided deflectable tip section.

259. Use according to Clause 252, wherein the balloon has a membrane, the balloon having a distal end and a proximal end defining a longitudinal axis, the multi-electrode radiofrequency balloon catheter further comprises:
a first substrate disposed on the membrane, the first substrate including a first radiopaque marker of a first form disposed thereon; and
a second substrate disposed on the membrane, the second substrate including a second radiopaque marker of a second form disposed thereon, the second form being different from the first form.

260. Use of any previous clause, further comprising:
controlling irrigation to the multi-electrode radiofrequency balloon catheter with an irrigation pump.

261. Use of any previous clause, wherein the effectiveness evaluation period is at least 91 days following:
the delivering the multi-electrode radiofrequency balloon catheter to the pulmonary vein; and
the ablating tissue of the pulmonary vein using the multi-electrode radiofrequency balloon catheter.

262. Use of any previous clause, wherein the effectiveness evaluation period is less than or equal to one year following:
the delivering the multi-electrode radiofrequency balloon catheter to the pulmonary vein; and
the ablating tissue of the pulmonary vein using the multi-electrode radiofrequency balloon catheter.

263. Use of administering an independently controlled multi-electrode radiofrequency balloon catheter for a procedure for atrial fibrillation, comprising:
delivering a multi-electrode radiofrequency balloon catheter to a pulmonary vein;
ablating tissue of the pulmonary vein using the multi-electrode radiofrequency balloon catheter; and
achieving a predetermined success rate of pulmonary vein isolation.

264. Use according to Clause 263, wherein the predetermined success rate is 60% for a population size of at least 40 patients.

265. Use of any previous clause, wherein a population size for the predetermined success rate is at least 300 patients.

266. Use of any previous clause, wherein a population size for the predetermined success rate is at least 200 patients.

267. Use of any previous clause, wherein a population size for the predetermined success rate is at least 100 patients.

268. Use of any previous clause, wherein a population size for the predetermined success rate is at least 50 patients.

269. Use of any previous clause, wherein the predetermined success rate is at least 60%.

270. Use of any previous clause, wherein the predetermined success rate is determined by evaluating the patient 7 days following:
the delivering the multi-electrode radiofrequency balloon catheter to the pulmonary vein; and
the ablating tissue of the pulmonary vein using the multi-electrode radiofrequency balloon catheter.

271. Use of any previous clause, wherein the predetermined success rate is determined by evaluating the patient 1 month following:
the delivering the multi-electrode radiofrequency balloon catheter to the pulmonary vein; and
the ablating tissue of the pulmonary vein using the multi-electrode radiofrequency balloon catheter.

272. Use of any previous clause, wherein the predetermined success rate is determined by evaluating the patient 6 months following:

the delivering the multi-electrode radiofrequency balloon catheter to the pulmonary vein; and the ablating tissue of the pulmonary vein using the multi-electrode radiofrequency balloon catheter.

273. Use of any previous clause, wherein the predetermined success rate is determined by evaluating the patient 12 months following:

the delivering the multi-electrode radiofrequency balloon catheter to the pulmonary vein; and the ablating tissue of the pulmonary vein using the multi-electrode radiofrequency balloon catheter.

274. Use of any previous clause, wherein the predetermined success rate further comprises:

confirming an entrance block in the pulmonary vein after at least one of adenosine and isoproterenol challenge.

275. Use of any previous clause, wherein the delivering step further comprises using a focal catheter.

276. Use of any previous clause, wherein the patient suffering at least one of the following events is deemed as unsuccessful pulmonary vein isolation, including:
  device or procedure related death;
  atrio-esophageal fistula, myocardial infarction;
  cardiac Tamponade/Perforation;
  thromboembolism;
  stroke/Cerebrovascular Accident (CVA);
  transient Ischemic Attach (TIA);
  phrenic Nerve Paralysis, Pulmonary Vein Stenosis;
  pericarditis;
  pulmonary Edema;
  major Vascular Access Complication/Bleeding; and
  hospitalization (initial or prolonged).

277. Use of any previous clause, wherein the patient suffering at least one of the following events is deemed as unsuccessful pulmonary vein isolation, comprising:
  acute procedural failure;
  repeat ablation or surgical treatment for AF/AT/Atypical (left-side) AFL after the blanking period (after day 90 post index procedure);
  DC cardioversion for AF/AT/Atypical (left-side) AFL, continuous AF/AT/AFL on a standard 12-lead ECG even if the recording is less than 30 seconds in duration (after day 90 post index procedure);
  a new Class I and/or Class III AAD is prescribed for AF during effectiveness evaluation period (day 91-365 post index procedure) or prescribed during the blanking period and continued past 90 days;
  a previously failed Class I and/or Class III AAD (failed at or before screening) is taken for AF at a greater dose than the highest ineffective historical dose during the effectiveness evaluation period; and
  amiodarone is prescribed post procedure.

278. Use of administering an independently controlled multi-electrode radiofrequency balloon catheter for a procedure for cardiac electrophysiological ablation of pulmonary veins of the atria and treating drug refractory recurrent symptomatic pulmonary atrial fibrillation, comprising:

delivering a multi-electrode radiofrequency balloon catheter to a pulmonary vein;

ablating tissue of the pulmonary vein using the multi-electrode radiofrequency balloon catheter; and achieving a predetermined effectiveness rate of pulmonary vein isolation.

279. Use of administering an independently controlled multi-electrode radiofrequency balloon catheter for a procedure for cardiac electrophysiological ablation of pulmonary veins of the atria and drug refractory recurrent symptomatic pulmonary atrial fibrillation, comprising:

delivering a multi-electrode radiofrequency balloon catheter to a pulmonary vein;

ablating tissue of the pulmonary vein using the multi-electrode radiofrequency balloon catheter; and achieving pulmonary vein isolation and at least a 97% safety endpoint within seven (7) days of successful pulmonary vein isolation.

280. Use of administering an independently controlled multi-electrode radiofrequency balloon catheter for a procedure for drug refractory recurrent symptomatic pulmonary atrial fibrillation, comprising:

delivering a multi-electrode radiofrequency balloon catheter to a pulmonary vein;

ablating tissue of the pulmonary vein using the multi-electrode radiofrequency balloon catheter; and achieving pulmonary vein isolation and at least a 90% safety endpoint within seven (7) days of successful pulmonary vein isolation.

281. Use of any previous clause, wherein the safety endpoint is defined by a patient suffering a primary adverse event.

282. Use of any previous clause, wherein at least one risk factor for the patient is selected from the group consisting of:
  at least three (3) symptomatic episodes of atrial fibrillation that last lasting ≥1 minute within six (6) months before the method or use;
  at least one (1) atrial fibrillation episode electrocardiographically documented within twelve (12) months prior to enrollment. Electrocardiographic documentation can include, but is not limited to, electrocardiogram (ECG), Holter monitor, or telemetry strip;
  failing at least one (1) Class I or Class III AAD as evidenced by recurrent symptomatic atrial fibrillation or intolerable side effects to the AAD;
  age 18-75 years;
  secondary to electrolyte imbalance;
  thyroid disease;
  reversible or non-cardiac cause; and
  previous surgical or catheter ablation for atrial fibrillation.

283. Use of any previous clause, wherein the patient has at least one risk factor selected from the group consisting of:
  Patients known to require ablation outside the PV ostia and CTI region;
  Previously diagnosed with persistent or long-standing persistent atrial fibrillation and/or Continuous atrial fibrillation 7 days following the method or use procedure;
  any percutaneous coronary intervention within the past 2 months;
  repair or replacement or presence of a prosthetic valve;
  any carotid stenting or endarterectomy within the past 6 months;
  Coronary artery bypass grafting, cardiac surgery or valvular cardiac surgical procedure within the past 6 months;
  Documented left atrium thrombus within 1 day prior to the method or use procedure;
  left atrium antero posterior diameter >50 mm;
  Left Ventricular Ejection Fraction <40%;
  Contraindication to anticoagulation;
  History of blood clotting or bleeding abnormalities;
  Myocardial infarction within the past 2 months;
  Documented thromboembolic event (including transient ischemic attack) within the past 12 months;
  Rheumatic Heart Disease;
  Uncontrolled heart failure or New York Heart Association (NYHA) function class III or IV;

Awaiting cardiac transplantation or other cardiac surgery within the next 12 months;
Unstable angina;
Acute illness or active systemic infection or sepsis;
Diagnosed atrial myxoma or presence of an interatrial baffle or patch;
Presence of implanted pacemaker or implantable cardioverter defibrillator (ICD);
Significant pulmonary disease or any other disease or malfunction of the lungs or respiratory system that produces chronic symptoms;
Significant congenital anomaly;
women who are pregnant;
enrollment in an investigational study evaluating another device, biologic, or drug;
known pulmonary vein stenosis;
presence of intramural thrombus, tumor or other abnormality that precludes vascular access, or manipulation of the catheter;
presence of an inferior vena cava filter;
presence of a condition that precludes vascular access;
life expectancy or other disease processes likely to limit survival to less than 12 months;
presenting contra-indication for the devices; and
patient on amiodarone at any time during the past 3 months prior to enrollment.

284. Use of any previous clause, further comprising:
administering uninterrupted anticoagulation therapy at least 1 month prior to the procedure.

285. Use of any previous clause, wherein if the patient is receiving warfarin/coumadin therapy, the patient must have an international normalized ratio ≥2 for at least 3 weeks prior to the procedure.

286. Use of any previous clause, wherein if the patient is receiving warfarin/coumadin therapy, the patient must be confirmed to be ≥2 within 48 hours pre-procedure.

287. Use of any previous clause, further comprising: continuing anticoagulation therapy prior to the procedure.

288. Use of any previous clause, further comprising: targeting an activated clotting time of 350-400 seconds prior to inserting the catheter and throughout the procedure.

289. Use of any previous clause, further comprising: checking an activated clotting time levels every 15-30 minutes during the procedure to ensure an activated clotting time target of 350-400 seconds.

290. Use of any previous clause, further comprising:
administering a transseptal puncture;
confirming an activated clotting time target of ≥350 sec. prior to inserting the multi-electrode radiofrequency balloon catheter into the left atrium and maintaining throughout the procedure;
introducing the multi-electrode radiofrequency balloon catheter;
introducing of a multi-electrode circular diagnostic catheter;
ablating the pulmonary vein with the multi-electrode radiofrequency balloon catheter;
determining in real time pulmonary vein isolation with the multi-electrode circular diagnostic catheter; and
confirming whether an entrance is blocked in the pulmonary vein.

291. Use of any previous clause, wherein the multi-electrode circular diagnostic catheter comprises:
an elongated body having a longitudinal axis;
a distal assembly distal the elongated body, the distal assembly having a helical form comprising a proximal loop and a distal loop, and a shape-memory support member extending through at least the proximal loop, the proximal loop and the distal loop being oriented obliquely at an angle relative to the longitudinal axis of the elongated body;
at least one irrigated ablation ring electrode mounted on the proximal loop;
a control handle proximal the elongated body; and
a contraction wire having a proximal end in the control handle and a distal end anchored in the proximal loop, the control handle including a first control member configured to actuate the contraction wire to contract the proximal loop,
wherein the proximal loop has a first flexibility and the distal loop has a second flexibility, and the second flexibility is greater than the first flexibility.

292. Use of administering an independently controlled multi-electrode radiofrequency balloon catheter for a procedure for pulmonary vein isolation by applying energy to tissue of a subject's heart proximate to an esophagus, phrenic nerve, or lung, comprising:
achieving a predetermined effectiveness rate according to any of the previous clauses by:
positioning an expandable member proximate to the left atrium, the expandable member
having a longitudinal axis and including a plurality of electrodes disposed about the longitudinal axis, each electrode capable of being energized independently, the plurality of electrodes including a first electrode having a first radiopaque marker and a second electrode having a second radiopaque marker different from the first radiopaque marker;
viewing an image of the expandable member as well as the first and second radiopaque markers in the left atrium;
determining an orientation of the first and second radiopaque markers with respect to a
portion of the left atrium closest to the esophagus, phrenic nerve, or lung, of the subject;
moving one of the first and second radiopaque markers to a portion of the left atrium closest to the esophagus, phrenic nerve or lung; and
energizing one or more electrodes indexed to the one of the radiopaque markers proximate the portion close to the esophagus, phrenic nerve, or lung, at a lower energization setting as compared to other electrodes to create a transmural lesion in the left atrium with little or no effect to adjacent anatomical structures.

What is claimed is:
1. Use of a multi-electrode radiofrequency balloon catheter to treat a plurality of patients for paroxysmal atrial fibrillation, comprising:
delivering the multi-electrode radiofrequency balloon catheter having a plurality of electrodes for radiofrequency ablation and a diagnostic catheter to one or more targeted pulmonary veins;
ablating tissue of the one or more targeted pulmonary veins with one or more of the plurality of the electrodes of the multi-electrode radiofrequency balloon catheter;
diagnosing isolation of the one or more targeted pulmonary veins using the diagnostic catheter; and
achieving a predetermined clinical effectiveness and an acute effectiveness in the isolation of the one or more targeted pulmonary veins, during and approximately 3 months after the ablating step with the multi-electrode radiofrequency balloon catheter and the diagnosing step using the diagnostic catheter;
wherein the acute effectiveness comprises a safety rate that includes complication rates of approximately 10% or less and is defined by incidence of asymptomatic cerebral embolic lesions at a discharge magnetic resonance imaging (MRI).

2. Use of claim 1, wherein the acute effectiveness is further defined by success in confirming an entrance block in all of the one or more targeted pulmonary veins after an adenosine and/or isoproterenol challenge for greater than approximately 95% for the plurality of patients.

3. Use of claim 1, wherein the plurality of patients is at least approximately 100 patients.

4. Use of claim 1, further comprising achieving a predetermined acute effectiveness, wherein the predetermined acute effectiveness is defined by at least one of:
a complication rate of approximately 13% or fewer of the plurality of patients experiencing esophageal erythema after the ablating;
a complication rate of approximately 5-9% or fewer of the plurality of patients experiencing a primary adverse event by approximately 7 or more days after the ablating;
ulceration being absent in the plurality of patients after the ablating,
a total procedure time,
a total ablation time,
a total RF application time,
a total dwell time of the multi-electrode radiofrequency balloon catheter, and
a total time to isolate all targeted pulmonary veins.

5. Use of claim 1, wherein the acute effectiveness is defined by one or more of:
a number and a total time of applications by the multi-electrode radiofrequency balloon catheter per a location of all the one or more targeted pulmonary veins;
a number and a total time of applications by the multi-electrode radiofrequency balloon catheter per patient; or
a number and a total time of applications by the multi-electrode radiofrequency balloon catheter per the one or more targeted veins.

6. Use of claim 1, wherein the predetermined clinical effectiveness is defined by an incidence of early onset of one or more adverse events within a predetermined time of ablating the tissue of the one or more targeted pulmonary veins.

7. Use of claim 1, wherein the acute effectiveness is defined by confirming if there is an entrance block in all of the one or more targeted pulmonary veins after an adenosine and/or isoproterenol challenge, the acute effectiveness being defined by success greater than approximately 80% for the plurality of patients.

8. Use of claim 1, wherein the acute effectiveness is approximately 100% for the plurality of patients and is defined by electrically isolating all of the one or more targeted pulmonary veins without use of a focal ablation catheter.

9. Use of claim 1, wherein the predetermined clinical effectiveness is defined by approximately 10% or less complication rates related to incidence of post-ablation symptomatic cerebral emboli and the incidence of the asymptomatic cerebral emboli as compared to pre-ablation.

10. Use of a multi-electrode radiofrequency balloon catheter for administering a procedure to treat atrial fibrillation, comprising:
delivering the multi-electrode radiofrequency balloon catheter to one or more targeted pulmonary veins;
ablating tissue of the one or more targeted pulmonary veins using the multi-electrode radiofrequency balloon catheter at a maximum temperature setting being approximately about 55° C.; and
achieving a predetermined effectiveness rate of pulmonary vein isolation, the predetermined effectiveness rate being defined by determining incidence of complication rates being 10% or less of post-ablation symptomatic and asymptomatic cerebral emboli at a discharge magnetic resonance imaging (MRI) as compared to pre-ablation.

11. Use of claim 10, wherein the predetermined effectiveness rate is further defined by achieving pulmonary vein isolation and at least approximately 90% safety endpoint within seven (7) days of successful pulmonary vein isolation, wherein a safety endpoint is defined by a patient suffering a primary adverse event.

12. Use of claim 10, wherein the predetermined effectiveness rate is further defined by at least one of:
a freedom from documented atrial fibrillation, atrial tachycardia, or atypical atrial flutter episodes based on electrocardiographic data through an effectiveness evaluation period;
pulmonary vein isolation touch-up by a focal catheter among all of the one or more targeted pulmonary veins;
using focal catheter ablation for non-pulmonary vein triggers during an index procedure;
an average number of radio frequency (RF) applications per patient and RF time required to isolate all pulmonary veins;
an average number of RF applications per vein of the one or more targeted pulmonary veins and RF time required to isolate common pulmonary veins of the one or more targeted pulmonary veins;
an average number of RF applications per patient and RF time required to isolate the common pulmonary veins of the one or more targeted pulmonary veins;
evaluating a presence of emboli-associated neurological deficits by at least one of National Institutes of Health Stroke Scale and Modified Rankin Scale assessments.

13. Use of claim 10, wherein an effectiveness evaluation period of the predetermined effectiveness rate is less than or equal to approximately one year following:
delivering the multi-electrode radiofrequency balloon catheter to the one or more targeted pulmonary veins; and
ablating the tissue of the one or more targeted pulmonary veins using the multi-electrode radiofrequency balloon catheter.

14. Use of claim 10, further comprising: targeting an activated clotting time of 350-400 seconds prior to inserting the multi-electrode radiofrequency balloon catheter and throughout the procedure.

15. Use of a multi-electrode radiofrequency balloon catheter to treat a plurality of patients for paroxysmal atrial fibrillation, comprising:
evaluating a number and size of all targeted pulmonary veins and anatomy of a left atrium;
puncturing the transseptal;
selectively positioning a multi-electrode esophageal temperature monitoring device in a vasculature adjacent to all the targeted pulmonary veins;
selectively positioning the multi-electrode radiofrequency balloon catheter in the vasculature adjacent to all the targeted pulmonary veins, the multi-electrode radiofrequency balloon catheter having a plurality of electrodes for radiofrequency ablation;

selectively positioning a multi-electrode diagnostic catheter in the vasculature adjacent to all the targeted pulmonary veins;

ablating tissue of all the targeted pulmonary veins with one or more of the plurality of the electrodes of the multi-electrode radiofrequency balloon catheter;

confirming isolation of all the targeted pulmonary veins using the multi-electrode diagnostic catheter;

confirming existence of an entrance block in all the targeted pulmonary veins; and achieving a predetermined effectiveness rate for the plurality of patients being at least approximately 100 patients, the predetermined effectiveness rate being defined by determining incidence of complication rates being 10% or less of post-ablation asymptomatic cerebral emboli at a discharge magnetic resonance imaging (MRI).

16. Use of claim 15, wherein each of the plurality of electrodes are configured so an amount of power delivered to each of the plurality of electrodes are controlled independently.

17. Use of claim 15, further comprising:
administering uninterrupted anticoagulation therapy at least 1 month prior to ablating the tissue.

18. Use of claim 15, further comprising:
confirming an activated clotting time target of greater than or equal to approximately 350 seconds prior to inserting the multi-electrode radiofrequency balloon catheter into the left atrium;
wherein ablating the tissue of all the targeted pulmonary veins with the multi-electrode radiofrequency balloon catheter comprises ablating with a maximum temperature setting being approximately about 55° C.

19. Use of claim 15, wherein the plurality of patients is at least approximately 200 patients.

* * * * *